US012649744B2

(12) United States Patent
McCarthy et al.

(10) Patent No.: US 12,649,744 B2
(45) Date of Patent: Jun. 9, 2026

(54) N-(PYRIDIN-2-YL)-6,7,8,9-TETRAHYDRO-5H-5,8-EPIMINOCYCLOHEPTA[C]PYRIDINE-10-CARBOXAMIDE DERIVATIVES AND SIMILAR COMPOUNDS AS GPR65 MODULATORS FOR THE TREATMENT OF CANCER

(71) Applicant: PATHIOS THERAPEUTICS LIMITED, Abingdon (GB)

(72) Inventors: Tom McCarthy, Abingdon (GB); Alan Naylor, Abingdon (GB); Gavin Milne, Abingdon (GB); David Miller, Abingdon (GB); Maria Ieva, Abingdon (GB)

(73) Assignee: Pathios Therapeutics Limited, Milton (GB)

( * ) Notice: Subject to any disclaimer, the term of this patent is extended or adjusted under 35 U.S.C. 154(b) by 324 days.

(21) Appl. No.: 18/257,540

(22) PCT Filed: Dec. 17, 2021

(86) PCT No.: PCT/GB2021/053354
§ 371 (c)(1),
(2) Date: Jun. 14, 2023

(87) PCT Pub. No.: WO2022/136844
PCT Pub. Date: Jun. 30, 2022

(65) Prior Publication Data

US 2024/0051961 A1 Feb. 15, 2024

(30) Foreign Application Priority Data

Dec. 22, 2020 (GB) ...................................... 2020370
May 7, 2021 (GB) ...................................... 2106539

(Continued)

(51) Int. Cl.
*C07D 471/18* (2006.01)
*C07D 519/00* (2006.01)

(52) U.S. Cl.
CPC ......... *C07D 471/18* (2013.01); *C07D 519/00* (2013.01)

(58) Field of Classification Search
CPC ............................ C07D 471/18; C07D 519/00
See application file for complete search history.

(56) References Cited

U.S. PATENT DOCUMENTS

2023/0174484 A1* 6/2023 Kaul .................... C07D 409/14 514/64

FOREIGN PATENT DOCUMENTS

CN 108938638 A 12/2018
KR 2019 0124951 A 11/2019

(Continued)

OTHER PUBLICATIONS

Huang et al., "Allosteric ligands for the pharmacologically dark receptors GPR68 and GPR65", *Nature* 527(7579):477-483 (2015).

(Continued)

*Primary Examiner* — Timothy R Rozof
(74) *Attorney, Agent, or Firm* — Lathrop GPM LLP; Brian C. Trinque; Nicole Sassu

(57) ABSTRACT

The present invention relates to compounds of formula (I) as GPR65 modulators for the treatment of a proliferative disorder, such as e.g. cancer, an immune disorder, asthma, chronic obstructive pulmonary disease (CORD) or acute respiratory distress syndrome (ARDS). Preferred compounds are e.g. N-(Pyridin-2-yl)-6,7,8,9-tetrahydro-5H-5,8-epiminocyclohepta[c]pyridine-10-carboxamide derivatives and similar compounds, such as e.g. (5R,8S)—N-(4-chloro-5-(trifluoromethyl)pyridin-2-yl)-1-fluoro-6,7,8,9-tetrahydro-5H-5,8-epiminocyclohepta[c]pyridine-10-carboxamide (compound 1)

(I)

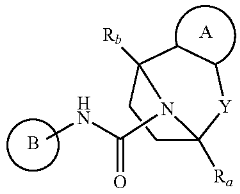

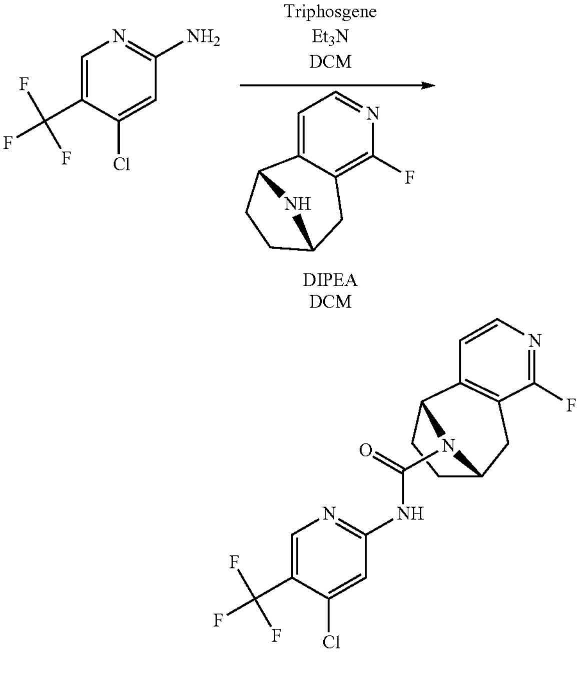

31 Claims, No Drawings

(30) Foreign Application Priority Data

| | | |
|---|---|---|
| Nov. 4, 2021 | (GB) | 2115861 |
| Nov. 30, 2021 | (GB) | 2117262 |

(56) References Cited

FOREIGN PATENT DOCUMENTS

| | | | |
|---|---|---|---|
| WO | WO 2004/029031 | A3 | 4/2004 |
| WO | WO 2005/066130 | A1 | 7/2005 |
| WO | WO 2007/095050 | A2 | 8/2007 |
| WO | WO 2021/245427 | A1 | 12/2021 |

OTHER PUBLICATIONS

International Search Report and Written Opinion for International Application No. PCT/GB2021/053354, mailed Mar. 4, 2022, 11 pages.

Ambinter Screening Library, published Mar. 26, 2020, Order Number Cat. Amb35455064. See CHEMCATS Acc. No. 0637685854 for the compound having the CAS Reg. No. 2370343-04-5.

Aurora Screening Compounds 3, published Feb. 27, 2020, Order Number Cat. K29.529.504. See CHEMCATS Acc. No. 1699401647 for the compound having the CAS Reg. No. 2371814-06-9.

Aurora Screening Compounds 3, published Feb. 27, 2020, Order Number Cat. K31.773.084. See CHEMCATS Acc. No. 1527435380 for the compound having the CAS Reg. No. 2401266-11-1.

Aurora Screening Compounds 3, published Feb. 27, 2020, Order Number Cat. K31.773.084. See CHEMCATS Acc. No. 1527435380 for the compound having the CAS Reg. No. 2406821-12-1.

Aurora Screening Compounds 3, published Feb. 27, 2020, Order Number Cat. K23.005.645. See CHEMCATS Acc. No. 0662363207 for the compound having the CAS Reg. No. 2468594-83-2.

Aurora Screening Compounds 3, published Feb. 27, 2020, Order Number Cat. K30.183.500. See CHEMCATS Acc. No. 1144707759 for the compound having the CAS Reg. No. 2470851-50-2.

Aurora Screening Compounds 3, published Feb. 27, 2020, Order Number Cat. K30.196.028. See CHEMCATS Acc. No. 2133514916 for the compound having the CAS Reg. No. 2471057-75-5.

FCH Group Premium Screening Compounds, published Nov. 9, 2020, Order Number Cat. FCG3597479194. See CHEMCATS Acc. No. 1997691661 for the compound having the CAS Reg. No. 2393493-43-9, i.e. N-(5-chloropyridin-3-yl)-4, 6, 12-triazatricyclo[7.2.1.0.cxa.{2,7}]dodeca-2,4,6-triene-12-carboxamide.

Katritzky et al., "Di(benzotriazol-1-yl)methanimine: A New Reagent for the Synthesis of Tri- and Tetrasubstituted Guanideines", *Journal of Organic Chemistry* 65:8080-8082 (2000).

Uorsy Screening Compounds, published Nov. 9, 2020, Order Number Cat. PB3594533194. See CHEMCATS Acc. No. 0904027761 for the compound having the CAS Reg. No. 2400182-48-9, i.e. N-(5-fluoropyridin-3-yl)-4,6,12-triazatricyclo[7.2.1.0.cxa.{2,7}]dodeca-2,4,6-triene-12-carboxamide.

Uorsy Screening Compounds, published Nov. 9, 2020, Order Number Cat. PB359556288. See CHEMCATS Acc. No. 0348805542 for the compound having the CAS Reg. No. 2402793-78-4, i.e. N-(5-chloro-4-methylpyridin-3-yl)-4,6,12-triazatricyclo[7.2.I .0.cxa.{2,7}]dodeca-2,4,6-triene-12-carboxamide.

* cited by examiner

N-(PYRIDIN-2-YL)-6,7,8,9-TETRAHYDRO-5H-5,8-EPIMINOCYCLOHEPTA[C]PYRIDINE-10-CARBOXAMIDE DERIVATIVES AND SIMILAR COMPOUNDS AS GPR65 MODULATORS FOR THE TREATMENT OF CANCER

The present invention relates to compounds that are capable of modulating GPR65. The compounds have potential therapeutic applications in the treatment of a variety of disorders, including proliferative and immune disorders.

BACKGROUND TO THE INVENTION

GPR65 is a Gs-coupled G protein-coupled receptor (GPCR) that is primarily expressed in immune cells and is activated by acidic extracellular pH to cause increases in cytoplasmic cyclic adenosine monophosphate (cAMP) (Wang, 2004). It has long been known that tumours typically undergo a switch in cellular metabolism from oxidative phosphorylation to aerobic glycolysis, which in turn results in an acidic extracellular microenvironment (Damaghi, 2013). Recently, it has been shown that this acidic microenvironment causes GPR65 activation in tumour-associated macrophages, resulting in an increase in cytoplasmic cAMP leading to transcription of the inducible cAMP early repressor (ICER). This, in turn, suppresses the secretion of tumour necrosis factor alpha (TNFα) to bias the macrophages toward an anti-inflammatory, tumour-permissive phenotype (Bohn, 2018). This GPR65-dependent pathway therefore appears to represent a mechanism by which tumours exploit their acidic microenvironment to evade detection by the immune system.

Autoimmune diseases are also often associated with an acidic local microenvironment (for instance, an inflamed joint). Recent studies also suggest that GPR65 acts through ICER in CD4+ T cells, to suppress IL-2 and hence bias cells toward an inflammatory Th17 phenotype, which is associated with increased pathogenicity in the context of autoimmune disease (Korn, 2009). Supporting this is the recent finding that ICER is required for Th17 differentiation (Yoshida, 2016) as well as that agonism of GPR65 leads to an increase in Th17 differentiation (Hernandez, 2018). Indeed, mutations in the GPR65 locus are associated with several autoimmune diseases, such as multiple sclerosis, ankylosing spondylitis, inflammatory bowel disease, and Crohn's disease (Gaublomme, 2015). One recent study found that mice with CD4+ T cells lacking GPR65 were protected from developing the disease autoimmune encephalomyelitis (EAE) (Gaublomme, 2015).

Thus, GPR65 appears to act through ICER to promote an anti-inflammatory and tumour-permissive phenotype in tumour associated macrophages and an inflammatory Th17 phenotype in CD4+ T cells that is associated with autoimmune disease. GPR65 signalling, therefore, represents an attractive pathway for therapeutic intervention for the treatment of both cancer and autoimmune diseases. There is therefore an ongoing need to develop new small molecule GPR65 modulators.

The present invention seeks to provide compounds that are capable of modulating GPR65. As made clear from the above discussion, such compounds have potential therapeutic applications in the treatment of a variety of disorders, including proliferative disorders and immune disorders, as well as asthma and chronic obstructive pulmonary disease.

STATEMENT OF INVENTION

A first aspect of the invention relates to a compound of formula (I), or a pharmaceutically acceptable salt or solvate thereof, (I)

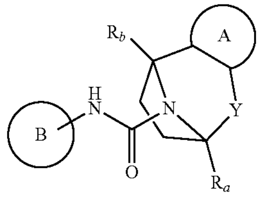

wherein:

ring A is a 5 or 6 membered aromatic or heteroaromatic ring, wherein said aromatic or heteroaromatic ring is optionally substituted with one or more substituents selected from halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11'}$, OH, alkyl, haloalkyl, and aralkyl;

ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl, $CO_2$-alkyl, and O-aryl;

Y is selected from C═N—OH, and $CR_{10}R_{10'}$, wherein $R_{10}$ and $R_{10'}$ are each independently selected from H, F, alkyl, and haloalkyl; preferably Y is $CH_2$;

$R_a$ and $R_b$ are each independently selected from H and alkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

Another aspect of the invention relates to a compound of formula (Ig), or a pharmaceutically acceptable salt or solvate thereof, (Ig)

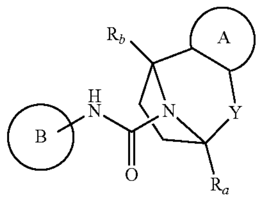

wherein:

ring A is a benzene, pyridine, pyridone, pyridine N-oxide, pyrimidone, pyridazine, pyrazine, or isoxazole ring that is optionally substituted with one or more substituents selected from halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11'}$, OH, alkyl, haloalkyl, and aralkyl;

ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl, $CO_2$-alkyl, and O-aryl;

Y is selected from C═N—OH, and $CR_{10}R_{10'}$, wherein $R_{10}$ and $R_{10'}$ are each independently selected from H, F, alkyl, and haloalkyl; preferably Y is $CH_2$;

$R_a$ and $R_b$ are each independently selected from H and alkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

Another aspect of the invention relates to a compound of formula (Ih), or a pharmaceutically acceptable salt or solvate thereof, (Ih)

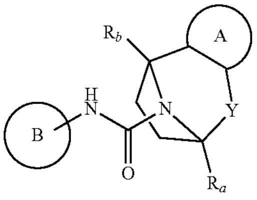

wherein:

ring A is selected from:

(i)

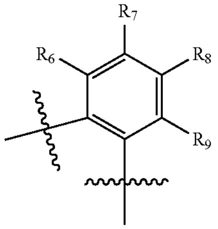

(ii)

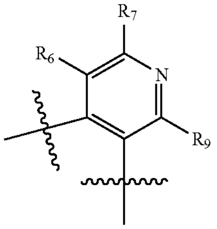

(iv)

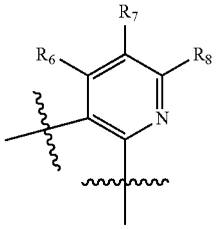

-continued (v)

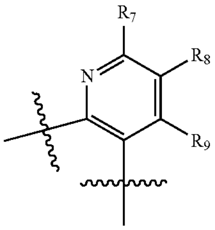

(vi)

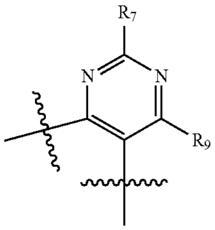

(vii)

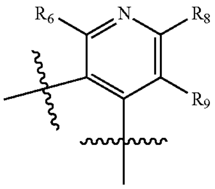

(viii)

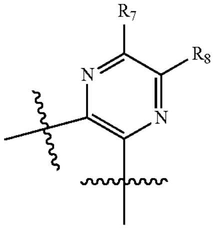

(ix)

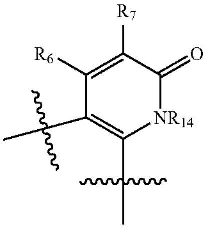

(x)

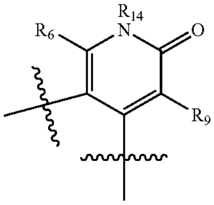

(xi)

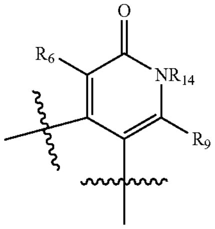

-continued (xii)

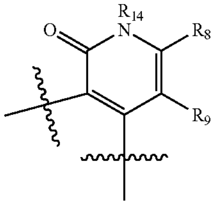

(xiii)

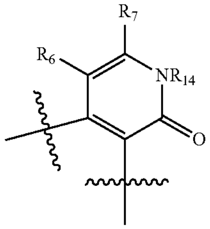

(xiv)

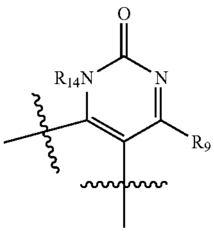

(xv)

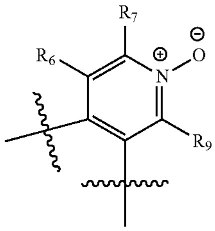

(xvi)

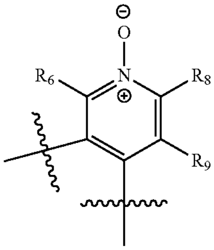

(xvii)

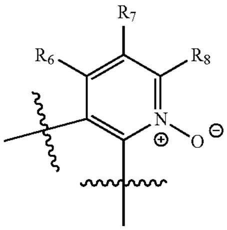

-continued (xviii)

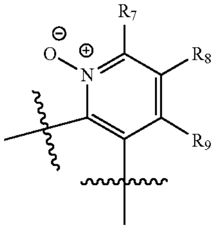

(xix)

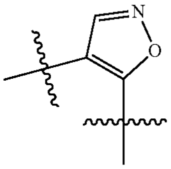

wherein $R_6$, $R_7$, $R_3$, and $R_9$ are each independently selected from H, halo, ON, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, ON, alkoxy, $NR_{11}R_{11'}$, OH, alkyl, haloalkyl, and aralkyl; and $R_a$ is H or alkyl;

ring B is a monocyclic or bicyclic heteroaromatic group containing at least one nitrogen atom, which is optionally substituted by one or more substituents selected from halo, ON, alkyl, alkoxy, haloalkyl, haloalkoxy, cycloalkyl, heterocycloalkyl, aryl, heteroaryl and O-aryl;

Y is selected from C═N—OH, and $CR_{10}R_{10'}$, wherein $R_{10}$ and $R_{10'}$ are each independently selected from H, F, alkyl, and haloalkyl; preferably Y is $OH_2$;

$R_a$ and $R_b$ are each independently selected from H and alkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

Advantageously, the presently claimed compounds are capable of modulating GPR65, thereby rendering the compounds of therapeutic interest in the treatment of various disorders, for example, in the field of oncology, immuno-oncology, and immunology.

Another aspect of the invention relates to a pharmaceutical composition comprising a compound as described herein and a pharmaceutically acceptable diluent, excipient, or carrier.

Another aspect of the invention relates to a compound or a pharmaceutical composition as described above for use as a medicament.

Another aspect of the invention relates to a compound or a pharmaceutical composition as described above for use in treating or preventing a disorder selected from a proliferative disorder, an immune disorder, asthma, chronic obstructive pulmonary disease (COPD) and acute respiratory distress syndrome (ARDS).

Another aspect of the invention relates to a method of treating a disorder, comprising administering to a subject a compound or a pharmaceutical composition as described above.

DETAILED DESCRIPTION

The present invention relates to compounds that are capable of modulating GPR65.

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{1-6}$ alkyl, for example, methyl, ethyl, propyl, isopropyl, butyl, isobutyl, tert-butyl, pentyl, hexyl. More preferably, the alkyl is a $C_{1-3}$ alkyl.

As used herein, the term "aryl" or "aromatic" refers to a $C_{6-12}$ aromatic group, which may be benzocondensed, for example, phenyl or naphthyl.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane. As used herein, the term "aryl" refers to a $C_{6-12}$ aromatic group, which may be benzocondensed, for example, phenyl or naphthyl.

"Haloalkyl" is defined herein as a straight-chain or branched alkyl radical as defined above, for example, methyl, ethyl, propyl, isopropyl, butyl, isobutyl, tert-butyl, pentyl, hexyl, that is substituted with one or more halogen atoms (that may be the same or different), such as fluorine, chlorine, bromine, and iodine. Preferably, the haloalkyl is a $C_{1-20}$ haloalkyl, more preferably a $C_{1-12}$ haloalkyl, even more preferably a $C_{1-10}$ haloalkyl or a $C_{1-6}$ haloalkyl, or a $C_{1-3}$ haloalkyl. Preferred examples are $CF_3$ and $CHF_2$, with $CF_3$ being particularly preferred.

"Alkoxy" is defined herein as an oxygen atom bonded to an alkyl group as defined above, for example methoxy, ethoxy, propoxy, isopropoxy, butoxy, isobutoxy, tert-butoxy, pentoxy and hexoxy. Preferably, the alkoxy is a $C_{1-20}$ alkoxy, more preferably a $C_{1-12}$ alkoxy, even more preferably $C_{1-10}$ alkoxy or a $C_{1-6}$ alkoxy, or a $C_{1-3}$ alkoxy. A particularly preferred example is methoxy ($—OCH_3$).

"Haloalkoxy" as defined herein is an alkoxy group as defined above substituted with one or more halogen atoms (that may be the same or different), such as fluorine, chlorine, bromine, and iodine. Preferably, the haloalkoxy is a $C_{1-20}$ haloalkoxy, more preferably a $C_{1-12}$ haloalkoxy, even more preferably a $C_{1-10}$ haloalkoxy or a $C_{1-6}$ haloalkoxy, or a $C_{1-3}$ haloalkoxy. Preferred examples are $OCF_3$ and $OCHF_2$, with $OCF_3$ being particularly preferred.

"Heteroaryl" or "heteroaromatic" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc.

"Heterocycloalkyl" refers to a cyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is monocyclic or bicyclic. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

"Aralkyl" is defined herein as an alkyl group as defined above substituted by one or more aryl groups as defined above.

In the formulae described herein, preferably alkyl is $C_1$-$C_6$ alkyl, haloalkyl is $C_1$-$C_6$ haloalkyl, and alkoxy is $C_1$-$C_6$ alkoxy.

Structural Representation of the Compounds

The compounds of the invention comprise a structure wherein the aromatic or heteroaromatic ring A is fused to a bicyclic nitrogen-containing moiety to form a tricyclic structure. The resulting tricyclic structure can exist in two different configurations as depicted below:

(I.1)

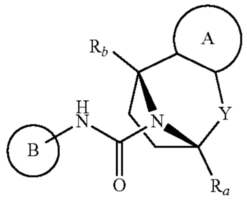

(I.2)

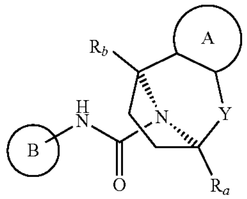

Alternatively, the structure can, for example, be represented (with $R_a$ and $R_b$ omitted for clarity), as follows:

(I.3)

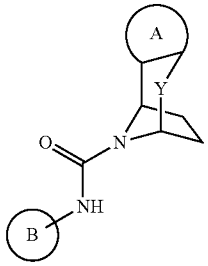

For the avoidance of doubt, the invention encompasses the compounds in either of the above configurations, as well as mixtures thereof, including racemic mixtures.

In one preferred embodiment, the compound is in the form of a mixture comprising a compound of formula (I.1) and its corresponding enantiomer of formula (I.2). In one preferred embodiment, the mixture is a racemic mixture, i.e. a 50:50 mixture of a compound of formula (I.1) and its corresponding enantiomer of formula (I.2).

Racemic mixtures can be used to prepare enantiomerically pure compounds of formula (I.1) or (I.2) by separating the compounds of formula (I.1) or (I.2) by standard methods, for example by chemical resolution using optically active acid or by the use of column chromatography or reverse-phase column chromatography using a substantially optically active (or "chiral") stationary phase as known to those skilled in the art. Racemic mixtures can also be used to prepare enantiomerically enriched mixtures of compounds of formula (I.1) or (I.2). Mixtures enriched with either a compound of formula (I.1) or (I.2) can also be obtained from the appropriate enantiomerically enriched precursors.

In one preferred embodiment of the invention, the compound is in the form of a mixture comprising enantiomers wherein the weight:weight ratio is at least approximately 2:1 or greater, preferably at least approximately 5:1 or greater, most preferably at least approximately 10:1 or greater in favour of the enantiomer that displays significant in vitro and/or in vivo activity (the eutomer).

In one particularly preferred embodiment, the compound is in the form of a mixture comprising a compound of formula (I.1) and its corresponding enantiomer of formula (I.2), wherein the weight:weight ratio of said compound of formula (I.1) to said compound of formula (I.2) is greater than 1.05:1, more preferably, greater than 2:1, even more preferably greater than 5:1, even more preferably greater than 10:1.

In one particularly preferred embodiment, the compound is in the form of a mixture comprising a compound of formula (I.1) and its corresponding enantiomer of formula (I.2), which is substantially enriched with said compound of formula (I.1).

In one embodiment, the compound is in the form of a mixture comprising a compound of formula (I.1) and its corresponding enantiomer of formula (I.2), wherein the weight:weight ratio of said compound of formula (I.2) to said compound of formula (I.1) is greater than 1.05:1, more preferably, greater than 2:1, even more preferably greater than 5:1, even more preferably greater than 10:1.

In one embodiment, the compound is in the form of a mixture comprising a compound of formula (I.1) and its corresponding enantiomer of formula (I.2), which is substantially enriched with said compound of formula (I.2).

For formulae (I') and (Ia)-(Ih), (j), (k), (m), (n), (o), (p) below, the compounds can be in either configuration (I.1) or (I.2) above. More preferably, they are of configuration (I.1).

The compounds described herein contain an optionally substituted 5 or 6-membered aromatic or heteroaromatic ring A, which is fused to the bicyclic nitrogen-containing moiety to form a tricyclic structure. The optional substituents are selected from halo, CN, alkoxy, $NR_{11}R_{11'}$, OH, alkyl, haloalkyl, aralkyl, aryl and heteroaryl. In some instances, ring A can exist in more than one tautomeric form. By way of illustration, where the heteroaromatic ring is substituted by an OH group, ring A can exist as two possible tautomers as shown below:

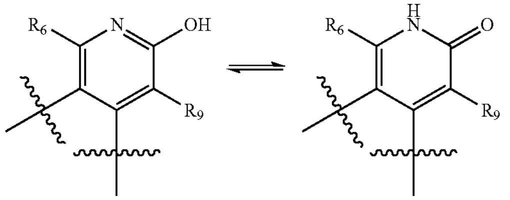

"2-hydroxypyridine" tautomer

"2-pyridone" tautomer

The 2-pyridone tautomer is believed to be the predominant solid state form. In solution, the energy difference between the two tautomeric forms is understood to be very small and is dependent on the polarity of the solvent. The skilled person would appreciate that other hydroxy substituted N-containing heteroaromatic groups (e.g. pyrimidine, other pyridine regioisomers) can be similarly represented in tautomeric form as shown above. The term "heteroaromatic" as used herein encompasses all tautomeric forms of the compounds.

Preferably, ring A is as defined herein, where the wavy lines denote attachment to the ring containing N and Y:

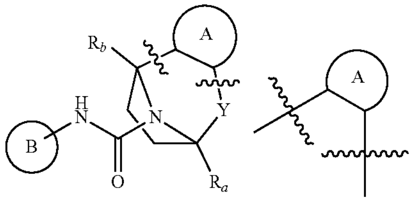

Compounds of Formula (I)

One aspect of the invention relates to a compound of formula (I), or a pharmaceutically acceptable salt or solvate thereof, as described above.

Preferably, for all embodiments described herein, $R_a$ and $R_b$ are each independently selected from H and Me. More preferably, $R_a$ and $R_b$ are both H.

In one preferred embodiment, ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl and O-aryl.

In one preferred embodiment, ring B is a monocyclic or bicyclic heteroaromatic group containing at least one nitrogen atom, which is optionally substituted by one or more substituents selected from halo, CN, alkyl, alkoxy, aryl, heteroaryl and O-aryl.

In one preferred embodiment, B is an optionally substituted monocyclic heteroaromatic group containing at least one nitrogen atom.

In one particularly preferred embodiment, the compound is of formula (I.1), or a pharmaceutically acceptable salt or solvate thereof, (I.1)

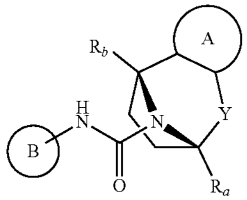

wherein A, Y, B, $R_a$ and $R_b$ are as defined above.

One embodiment of the invention relates to a compound of formula (I'), or a pharmaceutically acceptable salt or solvate thereof, (I')

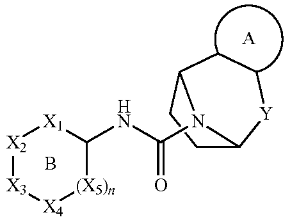

wherein:

ring A is a 5 or 6 membered aromatic or heteroaromatic ring, wherein said aromatic or heteroaromatic ring is optionally substituted with one or more substituents selected from halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11'}$, OH, alkyl, haloalkyl, and aralkyl;

n is 0 or 1;

$X_1$-$X_5$ form a heteroaromatic ring B, which is optionally substituted by one or more substituents selected from halo, CN, alkyl, alkoxy and haloalkyl;

Y is selected from $CH_2$, C=N—OH, and $CR_{10}R_{10'}$, wherein $R_{10}$ and $R_{10'}$ are each independently selected from H, F, alkyl, and haloalkyl; and $R_{11}$ and $R_{11'}$ are each independently selected from H, alkyl, haloalkyl, $COR_{12}$, $CO_2R_{13}$ and $SO_2R_{14}$, wherein $R_{12}$, $R_{13}$ and $R_{14}$ are each independently alkyl.

In general formula (I), $X_1$-$X_5$ form a monocyclic heteroaromatic ring B, which is optionally substituted by one or more substituents selected from halo, CN, alkyl, alkoxy and haloalkyl.

In one particularly preferred embodiment, the compound is of formula (I.1'):

(I.1')

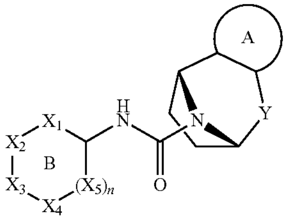

wherein ring A, and groups Y and $X_1$-$X_5$ and n are as described above. In one preferred embodiment, the compound is in enantiomerically pure form. In one preferred embodiment, the compound is in the form of a mixture that is enantiomerically enriched with a compound of formula (I.1'):

In another embodiment, the compound is of formula (I.2):

(I.2')

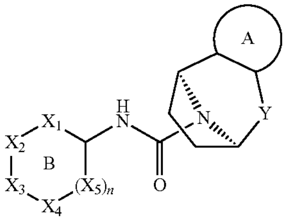

wherein ring A, and groups Y and $X_1$-$X_5$ and n are as described above. In one preferred embodiment, the compound is in enantiomerically pure form. In one preferred embodiment, the compound is in the form of a mixture that is enantiomerically enriched with a compound of formula (I.2):

In one preferred embodiment, the compound is in the form of a mixture comprising a compound of formula (I.1') and its corresponding enantiomer of formula (I.2). In one preferred embodiment, the mixture is a racemic mixture, i.e. a 50:50 mixture of a compound of formula (I.1') and its corresponding enantiomer of formula (I.2).

Racemic mixtures can be used to prepare enantiomerically pure compounds of formula (I.1') or (I.2) by separating the compounds of formula (I.1') or (I.2) by standard methods, for example by chemical resolution using optically active acid or by the use of column chromatography or reverse-phase column chromatography using a substantially optically active (or "chiral") stationary phase as known to those skilled in the art. Racemic mixtures can also be used to prepare enantiomerically enriched mixtures of compounds of formula (I.1') or (I.2'). Mixtures enriched with either a compound of formula (I.1') or (I.2) can also be obtained from the appropriate enantiomerically enriched precursors.

In one preferred embodiment of the invention, the compound is in the form of a mixture comprising enantiomers wherein the weight:weight ratio is at least approximately 2:1 or greater, preferably at least approximately 5:1 or greater, most preferably at least approximately 10:1 or greater in favour of the enantiomer that displays significant in vitro and/or in vivo activity (the eutomer).

In one particularly preferred embodiment, the compound is in the form of a mixture comprising a compound of formula (I.1') and its corresponding enantiomer of formula (I.2'), wherein the weight:weight ratio of said compound of formula (I.1') to said compound of formula (I.2') is greater than 1.05:1, more preferably, greater than 2:1, even more preferably greater than 5:1, even more preferably greater than 10:1.

In one particularly preferred embodiment, the compound is in the form of a mixture comprising a compound of formula (I.1') and its corresponding enantiomer of formula (I.2'), which is substantially enriched with said compound of formula (I.1').

In one embodiment, the compound is in the form of a mixture comprising a compound of formula (I.1') and its corresponding enantiomer of formula (I.2'), wherein the weight:weight ratio of said compound of formula (I.2') to said compound of formula (I.1') is greater than 1.05:1, more preferably, greater than 2:1, even more preferably greater than 5:1, even more preferably greater than 10:1.

In one embodiment, the compound is in the form of a mixture comprising a compound of formula (I.1') and its corresponding enantiomer of formula (I.2'), which is substantially enriched with said compound of formula (I.2').

In one preferred embodiment, ring B is an optionally substituted 6-membered heteroaromatic ring, i.e. n is 1, containing at least one heteroatom selected from N, O and S. Preferably, ring B is an optionally substituted 6-membered heteroaromatic ring containing at least one N. More preferably, ring B is selected from pyridinyl, pyrimidinyl, pyrazinyl, triazinyl and pyradizinyl, each of which may be optionally substituted. In one particularly preferred embodiment, ring B contains one N.

In another preferred embodiment, ring B is a 5-membered heteroaromatic ring, i.e. n is 0, containing at least one heteroatom selected from N, O and S. Preferably, ring B is an optionally substituted 5-membered heteroaromatic ring containing at least one N. More preferably, ring B is selected from thienyl, pyrrolyl, oxazolyl, imidazolyl, pyrazolyl, isoxazolyl, isothiazolyl, oxadiazolyl, triazolyl and thiadiazolyl, each of which may be optionally substituted. In one particularly preferred embodiment, ring B contains one N.

In one preferred embodiment, the compound of the invention is of formula (Ic), or a pharmaceutically acceptable salt or solvate thereof, (Ic)

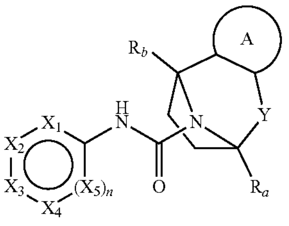

wherein where n is 0 or 1 and $X_1$-$X_5$ form a 5- or 6-membered heteroaromatic group containing at least one nitrogen atom, said heteroaromatic group being optionally substituted by one or more substituents selected from halo, CN, alkyl, alkoxy, haloalkyl, haloalkoxy, aryl, heteroaryl and O-aryl. More preferably, said heteroaromatic group is optionally substituted by one or more substituents selected from halo, CN, alkyl, alkoxy, haloalkyl, aryl, heteroaryl and O-aryl.

In one preferred embodiment, said compound is of formula (Ic) wherein n is 1, and $X_1$-$X_5$ form a 6-membered heteroaromatic group selected from pyridin-2-yl, pyridin-3-yl, pyridin-4-yl, pyrazin-2-yl, pyrazin-3-yl, pyrimidin-2-yl, pyrimidin-4-yl and pyrimidin-5-yl, each of which is optionally substituted by one or more substituents selected from halo, haloalkoxy, CN, alkoxyl, alkyl, haloalkyl, aryl, heteroaryl and O-aryl. More preferably, said heteroaromatic group is optionally substituted by one or more substituents selected from halo, CN, alkoxyl, alkyl, haloalkyl, aryl, heteroaryl and O-aryl. Even more preferably, said heteroaromatic group is optionally substituted by one or more substituents selected from H, halo, CN, alkoxyl, alkyl and haloalkyl.

In one preferred embodiment, the compound of the invention is of formula (Ia), or a pharmaceutically acceptable salt or solvate thereof, (Ia)

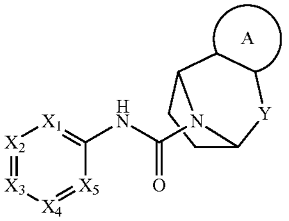

wherein:

ring A is a 5 or 6 membered aromatic or heteroaromatic ring, wherein said aromatic or heteroaromatic ring is optionally substituted with one or more substituents selected from F, Cl, Br, I, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from F, Cl, Br, I, CN, alkoxy, $NR_{11}R_{11'}$, OH, alkyl, haloalkyl, and aralkyl;

Y is selected from $CH_2$, C═N—OH, and $CR_{10}R_{10'}$, wherein $R_{10}$ and $R_{10'}$ are each independently selected from H, F, alkyl, and haloalkyl;

$X_1$ is N or $CR_1$;

$X_2$ is N or $CR_2$;

$X_3$ is N or $CR_3$;

$X_4$ is N or $CR_4$;

$X_5$ is N or $CR_5$;

wherein at least one of $X_1$ to $X_5$ is N;

$R_1$-$R_5$ are each independently selected from H, halo, CN, alkoxyl, alkyl, haloalkyl, haloalkoxy, aryl, heteroaryl and O-aryl, more preferably, H, halo, CN, alkoxyl, alkyl and haloalkyl; and $R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

In one preferred embodiment of formula (Ia), $R_1$-$R_5$ are each independently selected from H, halo, CN, alkoxyl, alkyl, haloalkyl, aryl, heteroaryl and O-aryl, more preferably, H, halo, CN, alkoxyl, alkyl and haloalkyl.

In one preferred embodiment, at least one of $X_1$ and $X_5$ is N and $X_3$ is $CR_3$. Preferably, $X_2$ is $CR_2$ and $X_4$ is $CR_4$. Preferably, $R_3$ is selected from halo, haloalkyl, alkyl, alkoxy and CN. Even more preferably, $R_3$ is selected from halo and haloalkyl. More preferably still, $R_3$ is selected from C, F and $CF_3$, even more preferably, C and $CF_3$.

In one preferred embodiment, the compound of the invention is of formula (Ib), or a pharmaceutically acceptable salt or solvate thereof, (Ib)

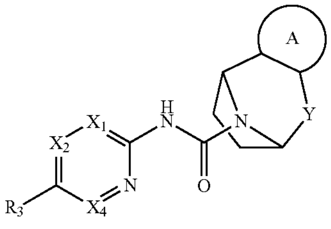

wherein:

ring A is a 5 or 6 membered aromatic or heteroaromatic ring, wherein said aromatic or heteroaromatic ring is optionally substituted with one or more substituents selected from F, Cl, Br, I, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from F, Cl, Br, I, CN, alkoxy, $NR_{11}R_{11'}$, OH, alkyl, haloalkyl, and aralkyl;

Y is selected from $CH_2$, C=N—OH, and $CR_{10}R_{10'}$, wherein $R_{10}$ and $R_{10'}$ are each independently selected from H, F, alkyl, and haloalkyl;

$X_1$ is N or $CR_1$;

$X_2$ is N or $CR_2$;

$X_4$ is N or $CR_4$;

$R_1$, $R_2$, $R_3$ and $R_4$ are each independently selected from H, halo, haloalkyl, haloalkoxy, alkyl, alkoxy, CN, aryl, heteroaryl and O-aryl, more preferably, H, halo, CN, alkoxyl, alkyl and haloalkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

In one preferred embodiment, for formula (Ib), $R_1$, $R_2$, $R_3$ and $R_4$ are each independently selected from H, halo, haloalkyl, alkyl, alkoxy, CN, aryl, heteroaryl and O-aryl, more preferably, H, halo, CN, alkoxyl, alkyl and haloalkyl.

In one preferred embodiment, $R_3$ is selected from halo and haloalkyl, and is more preferably selected from C, F and $CF_3$.

In one preferred embodiment, the compound is of formula (Ib), wherein $X_1$ is N or $CR_1$, $X_2$ is N or $CR_2$, $X_3$ is $CR_3$ and $X_4$ is $CR_4$ In one preferred embodiment, the compound is of formula (Ib), wherein $X_1$ is $CR_1$, $X_2$ is $CR_2$, $X_3$ is $CR_3$ and $X_4$ is $CR_4$. Preferably, for this embodiment, $R_3$ is selected from halo, haloalkyl, alkyl, alkoxy and CN. Even more preferably, $R_3$ is selected from halo and haloalkyl. More preferably still, $R_3$ is selected from Cl, F and $CF_3$, even more preferably, $C_1$ and $CF_3$. Preferably, for this embodiment, $R_1$, $R_2$ and $R_4$ are each independently selected from H and halo, more preferably, H and Cl. More preferably, at least one of $R_2$ and $R_4$ is halo.

In one particularly preferred embodiment:

$X_3$ is $CR_3$, where $R_3$ is selected from halo, haloalkyl, alkyl, alkoxy and CN;

$X_1$ is $CR_1$, where $R_1$ is H;

$X_2$ is $CR_2$, where $R_2$ is selected from H, halo, haloalkyl, alkyl, alkoxy and CN;

$X_4$ is $CR_4$, where $R_4$ is selected from H, halo, haloalkyl, alkyl, alkoxy and CN;

wherein at least one of $R_2$ and $R_4$ is other than H.

In one particularly preferred embodiment:

$X_3$ is $CR_3$, where $R_3$ is selected from halo and haloalkyl;

$X_1$ is $CR_1$, where $R_1$ is H;

$X_2$ is $CR_2$, where $R_2$ is selected from H, halo and haloalkyl;

$X_4$ is $CR_4$, where $R_4$ is selected from H, halo and haloalkyl;

wherein at least one of $R_2$ and $R_4$ is other than H.

In one particularly preferred embodiment:

$X_3$ is $CR_3$, where $R_3$ is selected from halo and haloalkyl;

$X_1$ is $CR_1$, where $R_1$ is H;

$X_2$ is $CR_2$, where $R_2$ is selected from halo and haloalkyl;

$X_4$ is $CR_4$, where $R_4$ is H.

In one particularly preferred embodiment:

$X_3$ is $CR_3$, where $R_3$ is selected from halo and haloalkyl;

$X_1$ is $CR_1$, where $R_1$ is H;

$X_2$ is $CR_2$, where $R_2$ is H;

$X_4$ is $CR_4$, where $R_4$ is selected from halo and haloalkyl.

In one particularly preferred embodiment:

$X_3$ is $CR_3$, where $R_3$ is selected from Cl, F and $CF_3$, even more preferably, Cl and $CF_3$;

$X_1$ is $CR_1$, where $R_1$ is H;

$X_2$ is $CR_2$, where $R_2$ is selected from H and Cl;

$X_4$ is $CR_4$, where $R_4$ is selected from H and Cl;

wherein at least one of $R_2$ and $R_4$ is other than H.

In one particularly preferred embodiment:

$X_3$ is $CR_3$, where $R_3$ is selected from Cl, F and $CF_3$, even more preferably, Cl and $CF_3$;

$X_1$ is $CR_1$, where $R_1$ is H;

$X_2$ is $CR_2$, where $R_2$ is Cl;

$X_4$ is $CR_4$, where $R_4$ is H.

In one particularly preferred embodiment:

$X_3$ is $CR_3$, where $R_3$ is selected from Cl, F and $CF_3$, even more preferably, Cl and $CF_3$;

$X_1$ is $CR_1$, where $R_1$ is H;

$X_2$ is $CR_2$, where $R_2$ is H;

$X_4$ is $CR_4$, where $R_4$ is Cl.

In one particularly preferred embodiment:

$X_3$ is $CR_3$, where $R_3$ is selected from haloalkoxy and CN;

$X_1$ is $CR_1$, where $R_1$ is selected from H and haloalkyl;

$X_2$ is $CR_2$, where $R_2$ is selected from H and halo;

$X_4$ is $CR_4$, where $R_4$ is selected from H, halo and haloalkyl,

In one preferred embodiment of the invention, for compounds of formula (Ib), $X_4$ is N, $X_1$ is $CR_1$ and $X_2$ is $CR_2$. Preferably, for this embodiment, $R_1$ and $R_2$ are each independently selected from H and halo, more preferably, H and Cl.

In one preferred embodiment of the invention, for compounds of formula (Ib), $X_1$ is N, $X_2$ is $CR_2$ and $X_4$ is $CR_4$. Preferably, for this embodiment, $R_2$ and $R_4$ are both H.

In one preferred embodiment of the invention, for compounds of formula (Ib), $X_2$ is N, $X_1$ is $CR_1$ and $X_4$ is $CR_4$. Preferably, for this embodiment, $R_1$ and $R_4$ are each independently selected from H and halo, more preferably, H and Cl.

In one preferred embodiment, the compound of the invention is of formula (Ia), wherein $X_3$ is N, $X_1$ is $CR_1$, $X_2$ is $CR_2$, $X_4$ is $CR_4$ and $X_5$ is $CR_5$. Preferably for this embodiment, $R_1$, $R_2$, $R_4$ and $R_5$ are each independently selected from H, halo and haloalkyl, more preferably, H, F and $CF_3$.

In one preferred embodiment, the compound of the invention is of formula (Ia), wherein $X_1$ is $CR_1$, $X_2$ is N, $X_3$ is $CR_3$, $X_4$ is $CR_4$ and $X_5$ is $CR_5$. Preferably for this embodiment, $R_1$, $R_3$, $R_4$ and $R_5$ are each independently selected from H, halo, heteroaryl, O-aryl and haloalkyl, more preferably, H, Cl, F, triazolyl, OPh and $CF_3$. Even more preferably, $R_1$, $R_4$ and $R_5$ are each independently selected from H, halo and haloalkyl, and $R_3$ is selected from heteroaryl and O-aryl. More preferably, $R_1$, $R_4$ and $R_5$ are each independently selected from H, Cl, F and $CF_3$, and $R_3$ is selected from triazolyl and OPh.

In one particularly preferred embodiment, the compound of the invention is of formula (Ib.1), or a pharmaceutically acceptable salt or solvate thereof, (Ib.1)

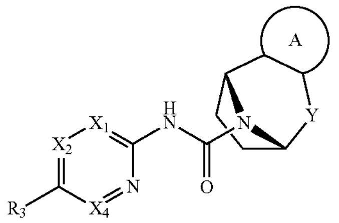

wherein A, Y, $X_1$, $X_2$, $X_4$ and $R_3$ are as defined above.

In one preferred embodiment, the compound is in enantiomerically pure form. In one preferred embodiment, the compound is in the form a mixture that is enantiomerically enriched with a compound of formula (Ib.1):

In another embodiment, the compound is of formula (Ib.2), or a pharmaceutically acceptable salt or solvate thereof, (Ib.2)

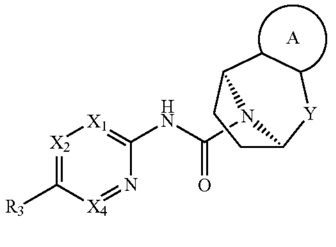

wherein A, Y, $X_1$, $X_2$, $X_4$ and $R_3$ are as defined above.

In one preferred embodiment, the compound is in enantiomerically pure form. In one preferred embodiment, the compound is in the form a mixture that is enantiomerically enriched with a compound of formula (Ib.2):

In one preferred embodiment, the compound is in the form of a mixture comprising a compound of formula (Ib.1) and its corresponding enantiomer of formula (Ib.2). In one preferred embodiment, the mixture is a racemic mixture, i.e. a 50:50 mixture of a compound of formula (Ib.1) and its corresponding enantiomer of formula (Ib.2).

Racemic mixtures can be used to prepare enantiomerically pure compounds of formula (Ib.1) or (Ib.2) by separating the compounds of formula (Ib.1) or (Ib.2) by standard methods, for example by chemical resolution using optically active acid or by the use of column chromatography or reverse-phase column chromatography using a substantially optically active (or "chiral") stationary phase as known to those skilled in the art. Racemic mixtures can also be used to prepare enantiomerically enriched mixtures of compounds of formula (Ib.1) or (Ib.2). Mixtures enriched with either a compound of formula (Ib.1) or (Ib.2) can also be obtained from the appropriate enantiomerically enriched precursors.

In one preferred embodiment of the invention, the compound is in the form of a mixture comprising enantiomers wherein the weight:weight ratio is at least approximately 2:1 or greater, preferably at least approximately 5:1 or greater, most preferably at least approximately 10:1 or greater in favour of the enantiomer that displays significant in vitro and/or in vivo activity (the eutomer).

In one particularly preferred embodiment, the compound is in the form of a mixture comprising a compound of formula (Ib.1) and its corresponding enantiomer of formula (Ib.2), wherein the weight:weight ratio of said compound of formula (Ib.1) to said compound of formula (Ib.2) is greater than 1.05:1, more preferably, greater than 2:1, even more preferably greater than 5:1, even more preferably greater than 10:1.

In one particularly preferred embodiment, the compound is in the form of a mixture comprising a compound of formula (Ib.1) and its corresponding enantiomer of formula (Ib.2), which is substantially enriched with said compound of formula (Ib.1).

In one embodiment, the compound is in the form of a mixture comprising a compound of formula (Ib.1) and its corresponding enantiomer of formula (Ib.2), wherein the weight:weight ratio of said compound of formula (Ib.2) to said compound of formula (Ib.1) is greater than 1.05:1, more preferably, greater than 2:1, even more preferably greater than 5:1, even more preferably greater than 10:1.

In one embodiment, the compound is in the form of a mixture comprising a compound of formula (Ib.1) and its corresponding enantiomer of formula (Ib.2), which is substantially enriched with said compound of formula (Ib.2).

In one preferred embodiment, the compound is of formula (Ic), wherein n is 0, and $X_1$-$X_4$ form a 5-membered heteroaromatic group containing at least one nitrogen atom, said heteroaromatic group being optionally substituted by one or more substituents selected from halo, CN, alkyl, alkoxy, haloalkyl, aryl, heteroaryl, $CO_2$-alkyl, cycloalkyl, heterocycloalkyl and O-aryl. Preferably, the heteroaromatic group is optionally substituted by one or more substituents selected from halo, CN, alkyl, alkoxy, haloalkyl, aryl, heteroaryl and O-aryl.

In one preferred embodiment, the compound is of formula (Ic), wherein n is 0, and $X_1$-$X_4$ form a 5-membered heteroaromatic group selected from oxadiazoyl, thiadiazolyl, imidazolyl, pyrrolyl, pyrazolyl, diazolyl, triazolyl, isoxazolyl, isothiazolyl, tetrazolyl, oxazolyl, and thiazolyl, and wherein said heteroaromatic group is optionally substituted by one or more substituents selected from halo, CN, alkyl, alkoxy, haloalkyl, aryl, heteroaryl, $CO_2$-alkyl, cycloalkyl, heterocycloalkyl and O-aryl. Preferably, the heteroaromatic group is optionally substituted by one or more substituents selected from halo, CN, alkyl, alkoxy, haloalkyl, aryl, heteroaryl and O-aryl.

In one preferred embodiment, the compound is of formula (Ic), wherein n is 0, and $X_1$-$X_4$ form a 5-membered heteroaromatic group selected 1H-imidazol-5-yl, 1H-imidazol-4-yl, 1H-imidazol-2-yl, 1H-pyrrol-2-yl, 1H-pyrrol-3-yl, 1H-pyrrol-4-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,3-triazol-4-yl, 1H-1,2,3-triazol-5-yl, thiazol-5-yl, thiazol-4-yl, thiazol-2-yl, 1H-tetrazolyl, 2H-tetrazolyl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, each of which is optionally substituted, preferably by one or more substituents selected from alkyl, halo, CN, alkoxy and haloalkyl.

In one highly preferred embodiment, the 5-membered heteroaromatic group is selected from 1,2,4-oxadiazol-3-yl, 1,2,5-oxadiazol-3-yl and 1,3,4-thiadiazol-2-yl, each of which is optionally substituted by one or more substituents selected from alkyl, halo, CN, alkoxy and haloalkyl.

In one preferred embodiment, the compound is of formula (Id), or a pharmaceutically acceptable salt or solvate thereof, (Id)

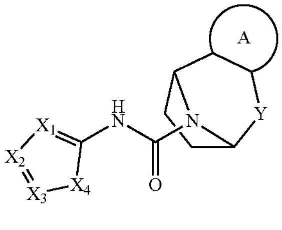

wherein:

$X_1$-$X_4$ form a heteroaromatic group containing at least one nitrogen atom, wherein:

$X_1$ is N or $CR_1$;

$X_2$ is N or $CR_2$;

$X_3$ is N or $CR_3$;

$X_4$ is selected from $NR_{15}$, O and S, where $R_{15}$ is H, alkyl or haloalkyl; and $R_1$-$R_3$ are each independently selected from H, halo, CN, alkoxyl, alkyl, haloalkyl, aryl, heteroaryl, heterocycloalkyl, cycloalkyl and O-aryl, more preferably, H, halo, CN, alkoxyl, alkyl, cyclopropyl, tetrahydropyranyl and haloalkyl.

In one preferred embodiment, for formula (Id), $R_1$-$R_3$ are each independently selected from H, halo, CN, alkoxyl, alkyl, haloalkyl, aryl, heteroaryl and O-aryl, more preferably, H, halo, CN, alkoxyl, alkyl and haloalkyl.

In one preferred embodiment, the compound is of formula (Id), wherein $X_1$ is N, $X_2$ is N, $X_3$ is $CR^3$ and $X^4$ is S.

In one preferred embodiment, the compound is of formula (Id), wherein $X_1$ is N, $X_2$ is N, $X_3$ is $CR_3$ and $X^4$ is O.

In one preferred embodiment, the compound is of formula (Id), wherein $X_1$ is N, $X_2$ is $CR_2$, $X_3$ is N and $X^4$ is O.

In one preferred embodiment, the compound is of formula (Id), wherein $X_1$ is $CR_1$, $X_2$ is N, $X_3$ is $CR^3$ and $X^4$ is S.

In one preferred embodiment, the compound is of formula (Id), wherein $X_1$ is N, $X_2$ is $CR_2$, $X_3$ is $CR^3$ and $X^4$ is S.

In one preferred embodiment, the compound is of formula (Id), wherein $X_1$ is $CR_1$, $X_2$ is $CR_2$, $X_3$ is N and $X^4$ is O.

In one preferred embodiment, the compound is of formula (Id), wherein $X_1$ is N, $X_2$ is N, $X_3$ is $CR^3$ and $X^4$ is S.

In one preferred embodiment, the compound is of formula (Ie), or a pharmaceutically acceptable salt or solvate thereof, (Ie)

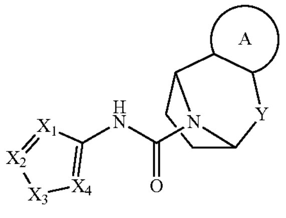

wherein:

$X_1$-$X_4$ form a heteroaromatic group containing at least one nitrogen atom, wherein:

$X_1$ is N or $CR_1$;

$X_2$ is N or $CR_2$;

$X_3$ is selected from $NR_{15}$, O and S, where $R_{15}$ is H, alkyl or haloalkyl;

$X_4$ is N or $CR_4$; and $R_1$, $R_2$ and $R_4$ are each independently selected from H, halo, CN, alkoxyl, alkyl, haloalkyl, aryl, heteroaryl, $CO_2$-alkyl and O-aryl, more preferably, H, halo, CN, alkoxyl, alkyl, $CO_2Me$ and haloalkyl.

In one preferred embodiment, for formula (Ie), $R_1$, $R_2$ and $R_4$ are each independently selected from H, halo, CN, alkoxyl, alkyl, haloalkyl, aryl, heteroaryl and O-aryl, more preferably, H, halo, CN, alkoxyl, alkyl and haloalkyl.

In one preferred embodiment, the compound is of formula (Ie), wherein: $X_1$ is $CR_1$, $X_2$ is N, $X_3$ is O and $X_4$ is N; or $X_1$ is N, $X_2$ is $CR_2$, $X_3$ is O and $X_4$ is N.

In one preferred embodiment, the compound is of formula (Ie), wherein $X_1$ is N, $X_2$ is N, $X_3$ is $CR^3$ and $X^4$ is S.

In one preferred embodiment, the compound is of formula (Ie), wherein: $X_1$ is $CR_1$, $X_2$ is $CR_2$, $X_3$ is $NR_{15}$ and $X_4$ is N.

In one preferred embodiment, the compound is of formula (Ie), wherein: $X_1$ is $CR_1$, $X_2$ is $CR_2$, $X_3$ is O and $X_4$ is N.

In one preferred embodiment, B is an optionally substituted bicyclic heteroaromatic group containing at least one nitrogen atom, preferably, an optionally substituted 9- or 10-membered bicyclic heteroaromatic group containing at least one nitrogen atom. Preferably, the bicyclic heteroaromatic group is a fused bicyclic heteroaromatic group.

In one preferred embodiment, B is a bicyclic heteroaromatic group selected from benzimidazolyl, pyrazolopyridinyl, indolyl, indolizinyl, isoindolyl, indazolyl, benzoxadiazolyl, quinolinyl, isoquinolinyl, cinnolinyl, phthalazinyl, quinazolinyl, quinoxalinyl and naphthyridinyl, and wherein said bicyclic heteroaromatic group is optionally substituted by one or more substituents selected from halo, CN, alkyl, alkoxy, haloalkyl, aryl, heteroaryl and O-aryl. In one highly preferred embodiment, B is a quinolin-6-yl group or a 2H-pyrazolo[3,4-c]pyridin-5-yl group, each of which is optionally substituted by one or more substituents selected from halo, CN, alkyl, alkoxy and haloalkyl.

In one preferred embodiment, the compound is of formula (If), or a pharmaceutically acceptable salt or solvate thereof, (If)

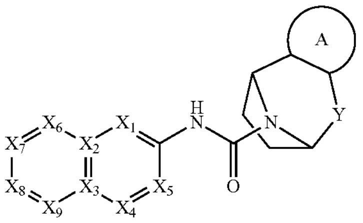

wherein $X_2$ and $X_3$ are both C, one, two or three of $X_1$, $X_4$, $X_5$-$X_9$ are N and the rest are selected from C—H, C-alkyl and C-haloalkyl.

In one preferred embodiment, the compound is of formula (If), wherein $X_5$ is N, $X_2$ and $X_3$ are both C, $X_1$, $X_4$, $X_5$, $X_6$ and $X_7$ are CH, and $X_3$ is C-haloalkyl more preferably, $CF_3$.

In one preferred embodiment, B is a bicyclic heteroaromatic group containing at least one nitrogen atom which is selected from the following:

(Ij)

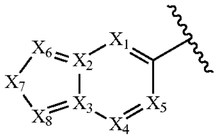

(Ik)

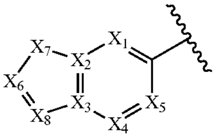

(Im)

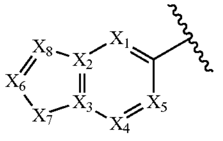

wherein:

$X_2$ and $X_3$ are both C;

$X_7$ is selected from O, S and $NR_{15}$, where $R_{15}$ is H, alky or haloalkyl; and one, two or three of $X_1$, $X_4$, $X_5$, $X_6$ and $X_8$ are N and the rest are selected from C—H, C-alkyl and C-haloalkyl.

In one preferred embodiment, B is a heteroaromatic group containing at least one nitrogen atom which is of formula:

(Ij)

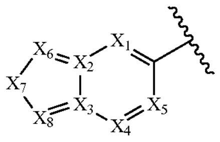

wherein $X_5$, $X_8$ are N, $X_2$ and $X_3$ are both C, $X_1$, $X_4$, $X_5$ and $X_6$ are CH, and $X_7$ is N-haloalkyl, more preferably N—$CHF_2$.

In another preferred embodiment, B is a heteroaromatic group containing at least one nitrogen atom which is of formula:

(Ij)

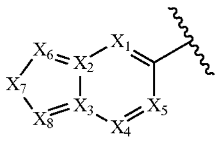

wherein $X_6$, $X_8$ are N, $X_2$ and $X_3$ are both C, $X_1$, $X_4$ and $X_5$ are CH, and $X_7$ is O.

In one preferred embodiment, B is a heteroaromatic group containing at least one nitrogen atom which is of formula:

(In)

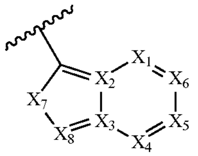

(Io)

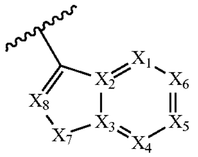

(Ip)

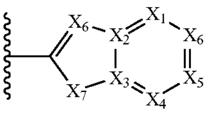

wherein:

$X_2$ and $X_3$ are both C;

$X_7$ is selected from O, S and $NR_{15}$, where $R_{15}$ is H, alkyl or haloalkyl; and one, two or three of $X_1$, $X_4$, $X_5$, $X_6$ and $X_3$ are N and the rest are selected from C—H, C-alkyl and C-haloalkyl.

In one preferred embodiment, B is a heteroaromatic group containing at least one nitrogen atom which is of formula:

(Io)

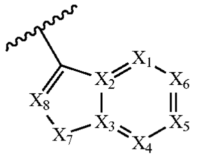

wherein $X_7$ is $NR_{15}$, $X_a$ is N, and $X_2$ and $X_3$ are C, and $X_1$, $X_4$, $X_5$ and $X_6$ are CH.

In one preferred embodiment of the invention, ring A is a benzene, pyridine, pyridone, pyridine N-oxide, pyrimidone, pyridazine, pyrazine, or isoxazole ring that is optionally substituted with one or more substituents selected from halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11'}$, OH, alkyl, haloalkyl, and aralkyl.

In one preferred embodiment of the invention, ring A is a benzene, pyridine, pyridone, pyridine N-oxide, pyrimidine, pyrimidone, pyridazine, pyrazine, or isoxazole ring that is optionally substituted with one or more substituents selected from F, C, Br, I, CN, $C_1$-$C_6$ alkoxy, $NR_{11}R_{11'}$, OH, $C_1$-$C_6$ alkyl, phenyl, and $C_1$-$C_6$ haloalkyl.

In one preferred embodiment of the invention, ring A is selected from:

(i)

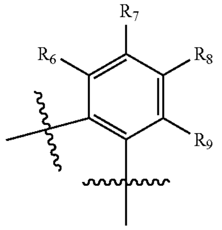

(ii)

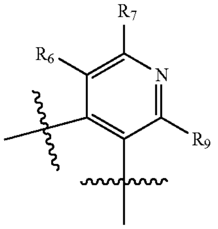

(iii)

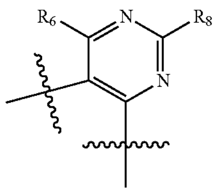

-continued
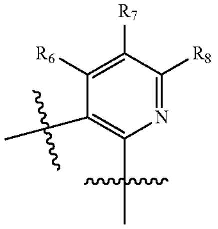
(iv)
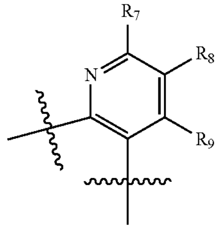
(v)
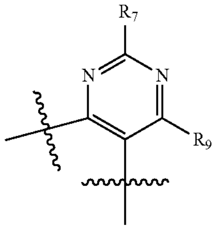
(vi)
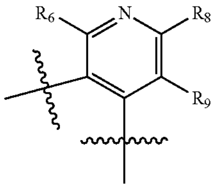
(vii)
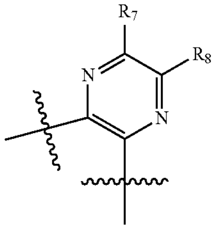
(viii)
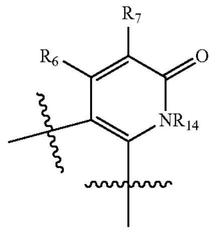
(ix)
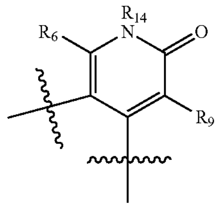
(x)
-continued
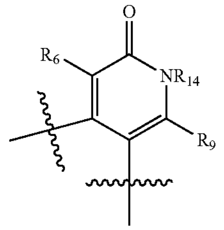
(xi)
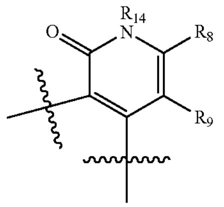
(xii)
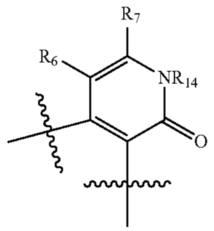
(xiii)
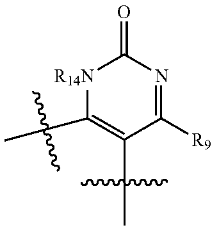
(xiv)
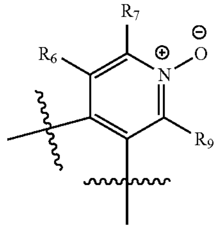
(xv)
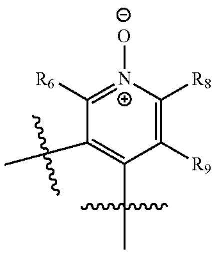
(xvi)

-continued (xvii)

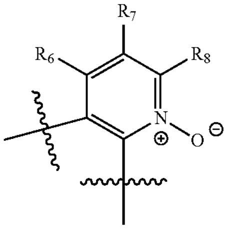

(xviii)

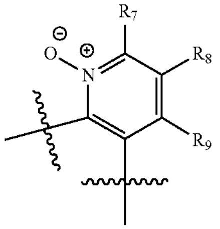

(xix)

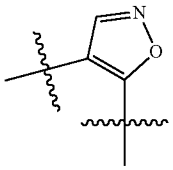

wherein $R_6$, $R_7$, $R_8$, and $R_9$ are each independently selected from H, F, Cl, Br, I, CN, alkoxy, $NR_{11}R_{11'}$, OH, alkyl, phenyl and haloalkyl, and $R_{14}$ is H or alkyl, more preferably H.

Preferably, $R_6$, $R_7$, $R_8$, and $R_9$ are each independently selected from H, F, Cl, Br, I, CN, $C_{1-6}$-alkoxy, $NR_{11}R_{11'}$, OH, $C_{1-6}$-alkyl, phenyl and haloalkyl.

In one preferred embodiment of the invention, ring A is selected from groups (i)-(ii) and (iv)-(xix) above.

In one preferred embodiment of the invention, ring A is selected from:

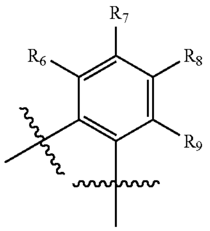

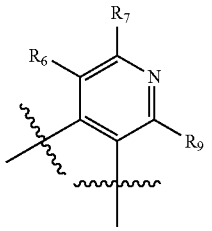

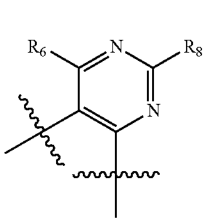

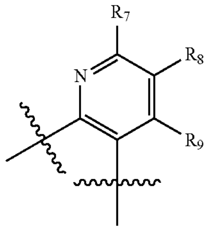

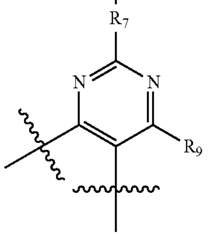

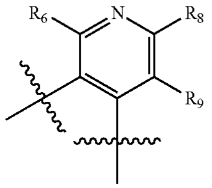

-continued

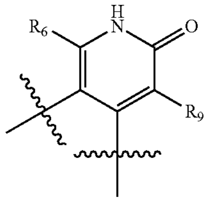

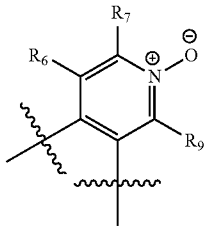

and is preferably selected from:

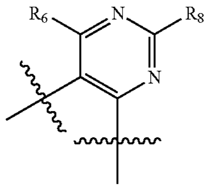

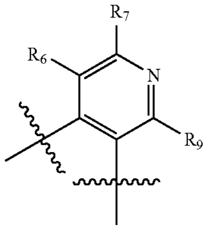

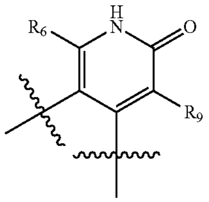

In another particularly preferred embodiment, ring A is selected from:

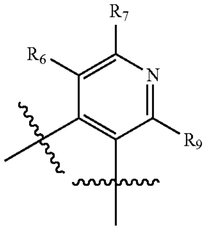

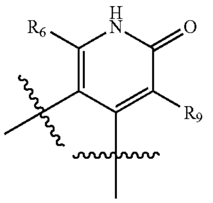

In another particularly preferred embodiment, ring A is:

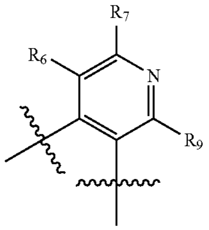

wherein $R_6$, $R_7$ and $R_3$ are each independently selected from H, Cl, Br and F, more preferably, H and F. More preferably, $R_6$ and $R_7$ are both H, and $R_9$ is F.

In another particularly preferred embodiment, ring A is:

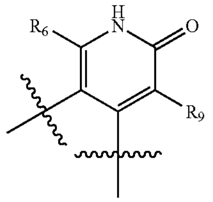

wherein $R_6$ and $R_9$ are each independently selected from H, Cl, Br and F, more preferably, H and F. More preferably, $R_8$ and $R_9$ are both H.

In one particularly preferred embodiment, ring A is:

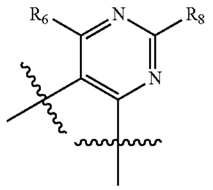

wherein $R_6$ and $R_3$ are each independently selected from H, Cl, Br and F, more preferably, H and F. More preferably, $R_6$ and $R_3$ are both H.

For all embodiments described herein, preferably $R_{10}$ and $R_{10'}$ are each independently selected from H and $C_1$-$C_6$ alkyl, preferably wherein $C_1$-$C_6$ alkyl is $CH_3$.

For all embodiments described herein, preferably Y is selected from $CH_2$ and C═N—OH.

More preferably, Y is $CH_2$.

For all embodiments described herein, preferably $R_{12}$, $R_{13}$ and $R_{16}$ are $C_{1-6}$-alkyl, more preferably $CH_3$.

Another aspect of the invention relates to a compound of formula (Ig), or a pharmaceutically acceptable salt or solvate thereof, (Ig)

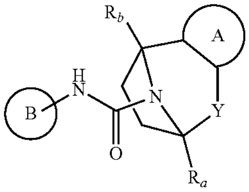

wherein:

ring A is a benzene, pyridine, pyridone, pyridine N-oxide, pyrimidone, pyridazine, pyrazine, or isoxazole ring that is optionally substituted with one or more substituents selected from halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11'}$, OH, alkyl, haloalkyl, and aralkyl;

ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl, $CO_2$-alkyl, and O-aryl;

Y is selected from $CH_2$, C═N—OH, and $CR_{10}R_{10'}$, wherein $R_{10}$ and $R_{10'}$ are each independently selected from H, F, alkyl, and haloalkyl;

$R_a$ and $R_b$ are each independently selected from H and alkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

For compounds of formula (Ig), preferably ring A is a benzene, pyridine, pyridone, pyridine N-oxide, pyrimidone, pyridazine, pyrazine, or isoxazole ring that is optionally substituted with one or more substituents selected from F, C, Br, I, CN, $C_1$-$C_6$ alkoxy, $NR_{11}R_{11'}$, OH, $C_1$-$C_6$ alkyl, phenyl, and $C_1$-$C_6$ haloalkyl.

For compounds of formula (Ig), preferably ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl and O-aryl.

Another aspect of the invention relates to a compound of formula (Ih), or a pharmaceutically acceptable salt or solvate thereof, (Ih)

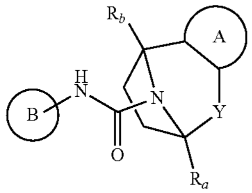

wherein:

ring A is selected from:

(i)

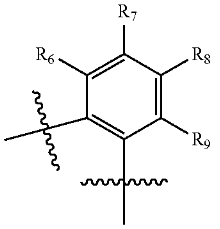

(ii)

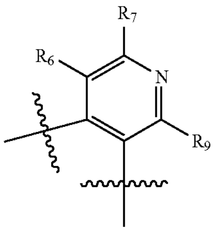

(iv)

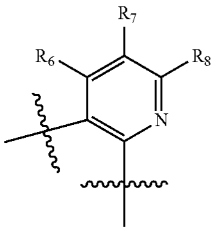

-continued
(v)
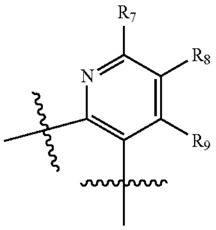
(vi)
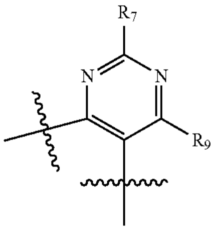
(vii)
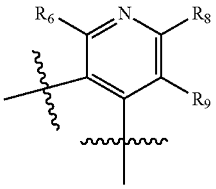
(viii)
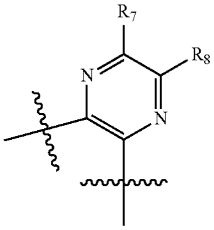
(ix)
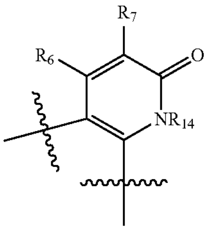
(x)
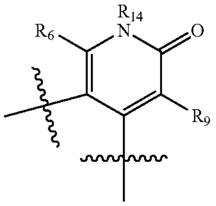
(xi)
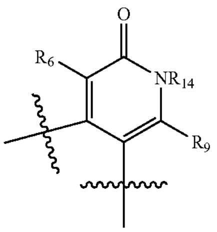
-continued
(xii)
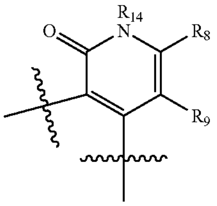
(xiii)
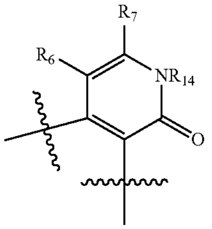
(xiv)
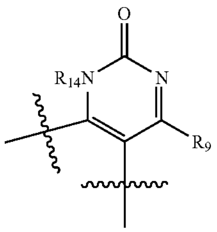
(xv)
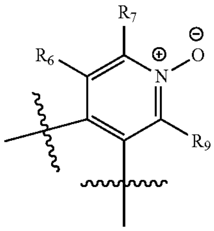
(xvi)
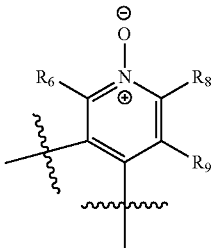
(xvii)
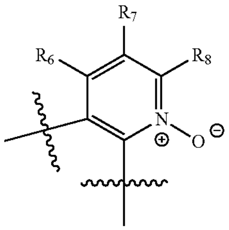

-continued (xviii)

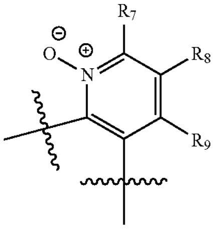

(xix)

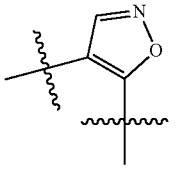

wherein $R_6$, $R_7$, $R_3$, and $R_9$ are each independently selected from H, halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11'}$, OH, alkyl, haloalkyl, and aralkyl; and $R_{14}$ is H or alkyl;

ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl, $CO_2$-alkyl and O-aryl;

Y is selected from $CH_2$, C═N—OH, and $CR_{10}R_{10'}$, wherein $R_{10}$ and $R_{10'}$ are each independently selected from H, F, alkyl, and haloalkyl;

$R_a$ and $R_b$ are each independently selected from H and alkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

Preferably, $R_6$, $R_7$, $R_3$, and $R_9$ are each independently selected from H, F, Cl, Br, I, CN, alkoxy, $NR_{11}R_{11'}$, OH, alkyl, phenyl and haloalkyl, and $R_{14}$ is H or alkyl, more preferably H.

For compounds of formula (Ih), preferably ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl and O-aryl.

Preferred substituent definitions and embodiments set forth above for formulae (I), (Ia)-(If), (j), (k), (n), (in), (o), (p) etc apply equally to Formulae (Ig) and (Ih). Specifically, the preferred definitions of A, B, $R_a$, $R_b$ and Y apply mutatis mutandis to Formulae (Ig) and (Ih). The invention also encompasses pharmaceutical compositions comprising compounds of Formulae (Ig) or (Ih) and a pharmaceutically acceptable diluent, excipient or carrier. Likewise the invention also encompasses compounds of Formulae (Ig) and (Ih) for use in the methods and therapeutic applications described herein.

In one preferred embodiment, the compound of the invention is selected from the following:

1

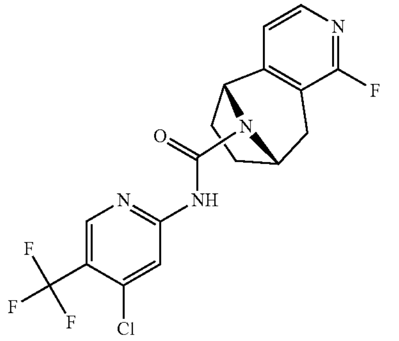

2

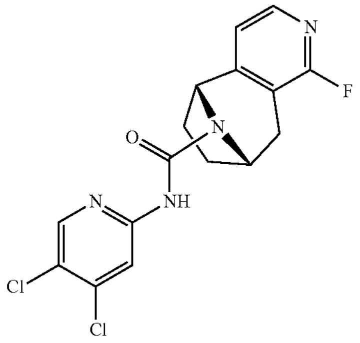

3

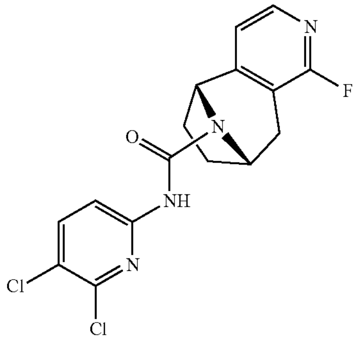

4

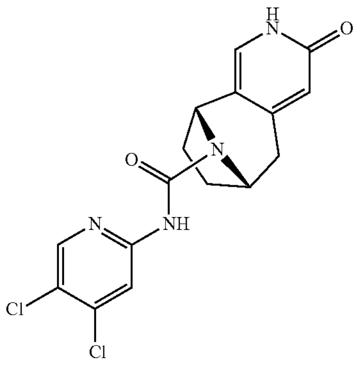

-continued
5
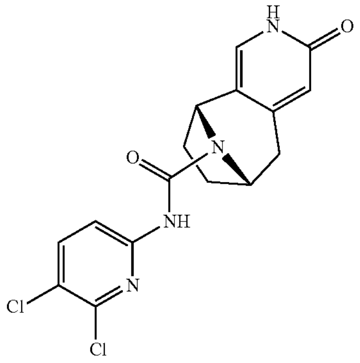
6
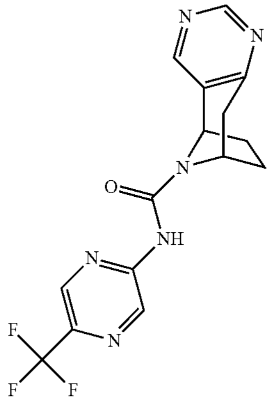
8
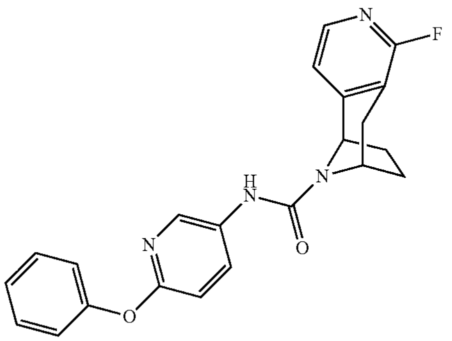
9
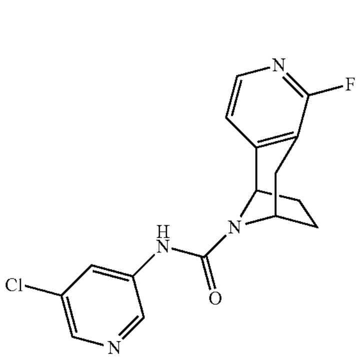
-continued
10
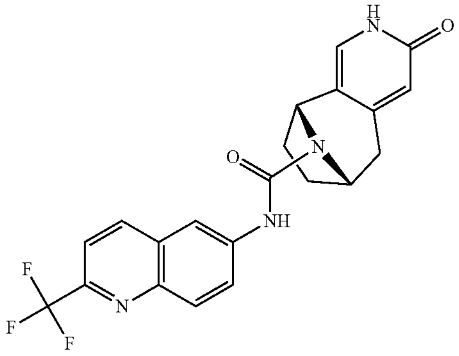
11
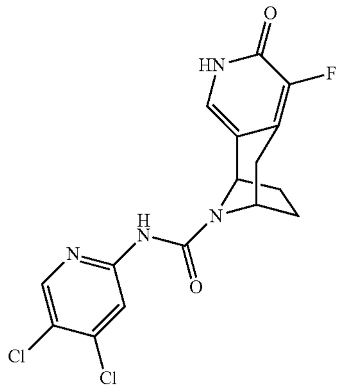
12
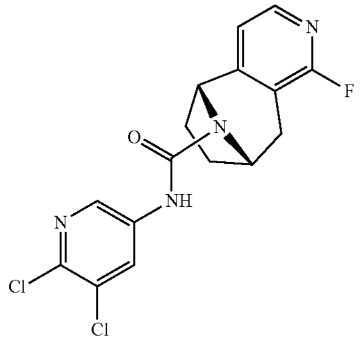
13
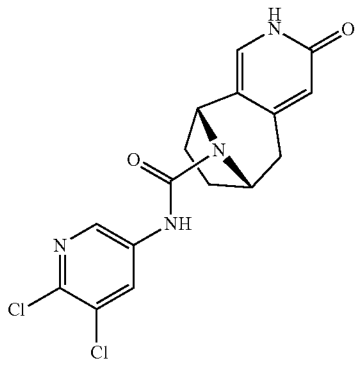

-continued
14
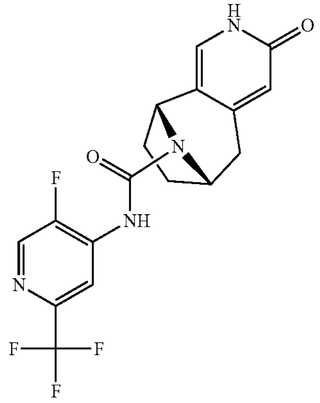
15
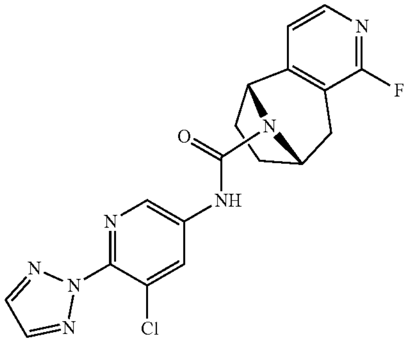
16
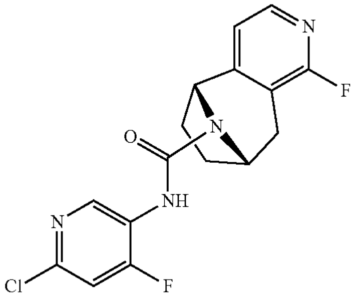
17
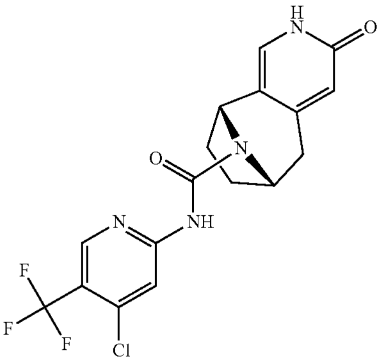
-continued
18
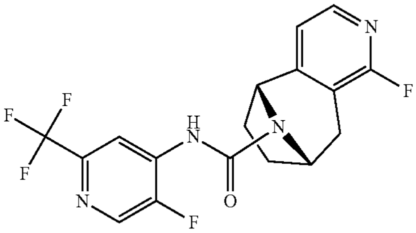
19
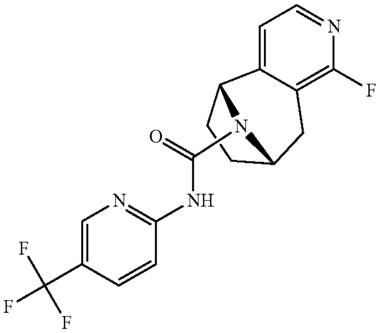
20
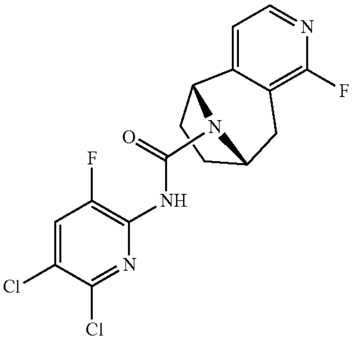
21
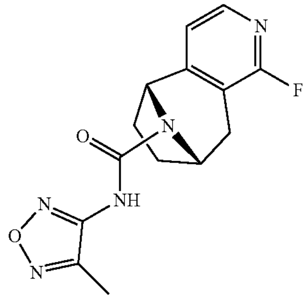
22
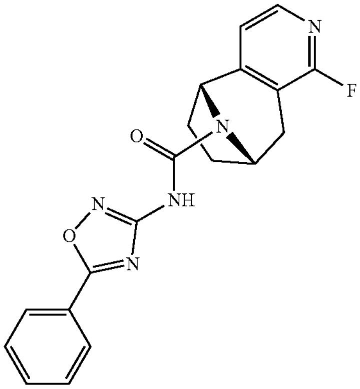

-continued
23
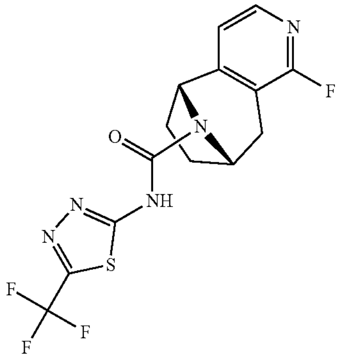
24
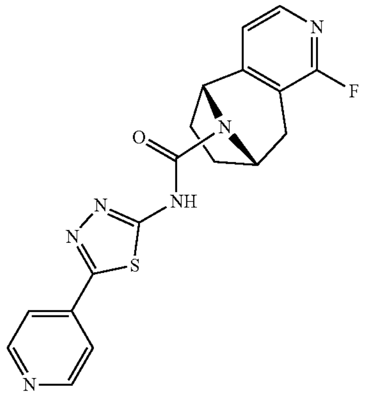
25
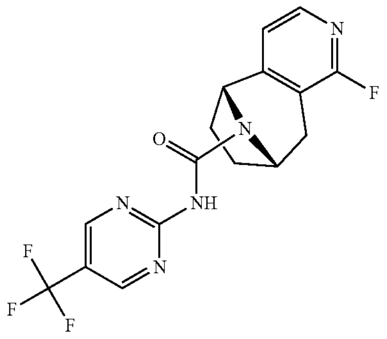
26
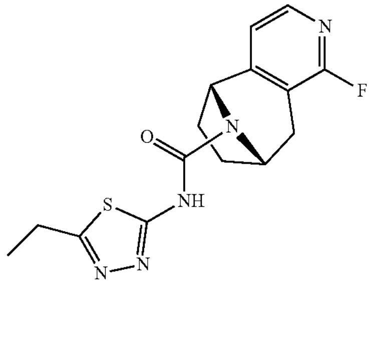
-continued
27
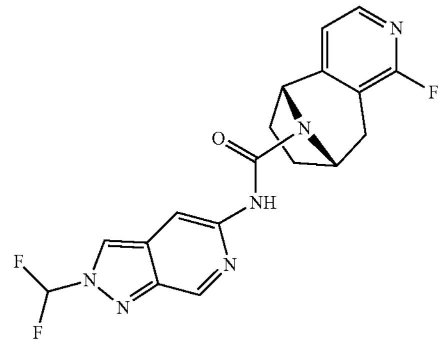
28
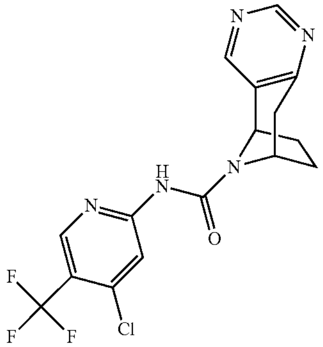
29
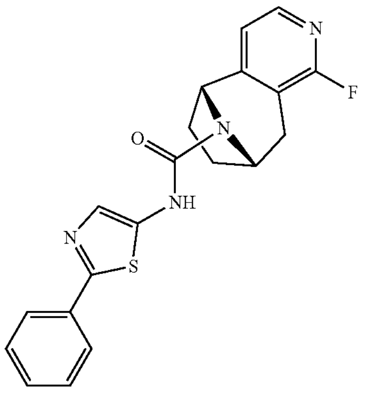
30
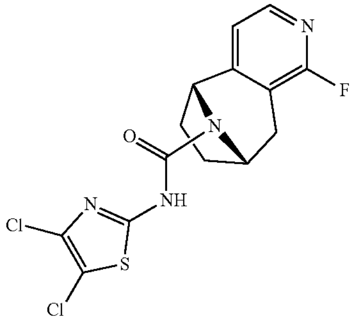

31
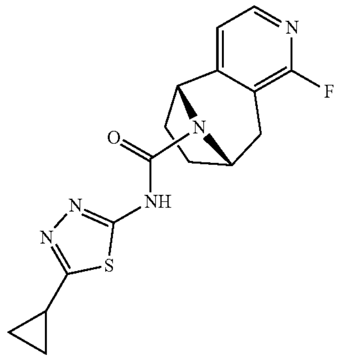
32
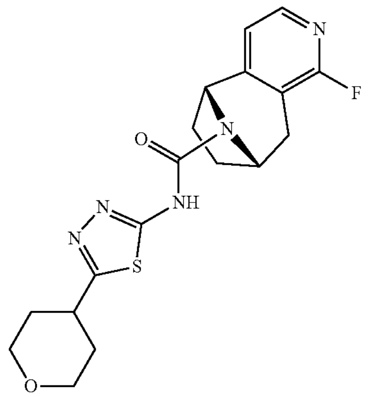
33
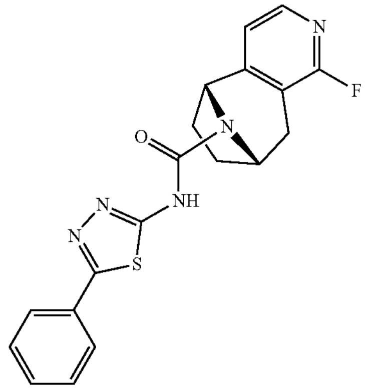
34
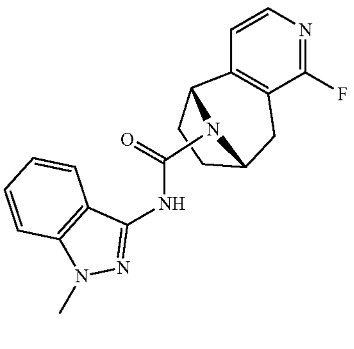
35
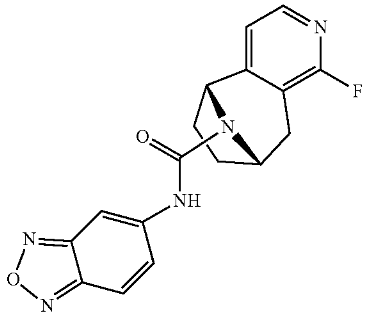
36
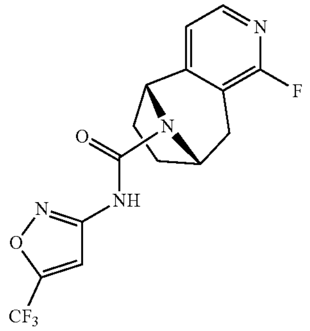
37
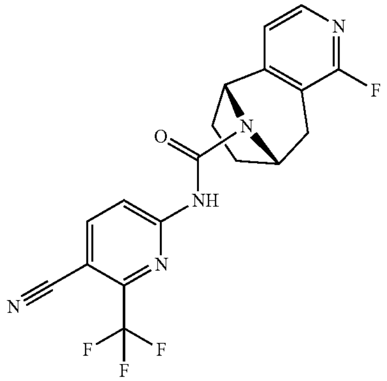
38
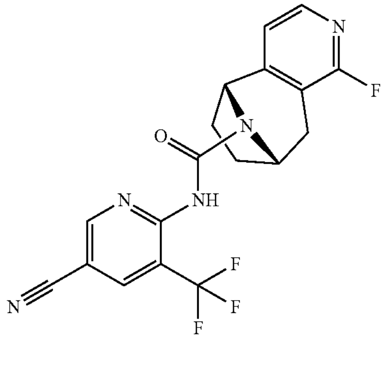

39
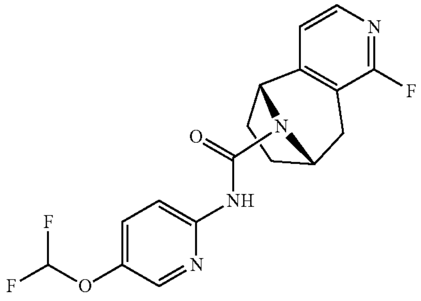
40
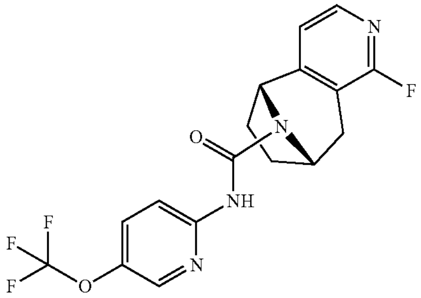
41
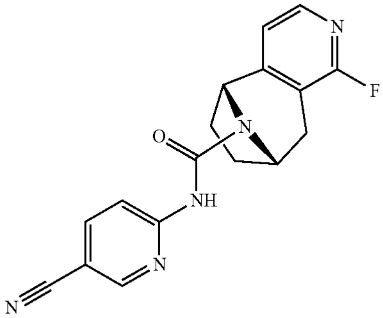
42
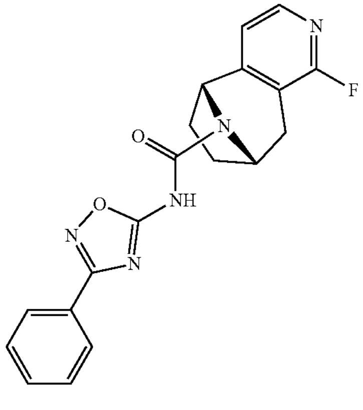
43
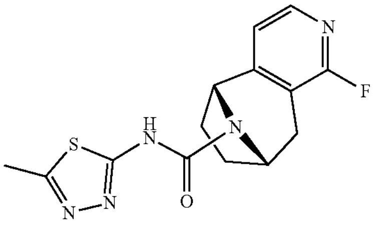
44
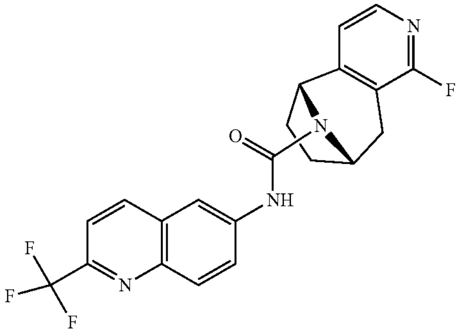
45
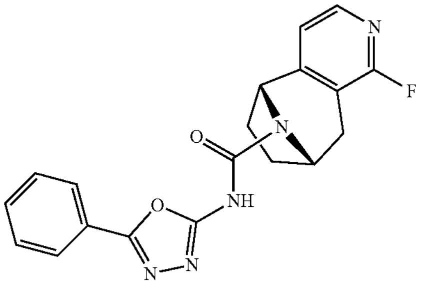
46
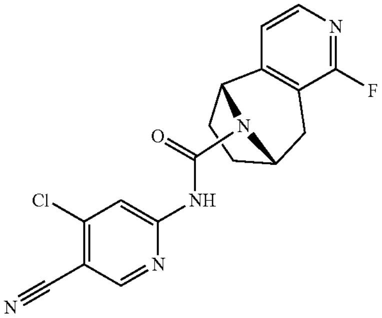
47
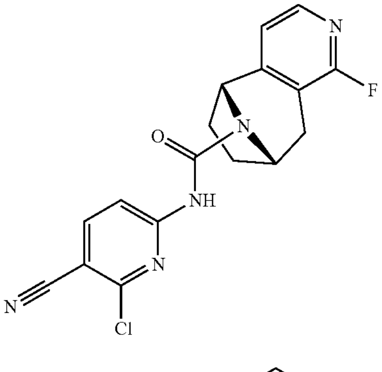
48
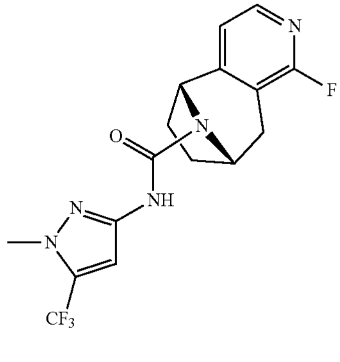

-continued

49

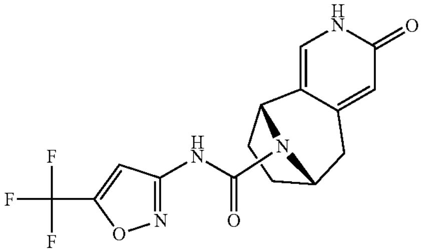

50

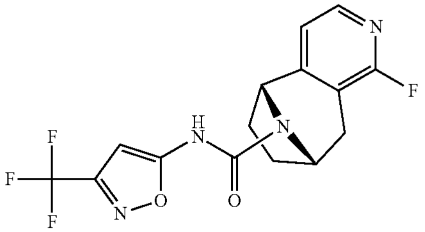

51

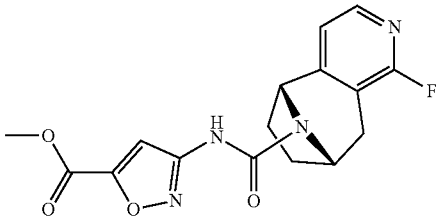

52

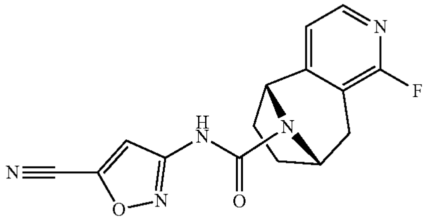

and enantiomers thereof, and mixtures of enantiomers thereof, including racemic mixtures, and pharmaceutically acceptable salts and solvates thereof.

In one preferred embodiment, the compound is selected from compounds 1-4, 8-26, 28-31, 33, 35-42 and 44-47, 49, 50, 51 and 52 above, and enantiomers thereof, and mixtures of enantiomers thereof, including racemic mixtures, and pharmaceutically acceptable salts and solvates thereof.

In an even more preferred embodiment, the compound is selected from compounds 1, 2, 4, 9, 10, 11, 13, 17, 19, 22, 23, 29, 30, 33, 36, 38, 40, 44, 46, 49, 50 and 52 above, and enantiomers thereof, and mixtures of enantiomers thereof, including racemic mixtures, and pharmaceutically acceptable salts and solvates thereof.

In one preferred embodiment, the compound is selected from the following:

(5R,8S)—N-(4-chloro-5-(trifluoromethyl)pyridin-2-yl)-1-fluoro-6,7,8,9-tetrahydro-5H-5,8-epiminocyclohepta[c]pyridine-10-carboxamide;

(5S,8R)—N-(4-chloro-5-(trifluoromethyl)pyridin-2-yl)-1-fluoro-6,7,8,9-tetrahydro-5H-5,8-epiminocyclohepta[c]pyridine-10-carboxamide;

(±)-N-(4-chloro-5-(trifluoromethyl)pyridin-2-yl)-1-fluoro-6,7,8,9-tetrahydro-5H-5,8-epiminocyclohepta[c]pyridine-10-carboxamide;

(5R,8S)—N-(4,5-dichloropyridin-2-yl)-1-fluoro-6,7,8,9-tetrahydro-5H-5,8-epiminocyclohepta[c]pyridine-10-carboxamide;

(5S,8R)—N-(4,5-dichloropyridin-2-yl)-1-fluoro-6,7,8,9-tetrahydro-5H-5,8-epiminocyclohepta[c]pyridine-10-carboxamide;

(±)-N-(4,5-dichloropyridin-2-yl)-1-fluoro-6,7,8,9-tetrahydro-5H-5,8-epiminocyclohepta[c]pyridine-10-carboxamide;

(5R,8S)—N-(5,6-dichloropyridin-2-yl)-1-fluoro-6,7,8,9-tetrahydro-5H-5,8-epiminocyclohepta[c]pyridine-10-carboxamide;

(5S,8R)—N-(5,6-dichloropyridin-2-yl)-1-fluoro-6,7,8,9-tetrahydro-5H-5,8-epiminocyclohepta[c]pyridine-10-carboxamide;

(±)-N-(5,6-dichloropyridin-2-yl)-1-fluoro-6,7,8,9-tetrahydro-5H-5,8-epiminocyclohepta[c]pyridine-10-carboxamide;

(6S,9R)—N-(4,5-dichloropyridin-2-yl)-3-oxo-3,5,6,7,8,9-hexahydro-2H-6,9-epiminocyclohepta[c]pyridine-10-carboxamide;

(6R,9S)—N-(4,5-dichloropyridin-2-yl)-3-oxo-3,5,6,7,8,9-hexahydro-2H-6,9-epiminocyclohepta[c]pyridine-10-carboxamide;

(±)-N-(4,5-dichloropyridin-2-yl)-3-oxo-3,5,6,7,8,9-hexahydro-2H-6,9-epiminocyclohepta[c]pyridine-10-carboxamide;

(6S,9R)—N-(5,6-dichloropyridin-2-yl)-3-oxo-3,5,6,7,8,9-hexahydro-2H-6,9-epiminocyclohepta[c]pyridine-10-carboxamide;

(6R,9S)—N-(5,6-dichloropyridin-2-yl)-3-oxo-3,5,6,7,8,9-hexahydro-2H-6,9-epiminocyclohepta[c]pyridine-10-carboxamide;

(±)-N-(5,6-dichloropyridin-2-yl)-3-oxo-3,5,6,7,8,9-hexahydro-2H-6,9-epiminocyclohepta[c]pyridine-10-carboxamide;

(5R,8S)—N-(5-(trifluoromethyl)pyrazin-2-yl)-6,7,8,9-tetrahydro-5H-5,8-epiminocyclohepta-[d]pyrimidine-10-carboxamide;

(5S,8R)—N-(5-(trifluoromethyl)pyrazin-2-yl)-6,7,8,9-tetrahydro-5H-5,8-epiminocyclohepta-[d]pyrimidine-10-carboxamide;

(±)-N-(5-(trifluoromethyl)pyrazin-2-yl)-6,7,8,9-tetrahydro-5H-5,8-epiminocyclohepta-[d]pyrimidine-10-carboxamide;

(5R,8S)-1-fluoro-N-(6-phenoxypyridin-3-yl)-6,7,8,9-tetrahydro-5H-5,8-epiminocyclohepta-[c]pyridine-10-carboxamide;

(5S,8R)-1-fluoro-N-(6-phenoxypyridin-3-yl)-6,7,8,9-tetrahydro-5H-5,8-epiminocyclohepta-[c]pyridine-10-carboxamide;

(±)-1-fluoro-N-(6-phenoxypyridin-3-yl)-6,7,8,9-tetrahydro-5H-5,8-epiminocyclohepta-[c]pyridine-10-carboxamide (5R,8S)—N-(5-chloropyridin-3-yl)-1-fluoro-6,7,8,9-tetrahydro-5H-5,8-epiminocyclohepta-[c]pyridine-10-carboxamide;

(5S,8R)—N-(5-chloropyridin-3-yl)-1-fluoro-6,7,8,9-tetrahydro-5H-5,8-epiminocyclohepta-[c]pyridine-10-carboxamide;

(±)-N-(5-chloropyridin-3-yl)-1-fluoro-6,7,8,9-tetrahydro-5H-5,8-epiminocyclohepta-[c]pyridine-10-carboxamide;

(6S,9R)-3-oxo-N-(2-(trifluoromethyl)quinolin-6-yl)-3,5,6,7,8,9-hexahydro-2H-6,9-epiminocyclohepta[c]pyridine-10-carboxamide;

(6R,9S)-3-oxo-N-(2-(trifluoromethyl)quinolin-6-yl)-3,5,6,7,8,9-hexahydro-2H-6,9-epiminocyclohepta[c]pyridine-10-carboxamide;

(±)-3-oxo-N-(2-(trifluoromethyl)quinolin-6-yl)-3,5,6,7,8,9-hexahydro-2H-6,9-epiminocyclohepta[c]pyridine-10-carboxamide;

(6S,9R)—N-(4,5-dichloropyridin-2-yl)-4-fluoro-3-oxo-3,5,6,7,8,9-hexahydro-2H-6,9-epiminocyclohepta[c]pyridine-10-carboxamide;

(6R,9S)—N-(4,5-dichloropyridin-2-yl)-4-fluoro-3-oxo-3,5,6,7,8,9-hexahydro-2H-6,9-epiminocyclohepta[c]pyridine-10-carboxamide;

(±)-N-(4,5-dichloropyridin-2-yl)-4-fluoro-3-oxo-3,5,6,7,8,9-hexahydro-2H-6,9-epiminocyclohepta[c]pyridine-10-carboxamide (5R,8S)—N-(5,6-dichloropyridin-3-yl)-1-fluoro-6,7,8,9-tetrahydro-5H-5,8-epiminocyclohepta[c]pyridine-10-carboxamide;

(5S,8R)—N-(5,6-dichloropyridin-3-yl)-1-fluoro-6,7,8,9-tetrahydro-5H-5,8-epiminocyclohepta[c]pyridine-10-carboxamide;

(±)-N-(5,6-dichloropyridin-3-yl)-1-fluoro-6,7,8,9-tetrahydro-5H-5,8-epiminocyclohepta-[c]pyridine-10-carboxamide;

(6S,9R)—N-(5,6-dichloropyridin-3-yl)-3-oxo-3,5,6,7,8,9-hexahydro-2H-6,9-epiminocyclohepta[c]pyridine-10-carboxamide;

(6R,9S)—N-(5,6-dichloropyridin-3-yl)-3-oxo-3,5,6,7,8,9-hexahydro-2H-6,9-epiminocyclohepta[c]pyridine-10-carboxamide;

(±)-N-(5,6-dichloropyridin-3-yl)-3-oxo-3,5,6,7,8,9-hexahydro-2H-6,9-epiminocyclohepta[c]pyridine-10-carboxamide;

(6S,9R)—N-(5-fluoro-2-(trifluoromethyl)pyridin-4-yl)-3-oxo-3,5,6,7,8,9-hexahydro-2H-6,9-epiminocyclohepta[c]pyridine-10-carboxamide;

(6R,9S)—N-(5-fluoro-2-(trifluoromethyl)pyridin-4-yl)-3-oxo-3,5,6,7,8,9-hexahydro-2H-6,9-epiminocyclohepta[c]pyridine-10-carboxamide;

(±)-N-(5-fluoro-2-(trifluoromethyl)pyridin-4-yl)-3-oxo-3,5,6,7,8,9-hexahydro-2H-6,9-epiminocyclohepta[c]pyridine-10-carboxamide;

(5R,8S)—N-(5-chloro-6-(2H-1,2,3-triazol-2-yl)pyridin-3-yl)-1-fluoro-6,7,8,9-tetrahydro-5H-5,8-epiminocyclohepta[c]pyridine-10-carboxamide;

(5S,8R)—N-(5-chloro-6-(2H-1,2,3-triazol-2-yl)pyridin-3-yl)-1-fluoro-6,7,8,9-tetrahydro-5H-5,8-epiminocyclohepta[c]pyridine-10-carboxamide;

(±)-N-(5-chloro-6-(2H-1,2,3-triazol-2-yl)pyridin-3-yl)-1-fluoro-6,7,8,9-tetrahydro-5H-5,8-epiminocyclohepta[c]pyridine-10-carboxamide;

(5R,8S)—N-(6-chloro-4-fluoropyridin-3-yl)-1-fluoro-6,7,8,9-tetrahydro-5H-5,8-epiminocyclohepta[c]pyridine-10-carboxamide;

(5S,8R)—N-(6-chloro-4-fluoropyridin-3-yl)-1-fluoro-6,7,8,9-tetrahydro-5H-5,8-epiminocyclohepta[c]pyridine-10-carboxamide;

(±)-N-(6-chloro-4-fluoropyridin-3-yl)-1-fluoro-6,7,8,9-tetrahydro-5H-5,8-epiminocyclohepta[c]pyridine-10-carboxamide;

(6S,9R)—N-(4-chloro-5-(trifluoromethyl)pyridin-2-yl)-3-oxo-3,5,6,7,8,9-hexahydro-2H-6,9-epiminocyclohepta[c]pyridine-10-carboxamide;

(6R,9S)—N-(4-chloro-5-(trifluoromethyl)pyridin-2-yl)-3-oxo-3,5,6,7,8,9-hexahydro-2H-6,9-epiminocyclohepta[c]pyridine-10-carboxamide;

(±)-N-(4-chloro-5-(trifluoromethyl)pyridin-2-yl)-3-oxo-3,5,6,7,8,9-hexahydro-2H-6,9-epiminocyclohepta[c]pyridine-10-carboxamide;

(5R,8S)-1-fluoro-N-(5-fluoro-2-(trifluoromethyl)pyridin-4-yl)-6,7,8,9-tetrahydro-5H-5,8-epiminocyclohepta[c]pyridine-10-carboxamide;

(5S,8R)-1-fluoro-N-(5-fluoro-2-(trifluoromethyl)pyridin-4-yl)-6,7,8,9-tetrahydro-5H-5,8-epiminocyclohepta[c]pyridine-10-carboxamide;

(±)-1-fluoro-N-(5-fluoro-2-(trifluoromethyl)pyridin-4-yl)-6,7,8,9-tetrahydro-5H-5,8-epiminocyclohepta[c]pyridine-10-carboxamide;

(5R,8S)-1-fluoro-N-(5-(trifluoromethyl)pyridin-2-yl)-6,7,8,9-tetrahydro-5H-5,8-epiminocyclohepta[c]pyridine-10-carboxamide;

(5S,8R)-1-fluoro-N-(5-(trifluoromethyl)pyridin-2-yl)-6,7,8,9-tetrahydro-5H-5,8-epiminocyclohepta[c]pyridine-10-carboxamide;

(±)-1-fluoro-N-(5-(trifluoromethyl)pyridin-2-yl)-6,7,8,9-tetrahydro-5H-5,8-epiminocyclohepta[c]pyridine-10-carboxamide;

(5R,8S)—N-(5,6-dichloro-3-fluoropyridin-2-yl)-1-fluoro-6,7,8,9-tetrahydro-5H-5,8-epiminocyclohepta[c]pyridine-10-carboxamide;

(5S,8R)—N-(5,6-dichloro-3-fluoropyridin-2-yl)-1-fluoro-6,7,8,9-tetrahydro-5H-5,8-epiminocyclohepta[c]pyridine-10-carboxamide;

(±)-N-(5,6-dichloro-3-fluoropyridin-2-yl)-1-fluoro-6,7,8,9-tetrahydro-5H-5,8-epiminocyclohepta[c]pyridine-10-carboxamide;

(5R,8S)-1-fluoro-N-(4-methyl-1,2,5-oxadiazol-3-yl)-6,7,8,9-tetrahydro-5H-5,8-epiminocyclohepta[c]pyridine-10-carboxamide;

(5S,8R)-1-fluoro-N-(4-methyl-1,2,5-oxadiazol-3-yl)-6,7,8,9-tetrahydro-5H-5,8-epiminocyclohepta[c]pyridine-10-carboxamide;

(±)-1-fluoro-N-(4-methyl-1,2,5-oxadiazol-3-yl)-6,7,8,9-tetrahydro-5H-5,8-epiminocyclohepta[c]pyridine-10-carboxamide;

(5R,8S)-1-fluoro-N-(5-phenyl-1,2,4-oxadiazol-3-yl)-6,7,8,9-tetrahydro-5H-5,8-epiminocyclohepta[c]pyridine-10-carboxamide;

(5S,8R)-1-fluoro-N-(5-phenyl-1,2,4-oxadiazol-3-yl)-6,7,8,9-tetrahydro-5H-5,8-epiminocyclohepta[c]pyridine-10-carboxamide;

(±)-1-fluoro-N-(5-phenyl-1,2,4-oxadiazol-3-yl)-6,7,8,9-tetrahydro-5H-5,8-epiminocyclohepta[c]pyridine-10-carboxamide;

(5R,8S)-1-fluoro-N-(5-(trifluoromethyl)-1,3,4-thiadiazol-2-yl)-6,7,8,9-tetrahydro-5H-5,8-epiminocyclohepta[c]pyridine-10-carboxamide;

(5S,8R)-1-fluoro-N-(5-(trifluoromethyl)-1,3,4-thiadiazol-2-yl)-6,7,8,9-tetrahydro-5H-5,8-epiminocyclohepta[c]pyridine-10-carboxamide;

(±)-1-fluoro-N-(5-(trifluoromethyl)-1,3,4-thiadiazol-2-yl)-6,7,8,9-tetrahydro-5H-5,8-epiminocyclohepta[c]pyridine-10-carboxamide;

(5R,8S)-1-fluoro-N-(5-(pyridin-4-yl)-1,3,4-thiadiazol-2-yl)-6,7,8,9-tetrahydro-5H-5,8-epiminocyclohepta[c]pyridine-10-carboxamide;

(5S,8R)-1-fluoro-N-(5-(pyridin-4-yl)-1,3,4-thiadiazol-2-yl)-6,7,8,9-tetrahydro-5H-5,8-epiminocyclohepta[c]pyridine-10-carboxamide;

(±)-1-fluoro-N-(5-(pyridin-4-yl)-1,3,4-thiadiazol-2-yl)-6,7,8,9-tetrahydro-5H-5,8-epiminocyclohepta[c]pyridine-10-carboxamide;

(5R,8S)-1-fluoro-N-(5-(trifluoromethyl)pyrimidin-2-yl)-6,7,8,9-tetrahydro-5H-5,8-epiminocyclohepta[c]pyridine-10-carboxamide;

(5S,8R)-1-fluoro-N-(5-(trifluoromethyl)pyrimidin-2-yl)-6,7,8,9-tetrahydro-5H-5,8-epiminocyclohepta[c]pyridine-10-carboxamide;

(±)-1-fluoro-N-(5-(trifluoromethyl)pyrimidin-2-yl)-6,7,8,9-tetrahydro-5H-5,8-epiminocyclohepta[c]pyridine-10-carboxamide;

(5R,8S)—N-(5-ethyl-1,3,4-thiadiazol-2-yl)-1-fluoro-6,7,8,9-tetrahydro-5H-5,8-epiminocyclohepta[c]pyridine-10-carboxamide;

(5S,8R)—N-(5-ethyl-1,3,4-thiadiazol-2-yl)-1-fluoro-6,7,8,9-tetrahydro-5H-5,8-epiminocyclohepta[c]pyridine-10-carboxamide;

(±)-N-(5-ethyl-1,3,4-thiadiazol-2-yl)-1-fluoro-6,7,8,9-tetrahydro-5H-5,8-epiminocyclohepta[c]pyridine-10-carboxamide;

(5R,8S)—N-(2-(difluoromethyl)-2H-pyrazolo[3,4-c]pyridin-5-yl)-1-fluoro-6,7,8,9-tetrahydro-5H-5,8-epiminocyclohepta[c]pyridine-10-carboxamide;

(5S,8R)—N-(2-(difluoromethyl)-2H-pyrazolo[3,4-c]pyridin-5-yl)-1-fluoro-6,7,8,9-tetrahydro-5H-5,8-epiminocyclohepta[c]pyridine-10-carboxamide;

(±)-N-(2-(difluoromethyl)-2H-pyrazolo[3,4-c]pyridin-5-yl)-1-fluoro-6,7,8,9-tetrahydro-5H-5,8-epiminocyclohepta[c]pyridine-10-carboxamide;

(5R,8S)—N-(4-chloro-5-(trifluoromethyl)pyridin-2-yl)-6,7,8,9-tetrahydro-5H-5,8-epiminocyclohepta[d]pyrimidine-10-carboxamide;

(5S,8R)—N-(4-chloro-5-(trifluoromethyl)pyridin-2-yl)-6,7,8,9-tetrahydro-5H-5,8-epiminocyclohepta[d]pyrimidine-10-carboxamide;

(±)-N-(4-chloro-5-(trifluoromethyl)pyridin-2-yl)-6,7,8,9-tetrahydro-5H-5,8-epiminocyclohepta[d]pyrimidine-10-carboxamide.

(5R,8S)-1-Fluoro-N-(2-phenylthiazol-5-yl)-6,7,8,9-tetrahydro-5H-5,8-epiminocyclohepta[c]pyridine-10-carboxamide (5S,8R)-1-Fluoro-N-(2-phenylthiazol-5-yl)-6,7,8,9-tetrahydro-5H-5,8-epiminocyclohepta[c]pyridine-10-carboxamide (±)-1-Fluoro-N-(2-phenylthiazol-5-yl)-6,7,8,9-tetrahydro-5H-5,8-epiminocyclohepta[c]pyridine-10-carboxamide (5R,8S)—N-(4,5-Dichlorothiazol-2-yl)-1-fluoro-6,7,8,9-tetrahydro-5H-5,8-epiminocyclohepta[c]pyridine-10-carboxamide (5S,8R)—N-(4,5-Dichlorothiazol-2-yl)-1-fluoro-6,7,8,9-tetrahydro-5H-5,8-epiminocyclohepta[c]pyridine-10-carboxamide (±)-N-(4,5-Dichlorothiazol-2-yl)-1-fluoro-6,7,8,9-tetrahydro-5H-5,8-epiminocyclohepta[c]pyridine-10-carboxamide (5R,8S)—N-(5-Cyclopropyl-1,3,4-thiadiazol-2-yl)-1-fluoro-6,7,8,9-tetrahydro-5H-5,8-epiminocyclohepta[c]pyridine-10-carboxamide (5S,8R)—N-(5-Cyclopropyl-1,3,4-thiadiazol-2-yl)-1-fluoro-6,7,8,9-tetrahydro-5H-5,8-epiminocyclohepta[c]pyridine-10-carboxamide (±)-N-(5-Cyclopropyl-1,3,4-thiadiazol-2-yl)-1-fluoro-6,7,8,9-tetrahydro-5H-5,8-epiminocyclohepta[c]pyridine-10-carboxamide (5R,8S)-1-Fluoro-N-(5-(tetrahydro-2H-pyran-4-yl)-1,3,4-thiadiazol-2-yl)-6,7,8,9-tetrahydro-5H-5,8-epiminocyclohepta[c]pyridine-10-carboxamide (5S,8R)-1-Fluoro-N-(5-(tetrahydro-2H-pyran-4-yl)-1,3,4-thiadiazol-2-yl)-6,7,8,9-tetrahydro-5H-5,8-epiminocyclohepta[c]pyridine-10-carboxamide (±)-1-Fluoro-N-(5-(tetrahydro-2H-pyran-4-yl)-1,3,4-thiadiazol-2-yl)-6,7,8,9-tetrahydro-5H-5,8-epiminocyclohepta[c]pyridine-10-carboxamide (5R,8S)-1-Fluoro-N-(5-phenyl-1,3,4-thiadiazol-2-yl)-6,7,8,9-tetrahydro-5H-5,8-epiminocyclohepta[c]pyridine-10-carboxamide (5S,8R)-1-Fluoro-N-(5-phenyl-1,3,4-thiadiazol-2-yl)-6,7,8,9-tetrahydro-5H-5,8-epiminocyclohepta[c]pyridine-10-carboxamide (±)-1-Fluoro-N-(5-phenyl-1,3,4-thiadiazol-2-yl)-6,7,8,9-tetrahydro-5H-5,8-epiminocyclohepta[c]pyridine-10-carboxamide (5R,8S)-1-Fluoro-N-(1-methyl-1H-indazol-3-yl)-6,7,8,9-tetrahydro-5H-5,8-epiminocyclohepta[c]pyridine-10-carboxamide (5S,8R)-1-Fluoro-N-(1-methyl-1H-indazol-3-yl)-6,7,8,9-tetrahydro-5H-5,8-epiminocyclohepta[c]pyridine-10-carboxamide (±)-1-Fluoro-N-(1-methyl-1H-indazol-3-yl)-6,7,8,9-tetrahydro-5H-5,8-epiminocyclohepta[c]pyridine-10-carboxamide (5R,8S)—N-(Benzo[c][1,2,5]oxadiazol-5-yl)-1-fluoro-6,7,8,9-tetrahydro-5H-5,8-epiminocyclohepta[c]pyridine-10-carboxamide (5S,8R)—N-(Benzo[c][1,2,5]oxadiazol-5-yl)-1-fluoro-6,7,8,9-tetrahydro-5H-5,8-epiminocyclohepta[c]pyridine-10-carboxamide (±)-N-(Benzo[c][1,2,5]oxadiazol-5-yl)-1-fluoro-6,7,8,9-tetrahydro-5H-5,8-epiminocyclohepta[c]pyridine-10-carboxamide (5R,8S)-1-Fluoro-N-(5-(trifluoromethyl)isoxazol-3-yl)-6,7,8,9-tetrahydro-5H-5,8-epiminocyclohepta[c]pyridine-10-carboxamide (5S,8R)-1-Fluoro-N-(5-(trifluoromethyl)isoxazol-3-yl)-6,7,8,9-tetrahydro-5H-5,8-epiminocyclohepta[c]pyridine-10-carboxamide (±)-1-Fluoro-N-(5-(trifluoromethyl)isoxazol-3-yl)-6,7,8,9-tetrahydro-5H-5,8-epiminocyclohepta[c]pyridine-10-carboxamide (5R,8S)—N-(5-Cyano-6-(trifluoromethyl)pyridin-2-yl)-1-fluoro-6,7,8,9-tetrahydro-5H-5,8-epiminocyclohepta[c]pyridine-10-carboxamide (5S,8R)—N-(5-Cyano-6-(trifluoromethyl)pyridin-2-yl)-1-fluoro-6,7,8,9-tetrahydro-5H-5,8-epiminocyclohepta[c]pyridine-10-carboxamide (±)-N-(5-Cyano-6-(trifluoromethyl)pyridin-2-yl)-1-fluoro-6,7,8,9-tetrahydro-5H-5,8-epiminocyclohepta[c]pyridine-10-carboxamide (5R,8S)—N-(5-Cyano-3-(trifluoromethyl)pyridin-2-yl)-1-fluoro-6,7,8,9-tetrahydro-5H-5,8-epiminocyclohepta[c]pyridine-10-carboxamide (5S,8R)—N-(5-Cyano-3-(trifluoromethyl)pyridin-2-yl)-1-fluoro-6,7,8,9-tetrahydro-5H-5,8-epiminocyclohepta[c]pyridine-10-carboxamide (±)-N-(5-Cyano-3-(trifluoromethyl)pyridin-2-yl)-1-fluoro-6,7,8,9-tetrahydro-5H-5,8-epiminocyclohepta[c]pyridine-10-carboxamide (5R,8S)—N-(5-(Difluoromethoxy)pyridin-2-yl)-1-fluoro-6,7,8,9-tetrahydro-5H-5,8-epiminocyclohepta[c]pyridine-10-carboxamide (5S,8R)—N-(5-(Difluoromethoxy)pyridin-2-yl)-1-fluoro-6,7,8,9-tetrahydro-5H-5,8-epiminocyclohepta[c]pyridine-10-carboxamide (±)-N-(5-(Difluoromethoxy)pyridin-2-yl)-1-fluoro-6,7,8,9-tetrahydro-5H-5,8-epiminocyclohepta[c]pyridine-10-carboxamide (5R,8S)-1-Fluoro-N-(5-(trifluoromethoxy)pyridin-2-yl)-6,7,8,9-tetrahydro-5H-5,8-epiminocyclohepta[c]pyridine-10-carboxamide (5S,8R)-1-Fluoro-N-(5-(trifluoromethoxy)pyridin-2-yl)-6,7,8,9-tetrahydro-5H-5,8-epiminocyclohepta[c]pyridine-10-carboxamide (±)-1-Fluoro-N-(5-(trifluoromethoxy)pyridin-2-yl)-6,7,8,9-tetrahydro-5H-5,8-epiminocyclohepta[c]pyridine-10-carboxamide (5R,8S)—N-(5-Cyanopyridin-2-yl)-1-fluoro-6,7,8,9-tetrahydro-5H-5,8-epiminocyclohepta[c]pyridine-10-carboxamide (5S,8R)—N-(5-Cyanopyridin-2-yl)-1-fluoro-6,7,8,9-tetrahydro-5H-5,8-epiminocyclohepta[c]pyridine-10-carboxamide (±)-N-(5-Cyanopyridin-2-yl)-1-fluoro-6,7,8,9-tetrahydro-5H-5,8-epiminocyclohepta[c]pyridine-10-carboxamide (5R,8S)-1-Fluoro-N-(3-phenyl-1,2,4-oxadiazol-5-yl)-6,7,8,9-tetrahydro-5H-5,8-epiminocyclohepta[c]pyridine-10-carboxamide (5S,8R)-1-Fluoro-N-(3-phenyl-1,2,4-oxadiazol-5-yl)-6,7,8,9-tetrahydro-5H-5,8-epiminocyclohepta[c]pyridine-10-carboxamide (±)-1-Fluoro-N-(3-phenyl-1,2,4-oxadiazol-5-yl)-6,7,8,9-tetrahydro-5H-5,8-epiminocyclohepta[c]pyridine-10-carboxamide (5R,8S)-1-Fluoro-N-(5-methyl-1,3,4-thiadiazol-2-yl)-6,7,8,9-tetrahydro-5H-5,8-epiminocyclohepta[c]pyridine-10-carboxamide (5S,8R)-1-Fluoro-N-(5-methyl-1,3,4-thiadiazol-2-yl)-6,7,8,9-tetrahydro-5H-5,8-epiminocyclohepta[c]pyridine-10-carboxamide (±)-1-Fluoro-N-(5-methyl-1,3,4-thiadiazol-2-yl)-6,7,8,9-tetrahydro-5H-5,8-epiminocyclohepta[c]pyridine-10-carboxamide (5R,8S)-1-Fluoro-N-(2-(trifluoromethyl)quinolin-6-yl)-6,7,8,9-tetrahydro-5H-5,8-epiminocyclohepta[c]pyridine-10-carboxamide (5S,8R)-1-Fluoro-N-(2-(trifluoromethyl)quinolin-6-yl)-6,7,8,9-tetrahydro-5H-5,8-epiminocyclohepta[c]pyridine-10-carboxamide (±)-1-Fluoro-N-(2-(trifluoromethyl)quinolin-6-yl)-6,7,8,9-tetrahydro-5H-5,8-epiminocyclohepta[c]pyridine-10-carboxamide (5R,8S)-1-Fluoro-N-(5-phenyl-1,3,4-oxadiazol-2-yl)-6,7,8,9-tetrahydro-5H-5,8-epiminocyclohepta[c]pyridine-10-carboxamide (5S,8R)-1-Fluoro-N-(5-phenyl-1,3,4-oxadiazol-2-yl)-6,7,8,9-tetrahydro-5H-5,8-epiminocyclohepta[c]pyridine-10-carboxamide (±)-1-Fluoro-N-(5-phenyl-1,3,4-oxadiazol-2-yl)-6,7,8,9-tetrahydro-5H-5,8-epiminocyclohepta[c]pyridine-10-carboxamide (5R,8S)—N-(4-Chloro-5-cyanopyridin-2-yl)-1-fluoro-6,7,8,9-tetrahydro-5H-5,8-epiminocyclohepta[c]pyridine-10-carboxamide (5S,8R)—N-(4-Chloro-5-cyanopyridin-2-yl)-1-fluoro-6,7,8,9-tetrahydro-5H-5,8-epiminocyclohepta[c]pyridine-10-carboxamide (±)-N-(4-Chloro-5-cyanopyridin-2-yl)-1-fluoro-6,7,8,9-tetrahydro-5H-5,8-epiminocyclohepta[c]pyridine-10-carboxamide (5R,8S)—N-(6-Chloro-5-cyanopyridin-2-yl)-1-fluoro-6,7,8,9-tetrahydro-5H-5,8-epiminocyclohepta[c]pyridine-10-carboxamide (5S,8R)—N-(6-Chloro-5-cyanopyridin-2-yl)-1-fluoro-6,7,8,9-tetrahydro-5H-5,8-epiminocyclohepta[c]pyridine-10-carboxamide (±)-N-(6-Chloro-5-cyanopyridin-2-yl)-1-fluoro-6,7,8,9-tetrahydro-5H-5,8-epiminocyclohepta[c]pyridine-10-carboxamide (5R,8S)-1-fluoro-N-(1-methyl-5-(trifluoromethyl)-1H-pyrazol-3-yl)-6,7,8,9-tetrahydro-5H-5,8-epiminocyclohepta[c]pyridine-10-carboxamide (5S,8R)-1-fluoro-N-(1-methyl-5-(trifluoromethyl)-1H-pyrazol-3-yl)-6,7,8,9-tetrahydro-5H-5,8-epiminocyclohepta[c]pyridine-10-carboxamide (±)-1-fluoro-N-(1-methyl-5-(trifluoromethyl)-1H-pyrazol-3-yl)-6,7,8,9-tetrahydro-5H-5,8-epiminocyclohepta[c]pyridine-10-carboxamide (6S,9R)-3-oxo-N-(5-(trifluoromethyl)isoxazol-3-yl)-3,5,6,7,8,9-hexahydro-2H-6,9-epiminocyclohepta[c]pyridine-10-carboxamide (6R,9S)-3-oxo-N-(5-(trifluoromethyl)isoxazol-3-yl)-3,5,6,7,8,9-hexahydro-2H-6,9-epiminocyclohepta[c]pyridine-10-carboxamide (±)-3-oxo-N-(5-(trifluoromethyl)isoxazol-3-yl)-3,5,6,7,8,9-hexahydro-2H-6,9-epiminocyclohepta[c]pyridine-10-carboxamide (5R,8S)-1-fluoro-N-(3-(trifluoromethyl)isoxazol-5-yl)-6,7,8,9-tetrahydro-5H-5,8-epiminocyclohepta[c]pyridine-10-carboxamide (5S,8R)-1-fluoro-N-(3-(trifluoromethyl)isoxazol-5-yl)-6,7,8,9-tetrahydro-5H-5,8-epiminocyclohepta[c]pyridine-10-carboxamide (±)-1-fluoro-N-(3-(trifluoromethyl)isoxazol-5-yl)-6,7,8,9-tetrahydro-5H-5,8-epiminocyclohepta[c]pyridine-10-carboxamide methyl-3-((5R,8S)-1-fluoro-6,7,8,9-tetrahydro-5H-5,8-epiminocyclohepta[c]pyridine-10-carboxamido)isoxazole-5-carboxylate methyl-3-((5S,8R)-1-fluoro-6,7,8,9-tetrahydro-5H-5,8-epiminocyclohepta[c]pyridine-10-carboxamido)isoxazole-5-carboxylate methyl-3-((±)-1-fluoro-6,7,8,9-tetrahydro-5H-5,8-epiminocyclohepta[c]pyridine-10-carboxamido)isoxazole-5-carboxylate (5R,8S)—N-(5-cyanoisoxazol-3-yl)-1-fluoro-6,7,8,9-tetrahydro-5H-5,8-epiminocyclohepta[c]pyridine-10-carboxamide (5S,8R)—N-(5-cyanoisoxazol-3-yl)-1-fluoro-6,7,8,9-tetrahydro-5H-5,8-epiminocyclohepta[c]pyridine-10-carboxamide (±)-N-(5-cyanoisoxazol-3-yl)-1-fluoro-6,7,8,9-tetrahydro-5H-5,8-epiminocyclohepta[c]pyridine-10-carboxamide and pharmaceutically acceptable salts and solvates thereof.

In one highly preferred embodiment, the compound is selected from the following:

| | |
|---|---|
| 1 | (5R,8S)-N-(4-chloro-5-(trifluoromethyl)pyridin-2-yl)-1-fluoro-6,7,8,9-tetrahydro-5H-5,8-epiminocyclohepta[c]pyridine-10-carboxamide |
| 2 | (5R,8S)-N-(4,5-dichloropyridin-2-yl)-1-fluoro-6,7,8,9-tetrahydro-5H-5,8-epiminocyclohepta[c]pyridine-10-carboxamide |
| 3 | (5R,8S)-N-(5,6-dichloropyridin-2-yl)-1-fluoro-6,7,8,9-tetrahydro-5H-5,8-epiminocyclohepta[c]pyridine-10-carboxamide |
| 4 | (6S,9R)-N-(4,5-dichloropyridin-2-yl)-3-oxo-3,5,6,7,8,9-hexahydro-2H-6,9-epiminocyclo-hepta[c]pyridine-10-carboxamide |

-continued

| | |
|---|---|
| 5 | (6S,9R)-N-(5,6-dichloropyridin-2-yl)-3-oxo-3,5,6,7,8,9-hexahydro-2H-6,9-epiminocyclo-hepta[c]pyridine-10-carboxamide |
| 6 | (±)-N-(5-(trifluoromethyl)pyrazin-2-yl)-6,7,8,9-tetrahydro-5H-5,8-epiminocyclohepta-[d]pyrimidine-10-carboxamide |
| 8 | (±)-1-fluoro-N-(6-phenoxypyridin-3-yl)-6,7,8,9-tetrahydro-5H-5,8-epiminocyclohepta-[c]pyridine-10-carboxamide |
| 9 | (±)-N-(5-chloropyridin-3-yl)-1-fluoro-6,7,8,9-tetrahydro-5H-5,8-epiminocyclohepta-[c]pyridine-10-carboxamide |
| 10 | (6S,9R)-3-oxo-N-(2-(trifluoromethyl)quinolin-6-yl)-3,5,6,7,8,9-hexahydro-2H-6,9-epiminocyclohepta[c]pyridine-10-carboxamide |
| 11 | (±)-N-(4,5-dichloropyridin-2-yl)-4-fluoro-3-oxo-3,5,6,7,8,9-hexahydro-2H-6,9-epiminocyclohepta[c]pyridine-10-carboxamide |
| 12 | (5R,8S)-N-(5,6-dichloropyridin-3-yl)-1-fluoro-6,7,8,9-tetrahydro-5H-5,8-epiminocyclo-hepta[c]pyridine-10-carboxamide |
| 13 | (6S,9R)-N-(5,6-dichloropyridin-3-yl)-3-oxo-3,5,6,7,8,9-hexahydro-2H-6,9-epiminocyclo-hepta[c]pyridine-10-carboxamide |
| 14 | (6S,9R)-N-(5-fluoro-2-(trifluoromethyl)pyridin-4-yl)-3-oxo-3,5,6,7,8,9-hexahydro-2H-6,9-epiminocyclohepta[c]pyridine-10-carboxamide |
| 15 | (5R,8S)-N-(5-chloro-6-(2H-1,2,3-triazol-2-yl)pyridin-3-yl)-1-fluoro-6,7,8,9-tetrahydro-5H-5,8-epiminocyclohepta[c]pyridine-10-carboxamide |
| 16 | (5R,8S)-N-(6-chloro-4-fluoropyridin-3-yl)-1-fluoro-6,7,8,9-tetrahydro-5H-5,8-epimino-cyclohepta[c]pyridine-10-carboxamide |
| 17 | (6S,9R)-N-(4-chloro-5-(trifluoromethyl)pyridin-2-yl)-3-oxo-3,5,6,7,8,9-hexahydro-2H-6,9-epiminocyclohepta[c]pyridine-10-carboxamide |
| 18 | (5R,8S)-1-fluoro-N-(5-fluoro-2-(trifluoromethyl)pyridin-4-yl)-6,7,8,9-tetrahydro-5H-5,8-epiminocyclohepta[c]pyridine-10-carboxamide |
| 19 | (5R,8S)-1-fluoro-N-(5-(trifluoromethyl)pyridin-2-yl)-6,7,8,9-tetrahydro-5H-5,8-epimino-cyclohepta[c]pyridine-10-carboxamide |
| 20 | (5R,8S)-N-(5,6-dichloro-3-fluoropyridin-2-yl)-1-fluoro-6,7,8,9-tetrahydro-5H-5,8-epiminocyclohepta[c]pyridine-10-carboxamide |
| 21 | (5R,8S)-1-fluoro-N-(4-methyl-1,2,5-oxadiazol-3-yl)-6,7,8,9-tetrahydro-5H-5,8-epiminocyclohepta[c]pyridine-10-carboxamide |
| 22 | (5R,8S)-1-fluoro-N-(5-phenyl-1,2,4-oxadiazol-3-yl)-6,7,8,9-tetrahydro-5H-5,8-epiminocyclohepta[c]pyridine-10-carboxamide |
| 23 | (5R,8S)-1-fluoro-N-(5-(trifluoromethyl)-1,3,4-thiadiazol-2-yl)-6,7,8,9-tetrahydro-5H-5,8-epiminocyclohepta[c]pyridine-10-carboxamide |
| 24 | (5R,8S)-1-fluoro-N-(5-(pyridin-4-yl)-1,3,4-thiadiazol-2-yl)-6,7,8,9-tetrahydro-5H-5,8-epiminocyclohepta[c]pyridine-10-carboxamide |
| 25 | (5R,8S)-1-fluoro-N-(5-(trifluoromethyl)pyrimidin-2-yl)-6,7,8,9-tetrahydro-5H-5,8-epiminocyclohepta[c]pyridine-10-carboxamide |
| 26 | (5R,8S)-N-(5-ethyl-1,3,4-thiadiazol-2-yl)-1-fluoro-6,7,8,9-tetrahydro-5H-5,8-epimino-cyclohepta[c]pyridine-10-carboxamide |
| 27 | (5R,8S)-N-(2-(difluoromethyl)-2H-pyrazolo[3,4-c]pyridin-5-yl)-1-fluoro-6,7,8,9-tetrahydro-5H-5,8-epiminocyclohepta[c]pyridine-10-carboxamide |
| 28 | (±)-N-(4-chloro-5-(trifluoromethyl)pyridin-2-yl)-6,7,8,9-tetrahydro-5H-5,8-epiminocyclo-hepta[d]pyrimidine-10-carboxamide |
| 29 | (5R,8S)-1-Fluoro-N-(2-phenylthiazol-5-yl)-6,7,8,9-tetrahydro-5H-5,8-epiminocyclohepta[c]pyridine-10-carboxamide |
| 30 | (5R,8S)-N-(4,5-Dichlorothiazol-2-yl)-1-fluoro-6,7,8,9-tetrahydro-5H-5,8-epiminocyclohepta[c]pyridine-10-carboxamide |
| 31 | (5R,8S)-N-(5-Cyclopropyl-1,3,4-thiadiazol-2-yl)-1-fluoro-6,7,8,9-tetrahydro-5H-5,8-epiminocyclohepta[c]pyridine-10-carboxamide |
| 32 | (5R,8S)-1-Fluoro-N-(5-(tetrahydro-2H-pyran-4-yl)-1,3,4-thiadiazol-2-yl)-6,7,8,9-tetrahydro-5H-5,8-epiminocyclohepta[c]pyridine-10-carboxamide |
| 33 | (5R,8S)-1-Fluoro-N-(5-phenyl-1,3,4-thiadiazol-2-yl)-6,7,8,9-tetrahydro-5H-5,8-epiminocyclohepta[c]pyridine-10-carboxamide |
| 34 | (5R,8S)-1-Fluoro-N-(1-methyl-1H-indazol-3-yl)-6,7,8,9-tetrahydro-5H-5,8-epiminocyclohepta[c]pyridine-10-carboxamide |
| 35 | (5R,8S)-N-(Benzo[c][1,2,5]oxadiazol-5-yl)-1-fluoro-6,7,8,9-tetrahydro-5H-5,8-epiminocyclohepta[c]pyridine-10-carboxamide |
| 36 | (5R,8S)-1-Fluoro-N-(5-(trifluoromethyl)isoxazol-3-yl)-6,7,8,9-tetrahydro-5H-5,8-epiminocyclohepta[c]pyridine-10-carboxamide |
| 37 | (5R,8S)-N-(5-Cyano-6-(trifluoromethyl)pyridin-2-yl)-1-fluoro-6,7,8,9-tetrahydro-5H-5,8-epiminocyclohepta[c]pyridine-10-carboxamide |
| 38 | (5R,8S)-N-(5-Cyano-3-(trifluoromethyl)pyridin-2-yl)-1-fluoro-6,7,8,9-tetrahydro-5H-5,8-epiminocyclohepta[c]pyridine-10-carboxamide |
| 39 | (5R,8S)-N-(5-(Difluoromethoxy)pyridin-2-yl)-1-fluoro-6,7,8,9-tetrahydro-5H-5,8-epiminocyclohepta[c]pyridine-10-carboxamide |
| 40 | (5R,8S)-1-Fluoro-N-(5-(trifluoromethoxy)pyridin-2-yl)-6,7,8,9-tetrahydro-5H-5,8-epiminocyclohepta[c]pyridine-10-carboxamide |
| 41 | (5R,8S)-N-(5-Cyanopyridin-2-yl)-1-fluoro-6,7,8,9-tetrahydro-5H-5,8-epiminocyclohepta[c]pyridine-10-carboxamide |
| 42 | (5R,8S)-1-Fluoro-N-(3-phenyl-1,2,4-oxadiazol-5-yl)-6,7,8,9-tetrahydro-5H-5,8-epiminocyclohepta[c]pyridine-10-carboxamide |
| 43 | (5R,8S)-1-Fluoro-N-(5-methyl-1,3,4-thiadiazol-2-yl)-6,7,8,9-tetrahydro-5H-5,8-epiminocyclohepta[c]pyridine-10-carboxamide |
| 44 | (5R,8S)-1-Fluoro-N-(2-(trifluoromethyl)quinolin-6-yl)-6,7,8,9-tetrahydro-5H-5,8-epiminocyclohepta[c]pyridine-10-carboxamide |

-continued

| | |
|---|---|
| 45 | (5R,8S)-1-Fluoro-N-(5-phenyl-1,3,4-oxadiazol-2-yl)-6,7,8,9-tetrahydro-5H-5,8-epiminocyclohepta[c]pyridine-10-carboxamide |
| 46 | (5R,8S)-N-(4-Chloro-5-cyanopyridin-2-yl)-1-fluoro-6,7,8,9-tetrahydro-5H-5,8-epiminocyclohepta[c]pyridine-10-carboxamide |
| 47 | (5R,8S)-N-(6-Chloro-5-cyanopyridin-2-yl)-1-fluoro-6,7,8,9-tetrahydro-5H-5,8-epiminocyclohepta[c]pyridine-10-carboxamide |
| 48 | (5R,8S)-1-fluoro-N-(1-methyl-5-(trifluoromethyl)-1H-pyrazol-3-yl)-6,7,8,9-tetrahydro-5H-5,8-epiminocyclohepta[c]pyridine-10-carboxamide |
| 49 | (6S,9R)-3-oxo-N-(5-(trifluoromethyl)isoxazol-3-yl)-3,5,6,7,8,9-hexahydro-2H-6,9-epiminocyclohepta[c]pyridine-10-carboxamide |
| 50 | (5R,8S)-1-fluoro-N-(3-(trifluoromethyl)isoxazol-5-yl)-6,7,8,9-tetrahydro-5H-5,8-epiminocyclohepta[c]pyridine-10-carboxamide |
| 51 | methyl-3-((5R,8S)-1-fluoro-6,7,8,9-tetrahydro-5H-5,8-epiminocyclohepta[c]pyridine-10-carboxamido)isoxazole-5-carboxylate |
| 52 | (5R,8S)-N-(5-cyanoisoxazol-3-yl)-1-fluoro-6,7,8,9-tetrahydro-5H-5,8-epiminocyclohepta[c]pyridine-10-carboxamide |

and pharmaceutically acceptable salts and solvates thereof.

Process

A further aspect of the invention relates to a process for preparing a compound as defined herein, said process comprising reacting a compound of formula (III) with a compound of formula (II), where Y, $R_a$, $R_b$, B, A are as defined above, to form a compound of formula (I).

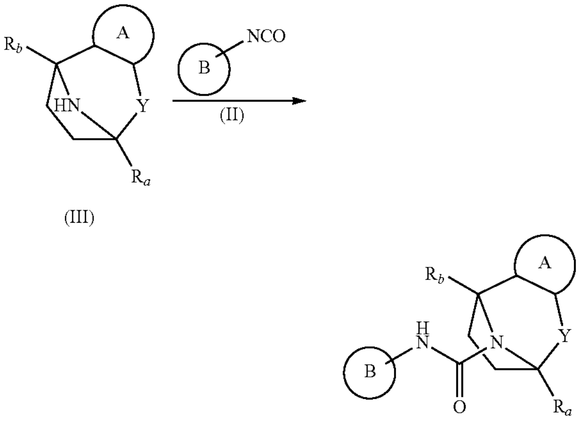

(III) (II) (I)

The isocyanate (11) can be generated in situ from the corresponding amine, (IIa):

(IIa)

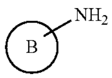

In one preferred embodiment, the reaction takes place in the presence of triphosgene and a base, preferably, N,N-diisopropylethylamine (DIPEA) or triethylamine. Preferably, the reaction takes place in an organic solvent. Suitable organic solvents include, but are not limited to, dichloromethane, tetrahydrofuran and dimethylformamide, or mixtures of two or more thereof. The skilled person would understand that other bases and solvents would also be suitable.

A further aspect of the invention relates to a process for preparing a compound as defined herein, said process comprising reacting a compound of formula (III) with 4-nitrophenyl carbonochloridate to form a compound of formula (IV), and then reacting said compound of formula (IV) with an amine (V) to form a compound of formula (I), where Y, $R_a$, $R_b$, B and A are as defined above:

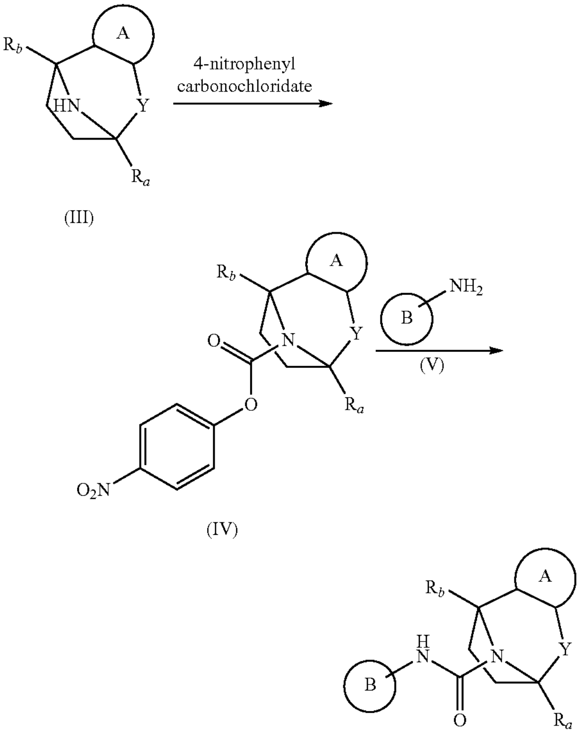

(III) (IV) (V) (I)

Therapeutic Applications

A further aspect of the invention relates to compounds as described herein for use in medicine. The compounds have particular use in the fields of oncology, immuno-oncology, and immunology as described in more detail below. In a preferred embodiment, the compound of the invention modulates GPR65, and more preferably inhibits GPR65 signalling.

Yet another aspect of the invention relates to compounds as described herein for use as a medicament, preferably for use in treating or preventing a disorder selected from a proliferative disorder and an immune disorder.

Another aspect of the invention relates to compounds as described herein for use in treating or preventing asthma and/or chronic obstructive pulmonary disease (COPD). GPR65 variant/SNP (rs6574978) has been shown to be associated with asthma/COPD syndrome with almost GWAS significant p value (1.18x10e-7) (Hardin, 2014). Furthermore, GPR65 activation by pH (pH is low/acidic in asthmatic lungs) promotes eosinophil viability in a cAMP-dependent manner, contributing to disease progression/exacerbation. It is further known that GPR65 KO mice have attenuated asthma symptoms (Kottyan, 2009).

Another aspect of the invention relates to compounds as described herein for use in treating or preventing acute respiratory distress syndrome (ARDS). GPR65 has been shown to be protective in a model of LPS-induced acute lung injury model (Tsurumaki, 2015).

One aspect of the invention relates to a compound as described herein for use in treating a proliferative disorder. Preferably, the proliferative disorder is a cancer or leukemia.

In one preferred embodiment, the cancer is a solid tumour and/or metastases thereof.

In another preferred embodiment, the cancer is selected from melanoma, renal cell carcinoma (RCC), gastric cancer, acute myeloid leukaemia (AML), triple negative breast cancer (TNBC), head and neck cancer, colorectal cancer, colorectal adenocarcinoma, pancreatic adenocarcinoma, sarcoma, lung cancer, ovarian cancer, gliomas, preferably glioblastoma (GBM).

Without wishing to be bound by theory, it is understood that GPR65 modulators are capable of preventing the increase in cytoplasmic cAMP in tumour-associated macrophages (TAMs) that would typically result from their exposure to the acidic tumour microenvironment and concomitant GPR65 activation. This reduction in the level of cytoplasmic cAMP in turn reduces the levels of ICER and TNFα, preventing the polarization of TAMs that are associated with non-inflammatory and tumour-permissive environment. Therefore, GPR65 modulators are expected to result in an increase in the visibility of the tumour to the immune system leading to increased immune-mediated tumour clearance. This suggests that modulation of GPR65 activity could be an effective treatment for cancer as standalone therapy or in combination with cancer immunotherapies (vaccines, agents that promote T cell mediated immune responses) or in patients that do not respond to immunomodulatory approaches such as PD1/PDL-1 blockade.

Another aspect of the invention relates to a compound as described herein for use in treating or preventing an immune disorder, preferably an autoimmune disease.

In one embodiment, the autoimmune disease is selected from psoriasis, psoriatic arthritis, rheumatoid arthritis (RA), multiple sclerosis (MS), systemic lupus erythematosus (SLE), autoimmune thyroiditis (Hashimoto's thyroiditis), Graves' disease, uveitis (including intermediate uveitis), ulcerative colitis, Crohn's disease, autoimmune uveoretinitis, systemic vasculitis, polymyositis-dermatomyositis, systemic sclerosis (scleroderma), Sjogren's Syndrome, ankylosing spondylitis and related spondyloarthropathies, sarcoidosis, autoimmune hemolytic anemia, immunological platelet disorders, autoimmune polyendocrinopathies, autoimmune myocarditis, type I diabetes and atopic dermatitis.

In a particularly preferred embodiment, the autoimmune disease is selected from psoriasis, psoriatic arthritis, ankylosing spondylitis, Crohn's disease, and multiple sclerosis (MS).

Without wishing to be bound by theory, it is understood that GPR65 modulators will prevent the upregulation of ICER in CD4+ T cells. This, in turn, is expected to prevent the ICER-associated suppression of IL-2 that biases CD4+ T cells toward the inflammatory Th17 phenotype associated with increased pathogenicity in the context of autoimmune disease. This is supported by the fact that mutations in the GPR65 locus are associated with several autoimmune diseases, such as multiple sclerosis, ankylosing spondylitis, inflammatory bowel disease, and Crohn's disease (Gaublomme, 2015). This suggests that modulation of GPR65 activity could be an effective treatment for autoimmune diseases.

Another aspect relates to a compound as described herein for use in treating or preventing a disorder caused by, associated with or accompanied by abnormal activity against GPR65.

Another aspect relates to a compound as described herein for use in treating or preventing a GPR65-associated disease or disorder.

Another aspect of the invention relates to a method of treating a disorder as described above comprising administering a compound as described herein to a subject.

Another aspect of the invention relates to a method of treating a GPR65-associated disease or disorder in a subject. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a subject having a disease state alleviated by modulation of GPR65 wherein the method comprises administering to the subject a therapeutically effective amount of a compound according to the invention.

Another aspect relates to a method of treating a disease state alleviated by modulation of GPR65, wherein the method comprises administering to a subject a therapeutically effective amount of a compound according to the invention.

Preferably, the subject is a mammal, more preferably a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately to determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$.

Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/day, commonly from about 100-1000 mg/day, preferably from about 150-700 mg/day and most preferably from about 250-500 mg/day or from 50-100 mg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "GPR65-related disease or disorder" refers to a disease or disorder characterized by inappropriate GPR65 activity. Inappropriate GPR65 activity refers to either an increase or decrease in GPR65 activity as measured by enzyme or cellular assays, for example, compared to the activity in a healthy subject. Inappropriate activity could also be due to overexpression of GPR65 in diseased tissue compared with healthy adjacent tissue.

Preferred diseases or disorders that the compounds described herein may be useful in preventing include proliferative disorders and immune disorders as described hereinbefore, as well as asthma and chronic obstructive pulmonary disease.

Thus, the present invention further provides use of compounds as defined herein in the preparation of a medicament for the treatment of a disease where it is desirable to modulate GPR65. Such diseases include proliferative disorders and immune disorders as described hereinbefore, as well as asthma and chronic obstructive pulmonary disease.

As used herein the phrase "preparation of a medicament" includes the use of the components of the invention directly as the medicament in addition to their use in any stage of the preparation of such a medicament.

In one preferred embodiment, the compound prevents the increase in cytoplasmic cAMP levels expected following GPR65 activation at acidic pH. This prevention of cAMP accumulation in turn prevents downstream signalling through ICER, as described above.

The "Human GPR65 cyclic adenosine monophosphate (cAMP) Homogeneous Time Resolved Fluorescence (HTRF) antagonist assay", or simply "cAMP assay", as described below, can be used to measure the potency of GPR65 modulators, which is expressed as the concentration of compound required to reduce the increase in cAMP concentration upon GPR65 activation by 50% (i.e. an $IC_{50}$).

In one preferred embodiment, the compound exhibits an $IC_{50}$ value in the cAMP assay of less than about 25 μM. More preferably, the compound exhibits an $IC_{50}$ value in the cAMP assay of less than about 10 μM, more preferably, less than about 5 μM, even more preferably, less than about 1 μM, even more preferably, less than about 0.1 μM.

In another preferred embodiment, the compound exhibits an hGPR65 IC50 value of less than 5 μM, more preferably less than 500 nM in the aforementioned assay.

Pharmaceutical Compositions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers, excipients or diluents therefor and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and PJ Weller. The carrier, or, if more than one is present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet.

Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound as described herein into conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3$^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Atropisomers

Some of the compounds of the invention may exist as atropisomers. Atropisomers are stereoisomers arising because of hindered rotation about a single bond, where energy differences due to steric strain or other contributors create a barrier to rotation that is high enough to allow for isolation of individual conformers. The invention encompasses all such atropisomers.

Prodrugs

The invention further includes the compounds of the present invention in prodrug form, i.e. covalently bonded compounds which release the active parent drug in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms. Preferably, the solvate is a hydrate.

Combinations

A further aspect of the invention relates to a combination comprising a compound as described herein and one or more additional active agents. In a particularly preferred embodiment, the one or more compounds of the invention are administered in combination with one or more additional active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

In the context of cancer, compounds of the invention can be used in combination with immunotherapies such as cancer vaccines and/or with other immune-modulators such as agents that block the PD1/PDL-1 interaction. Thus, in one preferred embodiment, the additional active agent is an immunotherapy agent, more preferably a cancer immunotherapy agent. An "immunotherapy agent" refers to a treatment that uses the subject's own immune system to fight diseases such as cancer. For other disorders the compounds of the invention can be used in combination agents that block or decrease inflammation such as antibodies that target pro-inflammatory cytokines.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The dosage amount will further be modified according to the mode of administration of the compound. For example, to achieve an "effective amount" for acute therapy, parenteral administration of a compound is typically preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg; preferably between 0.1 and 20 mg, in a manner to maintain the concentration of drug in the plasma at a concentration effective to modulate GPR65. The compounds may be administered one to four times daily at a level to achieve a total daily dose of about 0.4 to about 400 mg. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 500 mg or about 0.1 to about 50 mg in a manner consistent with the condition of the patient. Preferably the oral dose would be about 0.5 to about 50 mg or about 0.5 to about 20 mg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Examples

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

General Schemes

Abbreviations

A list of some common abbreviations is shown below—where other abbreviations are used which are not listed, these will be understood by the person skilled in the art.

br.: broad; CAN: ceric ammonium nitrate; d: doublet; DCM: dichloromethane; DIPEA: N,N-diisopropylethylamine; DMSO: dimethylsulfoxide; (ES+): electrospray ionization positive mode; $Et_3N$: triethylamine; EtOAc: ethyl acetate; h: hours; HPLC: high performance liquid chromatography; Hz: hertz; J: coupling constant; M: molar; m: multiplet [M+H]+: protonated molecular ion; MeCN: acetonitrile; MeOH: methanol; MHz: megahertz; min: minutes; ml: millilitres; MS: mass spectrometry; m/z: mass-to-charge ratio; NMR: nuclear magnetic resonance; Pd-178: chloro(crotyl)(tricyclohexylphosphine)palladium(II); PDA: photodiode array; RT: room temperature; Rt: retention time; s: singlet; SCX: solid supported cation exchange (resin); t: triplet; THF: tetrahydrofuran; UPLC: ultra performance liquid chromatography; UV: ultra-violet.

Other abbreviations are intended to convey their generally accepted meaning.

General Experimental Conditions

All starting materials and solvents were obtained either from commercial sources or prepared according to literature methods. The appropriate aniline starting materials were obtained from Sigma Aldrich, Fluorochem or Enamine store, or were synthesised as described herein. The appropriate tricyclic amine starting materials were obtained from Enamine store or were synthesised as described herein. Reaction mixtures were magnetically stirred and reactions performed at room temperature (approximately 20° C.) unless otherwise indicated.

Silica gel chromatography was performed on an automated flash chromatography system, such as CombiFlash Companion, CombiFlash Rf system or Reveleris $X_2$ flash system using RediSep® Rf or Reveleris® or the GraceResolv™ pre-packed silica (230-400 mesh, 40-63 μm) cartridges.

Analytical UPLC-MS experiments to determine retention times and associated mass ions were performed using a Waters ACQUITY UPLC® H-Class system, equipped with ACQUITY PDA Detector and ACQUITY QDa mass spectrometer or Waters SQD mass spectrometer, running the analytical method described below.

Analytical LC-MS experiments to determine retention times and associated mass ions were performed using either an Agilent 1200 series HPLC system coupled to an Agilent 1956, 6100 or 6120 series single quadrupole mass spectrometer running one of the analytical methods described below, or a Shimadzu LC-20AD series System coupled to a MS: 2020 quadupole Preparative HPLC purifications were performed either using either a Waters Waters XBridge BEH C18 ODB prep column, 5 μm, 30×100 mm column or a Phenomenex: Kinetex® 5 μm EVO C18 100 Å, AXIA Packed LC 50×30.0 mm column using a gradient of MeCN and 0.3% ammonia in water. Fractions were collected following UV detection across all wavelengths with PDA as well as a SQD2 or ACQUITY QDa mass spectrometer.

NMR spectra were recorded using either a Bruker Avance III HD 500 MHz instrument or a Bruker Avance Neo 400 MHz, using either residual non-deuterated solvent or tetra-methylsilane as reference or Varian Y 400 MHz instrument, using tetra-methylsilane as reference or a QOne AS400 400 MHz instrument using either residual non-deuterated solvent or tetra-methylsilane as reference In the absence of the absolute stereochemistry being explicitly indicated through wedged and dashed bonds, chemical structures disclosed throughout the examples are to be interpreted as depicting the racemate. For the avoidance of doubt, the invention encompasses the compounds in either configuration, as well as mixtures thereof.

Analytical Methods

Method 1—Basic 3 Min Method

Column: Waters ACQUITY UPLCO BEH C18, 1.7 μm, 2.1×30 mm at 40° C.

Detection: UV at 210-400 nm unless otherwise indicated, MS by electrospray ionisation Solvents: A: 10 mM aqueous ammonium bicarbonate, B: MeCN Gradient:

| Time | % A | % B | Flow rate (ml/min) |
|---|---|---|---|
| 0.00 | 95 | 5 | 0.77 |
| 0.11 | 95 | 5 | 0.77 |
| 2.15 | 5 | 95 | 0.77 |
| 2.56 | 5 | 95 | 0.77 |
| 2.83 | 95 | 5 | 0.77 |
| 3.00 | 95 | 5 | 0.77 |

Method 2—Basic 4 Min Method

Column: Waters X-Bridge BEH C18, 2.5 μm, 4.6×30 mm at 40° C.

Detection: UV at 254 nm unless otherwise indicated, MS by electrospray ionisation Solvents: A: 10 mM ammonium bicarbonate(aq), B: MeCN Gradient:

| Time | % A | % B | Flow rate (ml/min) |
|---|---|---|---|
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 3—Acidic 5 Min Method

Column: Agilent EclipsePlus RRHD C18, 1.8 μm, 3.0×50 mm at 25° C.

Detection: UV at 214 and 254 nm unless otherwise indicated, MS by electrospray ionisation Solvents: A: 0.05% Formic acid in water, B: 0.05% Formic acid in MeCN Gradient:

| Time | % A | % B | Flow rate (ml/min) |
|---|---|---|---|
| 0.0 | 90.0 | 10.0 | 0.8 |
| 0.5 | 90.0 | 10.0 | 0.8 |
| 4.0 | 10.0 | 90.0 | 0.8 |
| 4.5 | 0.0 | 100.0 | 0.8 |
| 4.51 | 90.0 | 10.0 | 0.8 |
| 5.00 | 90.0 | 10.0 | 0.8 |

Method 4—Acidic 5 Min Method 2

Column: Waters Sunfire, 3.5 μm, 4.6×50 mm column at 25° C.

Detection: UV at 214 and 254 nm unless otherwise indicated, MS by electrospray ionisation Solvents: A: 0.05% Formic acid in water, B: 0.05% Formic acid in MeCN Gradient:

| Time | % A | % B | Flow rate (ml/min) |
|---|---|---|---|
| 0.0 | 85.0 | 15.0 | 0.8 |
| 0.5 | 85.0 | 15.0 | 0.8 |
| 4.0 | 0.0 | 100.0 | 0.8 |
| 4.5 | 0.0 | 100.0 | 0.8 |
| 4.51 | 85.0 | 15.0 | 0.8 |
| 5.00 | 85.0 | 15.0 | 0.8 |

Experimental Scheme 1

Compound 1 (5R,8S)—N-(4-chloro-5-(trifluoromethyl)pyridin-2-yl)-1-fluoro-6,7,8,9-tetrahydro-5H-5,8-epiminocyclohepta[c]pyridine-10-carboxamide

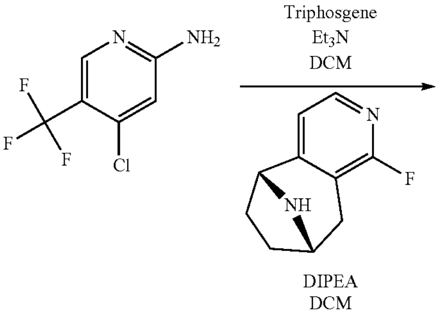

-continued

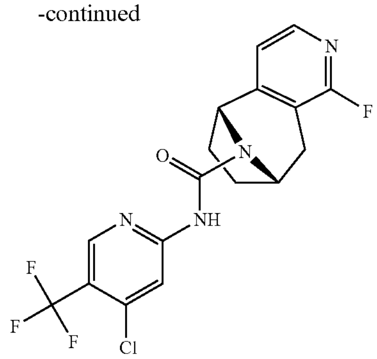

To a solution of triphosgene (13 mg, 45 μmol) in DCM (2 ml) was added 4-chloro-5-(trifluoromethyl)pyridin-2-amine (26 mg, 0.13 mmol) and $Et_3N$ (47 μl, 0.34 mmol). The reaction mixture was stirred at RT for 10 min after which a solution of (5R,8S)-1-fluoro-6,7,8,9-tetrahydro-5H-5,8-epiminocyclohepta[c]pyridine (20 mg, 0.11 mmol) in DCM (2 ml) was added. DIPEA (59 μl, 0.34 mmol) was added and the mixture was stirred at RT for 10 min. The reaction mixture was diluted with DCM (10 ml) and washed with saturated sodium bicarbonate solution (3 ml). The organic phase was passed through a hydrophobic frit and the filtrate was concentrated in vacuo. The product was purified by mass directed HPLC (35-65% MeCN/10 mM aqueous ammonium hydroxide solution) to give (5R,8S)—N-(4-chloro-5-(trifluoromethyl)pyridin-2-yl)-1-fluoro-6,7,8,9-tetrahydro-5H-5,8-epiminocyclohepta[c]-pyridine-10-carboxamide as a colourless solid. LC-MS (method 1) m/z 401.4, 403.3 at 1.49 min, $^1$H NMR (500 MHz, DMSO-d6) δ 10.29 (s, 1H), 8.64 (s, 1H), 8.15 (s, 1H), 8.01 (d, J=5.0 Hz, 1H), 7.21 (d, J=5.2 Hz, 1H), 5.38 (s, 1H), 4.92 (s, 1H), 3.17 (dd, J=17.2, 5.0 Hz, 1H), 2.59 (d, J=17.3 Hz, 1H), 2.24-2.16 (m, 2H), 1.85 (t, J=10.0 Hz, 1H), 1.73 (s, 1H).

The following compounds were prepared using appropriate starting materials in an analogous procedure to that described in Experimental Scheme 1. Where the starting materials are not described in the literature, their synthesis is described below.

Key: (a) product was purified by silica gel chromatography (0.7 M Ammonia/MeOH in DCM), (b) Reaction performed in mixture of DMF and DCM (c) was purified by chromatography on RP Flash C18 (15-75% MeCN/10 mM aqueous ammonium bicarbonate) (d) $M-H^-$ ($ES^-$) reported as no ionisation observed in $ES^+$

| Compound | Structure | LCMS method 1 Rt $[M + H]^+$ | NMR |
|---|---|---|---|
| 2 (a) | 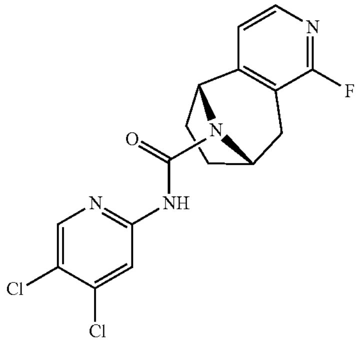 (5R,8S)-N-(4,5-Dichloropyridin-2-yl)-1-fluoro-6,7,8,9-tetrahydro-5H-5,8-epiminocyclohepta[c]pyridine-10-carboxamide | 367.2, 369.3 at 1.41 min | $^1$H NMR (500 MHz, DMSO-d6) δ 9.91 (s, 1H), 8.44 (s, 1H), 8.11 (s, 1H), 8.01 (d, J = 5.0 Hz, 1H), 7.22-7.18 (m, 1H), 5.36 (s, 1H), 4.89 (s, 1H), 3.15 (dd, J = 17.3, 4.9 Hz, 1H), 2.58 (d, J = 17.3 Hz, 1H), 2.25-2.12 (m, 2H), 1.88-1.80 (m, 1H), 1.74 (dd, J = 12.1, 5.6 Hz, 1H). |
| 3 (a) | 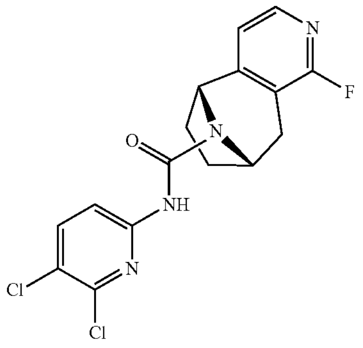 (5R,8S)-N-(5,6-Dichloropyridin-2-yl)-1-fluoro-6,7,8,9-tetrahydro-5H-5,8-epiminocyclohepta[c]pyridine-10-carboxamide | 367.2, 369.3 at 1.42 min | $^1$H NMR (500 MHz, DMSO-d6) δ 9.95 (s, 1H), 8.00 (d, J = 5.0 Hz, 1H), 7.94 (d, J = 8.8 Hz, 1H), 7.86 (d, J = 8.8 Hz, 1H), 7.20 (dd, J = 5.0, 1.6 Hz, 1H), 5.36 (s, 1H), 4.88 (s, 1H), 3.15 (dd, J = 17.3, 5.1 Hz, 1H), 2.57 (d, J = 17.3 Hz, 1H), 2.26-2.11 (m, 2H), 1.87-1.79 (m, 1H), 1.73 (dd, J = 12.5, 6.2 Hz, 1H) |

-continued

| Compound | Structure | LCMS method 1 Rt [M + H]+ | NMR |
|---|---|---|---|
| 4 [(a)] | 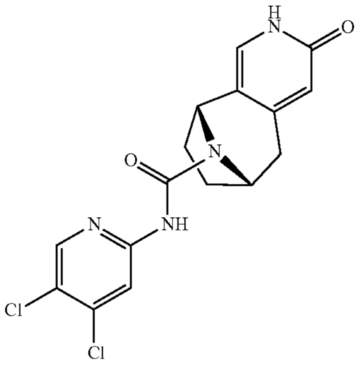 (6S,9R)-N-(4,5-Dichloropyridin-2-yl)-3-oxo-3,5,6,7,8,9-hexahydro-2H-6,9-epiminocyclohepta[c]pyridine-10-carboxamide | 365.3, 367.3 at 1.05 min | $^1$H NMR (500 MHz, DMSO-d6) δ 11.26 (s, 1H), 9.71 (s, 1H), 8.44 (s, 1H), 8.15 (s, 1H), 7.21 (d, J = 15.0 Hz, 1H), 6.08 (d, J = 6.8 Hz, 1H), 5.19 (d, J = 5.6 Hz, 1H), 4.67 (s, 1H), 3.10 (dd, J = 18.1, 5.2 Hz, 1H), 2.54 (d, J = 17.9 Hz, 1H), 2.17-2.00 (m, 2H), 1.71 (t, J = 10.4 Hz, 1H), 1.63 (dt, J = 15.1, 6.9 Hz, 1H). |
| 5 [(a)] | 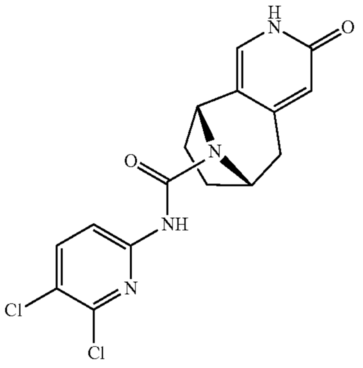 (6S,9R)-N-(5,6-Dichloropyridin-2-yl)-3-oxo-3,5,6,7,8,9-hexahydro-2H-6,9-epiminocyclohepta[c]pyridine-10-carboxamide | 365.3, 367.3 at 1.06 min | $^1$H NMR (500 MHz, DMSO-d6) δ 11.26 (s, 1H), 9.76 (s, 1H), 7.95 (d, J = 8.8 Hz, 1H), 7.89 (d, J = 8.8 Hz, 1H), 7.20 (s, 1H), 6.08 (s, 1H), 5.19 (s, 1H), 4.67 (s, 1H), 3.10 (dd, J = 17.6, 5.1 Hz, 1H), 2.56 (s, 1H), 2.12 (t, J = 10.4 Hz, 1H), 2.05 (dd, J = 12.0, 5.9 Hz, 1H), 1.70 (t, J = 10.5 Hz, 1H), 1.66-1.59 (m, 1H). |
| 6 [(b)(c)] | 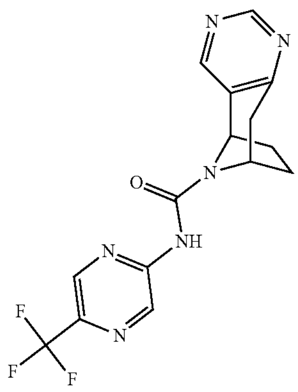 (±)-N-(5-(Trifluoromethyl)pyrazin-2-yl)-6,7,8,9-tetrahydro-5H-5,8-epiminocyclohepta[d]pyrimidine-10-carboxamide | 351.3 at 0.99 min | $^1$H NMR (500 MHz, DMSO-d6) δ 10.43 (s, 1H), 9.21 (d, J = 1.4 Hz, 1H), 8.96 (s, 1H), 8.81 (d, J = 1.5 Hz, 1H), 8.60 (s, 1H), 5.43 (s, 1H), 4.93 (s, 1H), 3.36 (dd, J = 18.2, 4.9 Hz, 1H), 2.83-2.75 (m, 1H), 2.31-2.16 (m, 2H), 1.91 (dd, J = 11.7, 8.9 Hz, 1H), 1.80-1.71 (m, 1H). |

-continued

| Compound | Structure | LCMS method 1 Rt [M + H]+ | NMR |
|---|---|---|---|
| 8 | 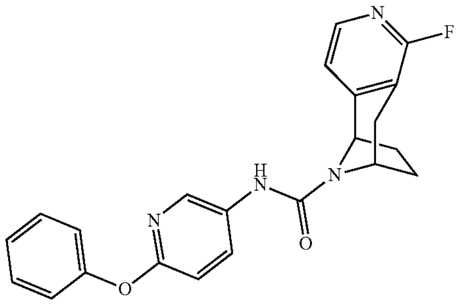 (±)-1-fluoro-N-(6-Phenoxypyridin-3-yl)-6,7,8,9-tetrahydro-5H-5,8-epiminocyclohepta[c]pyridine-10-carboxamide | 391.2 at 1.24 min | 1H NMR (400 MHz, DMSO-d6) δ 8.87 (s, 1H), 8.19 (d, J = 2.7 Hz, 1H), 8.01 (d, J = 4.7 Hz, 1H), 7.91 (dt, J = 8.9, 2.4 Hz, 1H), 7.38 (dd, J = 8.6, 7.3 Hz, 2H), 7.21 (d, J = 1.7 Hz, 1H), 7.20-7.11 (m, 2H), 7.08-7.01 (m, 2H), 6.93 (d, J = 8.8 Hz, 1H), 5.23 (d, J = 6.1 Hz, 1H), 4.83-4.76 (m, 1H), 3.16 (dd, J = 17.2, 5.0 Hz, 1H), 2.58 (d, J = 17.4 Hz, 1H), 2.20 (dtd, J = 17.7, 12.0, 11.5, 7.1 Hz, 2H), 1.89-1.80 (m, 1H), 1.80-1.70 (m, 1H). |
| 9 | 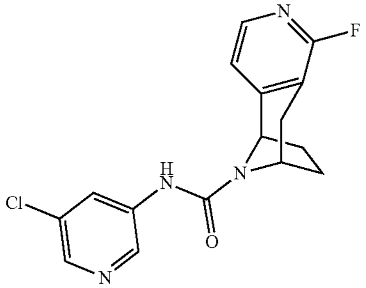 (5R,8S)-N-(5-chloropyridin-3-yl)-1-fluoro-6,7,8,9-tetrahydro-5H-5,8-epiminocyclohepta[c]pyridine-10-carboxamide | 333.2, 335.2 at 1.06 | 1H NMR (400 MHz, DMSO-d6) δ 9.11 (s, 1H), 8.57 (d, J = 2.2 Hz, 2H), 8.18 (d, J = 2.2 Hz, 2H), 8.08 (t, J = 2.2 Hz, 2H), 8.01 (d, J = 5.0 Hz, 2H), 7.21 (dd, J = 5.0, 1.7 Hz, 2H), 5.25 (d, J = 6.2 Hz, 2H), 4.83 (t, J = 6.1 Hz, 2H), 3.17 (dd, J = 17.5, 5.0 Hz, 2H), 2.63 (s, 1H), 2.25 (s, 1H), 2.19 (td, J = 11.6, 10.6, 4.7 Hz, 2H), 1.90-1.82 (m, 2H), 1.77 (dt, J = 14.3, 6.7 Hz, 2H). |
| 10 | 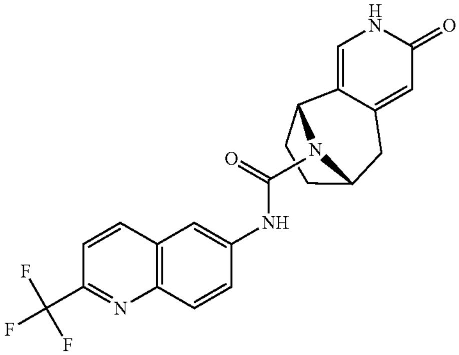 (6S,9R)-3-Oxo-N-(2-(trifluoromethyl)quinolin-6-yl)-3,5,6,7,8,9-hexahydro-2H-6,9-epiminocyclohepta[c]pyridine-10-carboxamide | 415.2 at 1.08 min | $^1$H NMR (500 MHz, DMSO-d6) δ 11.29 (s, 1H), 9.13 (s, 1H), 8.51 (d, J = 8.6 Hz, 1H), 8.30 (d, J = 2.3 Hz, 1H), 8.05 (d, J = 9.2 Hz, 1H), 7.98 (dd, J = 9.2, 2.4 Hz, 1H), 7.84 (d, J = 8.6 Hz, 1H), 7.23 (s, 1H), 6.11 (s, 1H), 5.15 (d, J = 6.0 Hz, 1H), 4.68 (t, J = 6.5 Hz, 1H), 3.15 (m, 1H), 2.59 (d, J = 17.9 Hz, 1H), 2.21 (q, J = 11.1 Hz, 1H), 2.10 (tt, J = 11.6, 6.1 Hz, 1H), 1.79-1.63 (m, 2H). |

-continued

| Compound | Structure | LCMS method 1 Rt [M + H]+ | NMR |
|---|---|---|---|
| 11 | 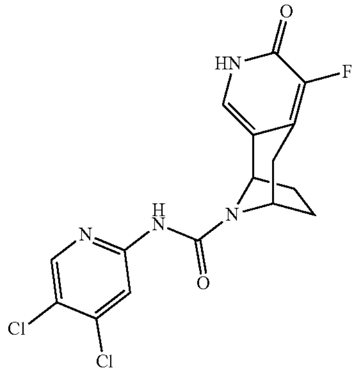 (±)-N-(4,5-Dichloropyridin-2-yl)-4-fluoro-3-oxo-3,5,6,7,8,9-hexahydro-2H-6,9-epiminocyclohepta[c]pyridine-10-carboxamide | 383.3, 385.3 at 1.06 min | $^1$H NMR (500 MHz, DMSO-d6) δ 11.83 (s, 1H), 9.77 (s, 1H), 8.44 (s, 1H), 8.14 (s, 1H), 7.10 (s, 1H), 5.24 (d, J = 6.0 Hz, 1H), 4.74 (s, 1H), 3.11-3.02 (m, 1H), 2.64 (d, J = 17.9 Hz, 1H), 2.13 (dd, J = 18.3, 8.0 Hz, 1H), 2.08 (dd, J = 11.7, 5.9 Hz, 1H), 1.78-1.64 (m, 2H). |
| 12 | 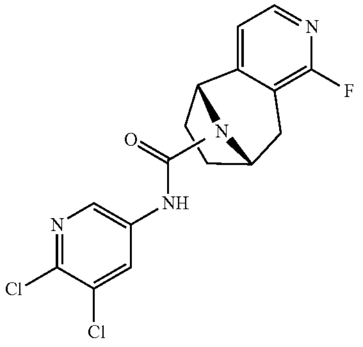 (5R,8S)-N-(5,6-Dichloropyridin-3-yl)-1-fluoro-6,7,8,9-tetrahydro-5H-5,8-epiminocyclohepta[c]pyridine-10-carboxamide | 366.9, 369.6 at 1.42 min | $^1$H NMR (500 MHz, DMSO-d6) δ 9.95 (s, 1H), 8.00 (d, J = 5.0 Hz, 1H), 7.94 (d, J = 8.8 Hz, 1H), 7.86 (d, J = 8.8 Hz, 1H), 7.32-7.16 (m, 1H), 5.36 (s, 1H), 4.88 (s, 1H), 3.15 (dd, J = 17.4, 5.1 Hz, 1H), 2.57 (d, J = 17.4 Hz, 1H), 2.26-2.10 (m, 2H), 1.93-1.79 (m, 1H), 1.73 (dt, J = 10.7, 5.5 Hz, 1H) |
| 13 | 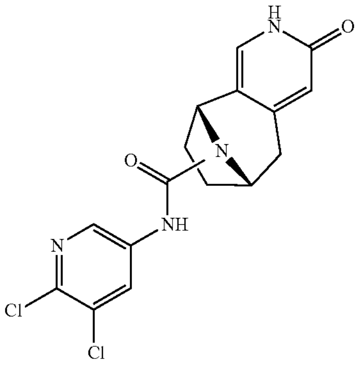 (6S,9R)-N-(5,6-Dichloropyridin-3-yl)-3-oxo-3,5,6,7,8,9-hexahydro-2H-6,9-epiminocyclohepta[c]pyridine-10-carboxamide | 365.3, 367.3 at 0.96 min | $^1$H NMR (500 MHz, DMSO-d6) δ 11.29 (s, 1H), 9.09 (s, 1H), 8.48 (d, J = 2.4 Hz, 1H), 8.29 (d, J = 2.4 Hz, 1H), 7.21 (s, 1H), 6.10 (s, 1H), 5.09 (d, J = 6.0 Hz, 1H), 4.62 (t, J = 6.4 Hz, 1H), 3.10 (dd, J = 17.9, 5.1 Hz, 1H), 2.58 (d, J = 17.9 Hz, 1H), 2.18 (q, J = 11.1 Hz, 1H), 2.06 (tt, J = 11.6, 6.2 Hz, 1H), 1.77-1.67 (m, 1H), 1.67-1.61 (m, 1H) |

-continued

| Compound | Structure | LCMS method 1 Rt [M + H]$^+$ | NMR |
|---|---|---|---|
| 14 | 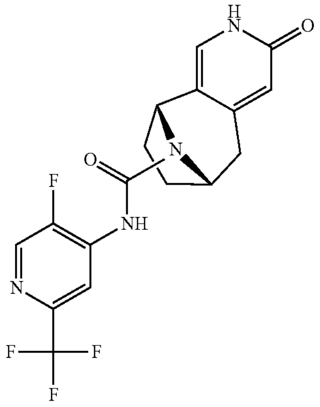 (6S,9R)-N-(5-Fluoro-2-(trifluoromethyl)pyridin-4-yl)-3-oxo-3,5,6,7,8,9-hexahydro-2H-6,9-epiminocyclohepta[c]pyridine-10-carboxamide | 383.3 at 0.92 min | $^1$H NMR (500 MHz, DMSO-d6) δ 11.30 (s, 1H), 9.24 (s, 1H), 8.64 (d, J = 2.7 Hz, 1H), 8.38 (d, J = 6.0 Hz, 1H), 7.23 (s, 1H), 6.10 (s, 1H), 5.13 (d, J = 6.0 Hz, 1H), 4.66 (s, 1H), 3.17 (d, J = 7.2 Hz, 1H), 2.58 (d, J = 17.8 Hz, 1H), 2.21-2.13 (m, 1H), 2.08 (dt, J = 11.8, 5.8 Hz, 1H), 1.77-1.67 (m, 1H), 1.66 (s, 1H) |
| 15 | 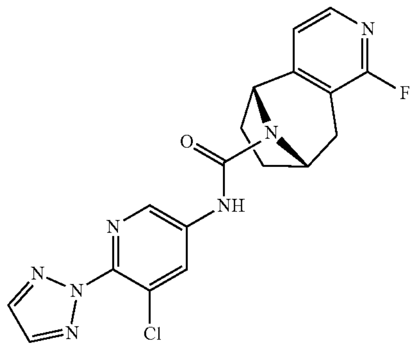 (5R,8S)-N-(5-Chloro-6-(2H-1,2,3-triazol-2-yl)pyridin-3-yl)-1-fluoro-6,7,8,9-tetrahydro-5H-5,8-epiminocyclohepta[c]pyridine-10-carboxamide | 400.4, 402.4 at 1.13 min | $^1$H NMR (500 MHz, DMSO-d6) δ 9.44 (s, 1H), 8.63 (d, J = 2.3 Hz, 1H), 8.40 (d, J = 2.3 Hz, 1H), 8.13 (s, 2H), 8.03 (d, J = 5.0 Hz, 1H), 7.24 (dd, J = 5.1, 1.6 Hz, 1H), 5.29 (d, J = 6.3 Hz, 1H), 4.98-4.82 (m, 1H), 3.21 (dd, J = 17.3, 4.9 Hz, 1H), 2.64 (d, J = 17.3 Hz, 1H), 2.37-2.19 (m, 2H), 1.96-1.84 (m, 1H), 1.82-1.72 (m, 1H) |
| 16 | 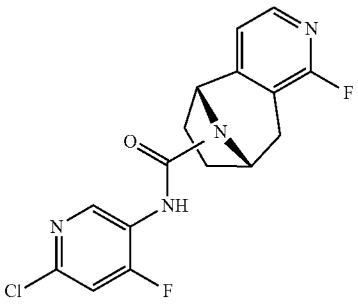 (5R,8S)-N-(6-Chloro-4-fluoropyridin-3-yl)-1-fluoro-6,7,8,9-tetrahydro-5H-5,8-epiminocyclohepta[c]pyridine-10-carboxamide | 351.3, 353.3 at 1.05 min | $^1$H NMR (500 MHz, DMSO-d6) δ 8.89 (s, 1H), 8.45 (d, J = 9.9 Hz, 1H), 8.01 (d, J = 5.0 Hz, 1H), 7.62 (d, J = 9.8 Hz, 1H), 7.20 (dd, J = 5.1, 1.6 Hz, 1H), 5.20 (d, J = 6.2 Hz, 1H), 4.77 (t, J = 6.3 Hz, 1H), 3.18 (dd, J = 17.5, 5.0 Hz, 1H), 2.59 (d, J = 17.3 Hz, 1H), 2.30-2.06 (m, 2H), 1.93-1.81 (m, 1H), 1.81-1.68 (m, 1H). |

-continued

| Compound | Structure | LCMS method 1 Rt [M + H]$^+$ | NMR |
|---|---|---|---|
| 17 | 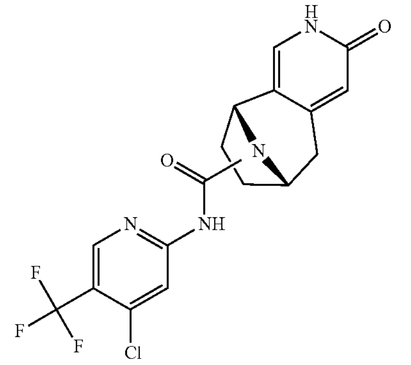 (6S,9R)-N-(4-Chloro-5-(trifluoromethyl)pyridin-2-yl)-3-oxo-3,5,6,7,8,9-hexahydro-2H-6,9-epiminocyclohepta[c]pyridine-10-carboxamide | 399.3, 401.3 at 1.74 min | $^1$H NMR (500 MHz, DMSO-d6) δ 8.63 (s, 1H), 8.18 (s, 1H), 7.20 (s, 1H), 6.09 (s, 1H), 5.21 (s, 1H), 4.70 (s, 1H), 3.11 (dd, J = 17.9, 5.0 Hz, 1H), 2.55 (d, J = 17.9 Hz, 1H), 2.15 (q, J = 10.9 Hz, 1H), 2.06 (dd, J = 13.0, 6.9 Hz, 1H), 1.72 (t, J = 10.4 Hz, 1H), 1.64 (dt, J = 15.2, 7.7 Hz, 1H). 2 exchangeable protons not observed |
| 18 | 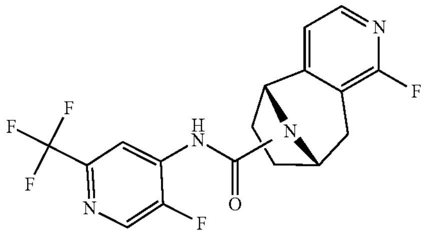 (5R,8S)-1-Fluoro-N-(5-fluoro-2-(trifluoromethyl)pyridin-4-yl)-6,7,8,9-tetrahydro-5H-5,8-epiminocyclohepta[c]pyridine-10-carboxamide | 385.1 at 1.29 min | $^1$H NMR (500 MHz, DMSO-d6) δ 9.41 (s, 1H), 8.64 (d, J = 2.8 Hz, 1H), 8.35 (d, J = 6.1 Hz, 1H), 8.02 (d, J = 5.0 Hz, 1H), 7.22 (dd, J = 5.0, 1.6 Hz, 1H), 5.29 (d, J = 6.0 Hz, 1H), 4.88 (d, J = 6.4 Hz, 1H), 3.20 (dd, J = 17.3, 5.1 Hz, 1H), 2.61 (d, J = 17.3 Hz, 1H), 2.28-2.15 (m, 2H), 1.86 (dd, J = 11.4, 8.7 Hz, 1H), 1.76 (dt, J = 13.2, 6.7 Hz, 1H). |
| 19 | 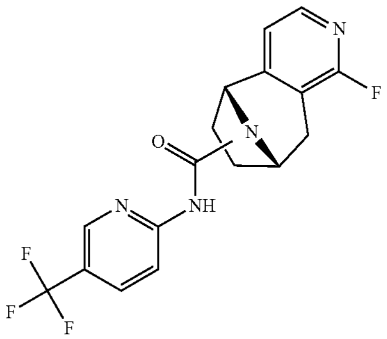 (5R,8S)-1-Fluoro-N-(5-(trifluoromethyl)pyridin-2-yl)-6,7,8,9-tetrahydro-5H-5,8-epiminocyclohepta[c]pyridine-10-carboxamide | 367.1 at 1.33 min | $^1$H NMR (500 MHz, DMSO-d6) δ 10.00 (s, 1H), 8.61 (s, 1H), 8.15-7.71 (m, 3H), 7.40-6.92 (m, 1H), 5.39 (s, 1H), 4.91 (s, 1H), 3.16 (dd, J = 17.4, 5.1 Hz, 1H), 2.59 (d, J = 17.4 Hz, 1H), 2.29-2.11 (m, 2H), 1.85 (t, J = 10.0 Hz, 1H), 1.75 (dd, J = 12.5, 5.2 Hz, 1H) |

-continued

| Compound | Structure | LCMS method 1 Rt [M + H]$^+$ | NMR |
|---|---|---|---|
| 20 | 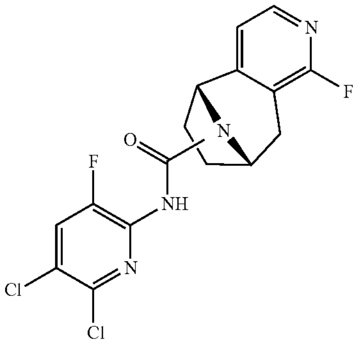 (5R,8S)-N-(5,6-Dichloro-3-fluoropyridin-2-yl)-1-fluoro-6,7,8,9-tetrahydro-5H-5,8-epiminocyclohepta[c]pyridine-10-carboxamide | 382.7, 384.6 at 1.21 min[d] | $^1$H NMR (500 MHz, DMSO-d6) δ 8.42 (s, 1H), 8.01 (d, J = 5.0 Hz, 1H), 7.37-6.94 (m, 1H), 5.20 (d, J = 5.8 Hz, 1H), 4.76 (s, 1H), 3.18 (dd, J = 17.3, 5.0 Hz, 1H), 2.59 (d, J = 17.3 Hz, 1H), 2.30-2.11 (m, 2H), 1.85 (dd, J = 11.4, 8.8 Hz, 1H), 1.79-1.65 (m, 1H), 1 Exchangeable proton not observed |
| 29 | 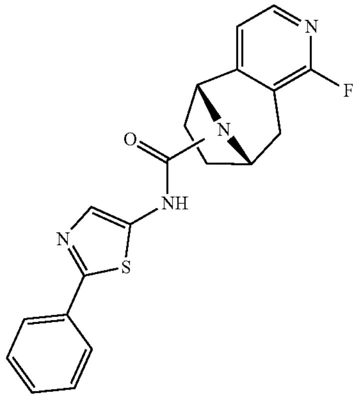 (5R,8S)-1-Fluoro-N-(2-phenylthiazol-5-yl)-6,7,8,9-tetrahydro-5H-5,8-epiminocyclohepta[c]pyridine-10-carboxamide | 381.2 at 1.72 min | $^1$H NMR (400 MHz, DMSO) δ 10.22 (s, 1H), 8.03 (d, J = 5.0 Hz, 1H), 7.83-7.76 (m, 2H), 7.49 (s, 1H), 7.47-7.40 (m, 2H), 7.40-7.34 (m, 1H), 7.22 (dd, J = 5.1, 1.6 Hz, 1H), 5.27 (d, J = 6.1 Hz, 1H), 4.85-4.76 (m, 1H), 3.14 (dd, J = 18.1, 4.9 Hz, 1H), 2.63 (d, J = 17.3 Hz, 1H), 2.29-2.13 (m, 2H), 1.92-1.82 (m, 1H), 1.82-1.73 (m, 1H). |
| 30 | 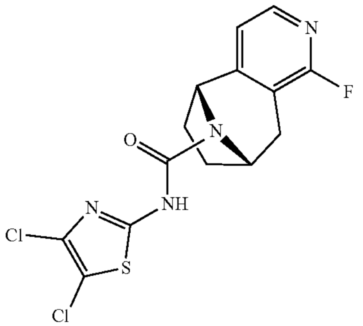 (5R,8S)-N-(4,5-Dichlorothiazol-2-yl)-1-fluoro-6,7,8,9-tetrahydro-5H-5,8-epiminocyclohepta[c]pyridine-10-carboxamide | 371.2, 373.8 (ES−) at 0.77 min | $^1$H NMR (400 MHz, DMSO) δ 11.74 (s, 1H), 8.02 (d, J = 5.0 Hz, 1H), 7.24-7.15 (m, 1H), 5.39-5.28 (m, 1H), 4.92-4.82 (m, 1H), 3.11 (dd, J = 17.5, 5.0 Hz, 1H), 2.61 (d, J = 17.4 Hz, 1H), 2.29-2.11 (m, 2H), 1.93-1.82 (m, 1H), 1.82-1.70 (m, 1H). |

Intermediate 1 (I-1)

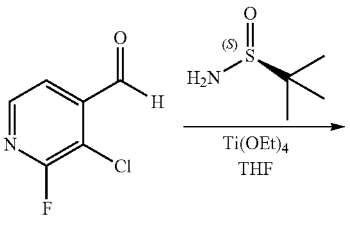

I-1a

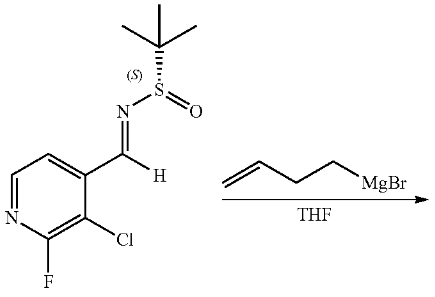

I-1b

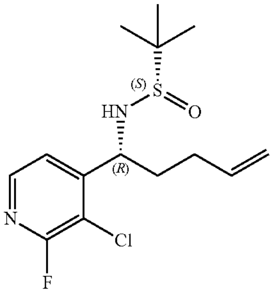

I-1c

I-1c

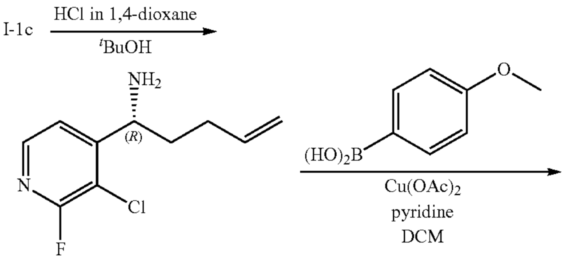

I-1d

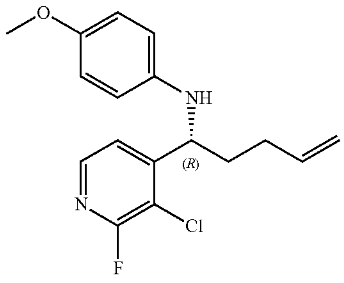

I-1e

I-1e

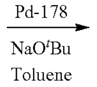

-continued

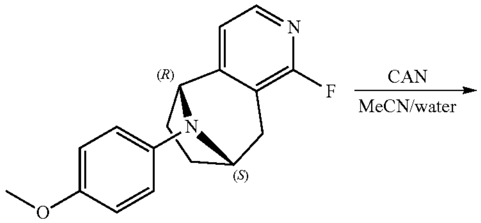

I-1f

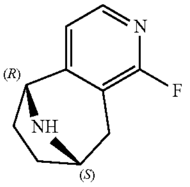

I-1

Step 1: To a solution of 3-chloro-2-fluoroisonicotinaldehyde I-1a (1.00 g, 6.27 mmol) in THF (17 ml) was added titanium (IV) ethoxide (2.63 ml, 12.5 mmol) in one portion at RT. The mixture was stirred at RT for 5 min before (S)-tert-butylsulfinamide (760 mg, 6.27 mmol) was added in one portion. The resulting mixture was stirred at RT for 16 h. Brine (30 ml) was added, and the mixture stirred for 10 minutes then filtered through celite. The filtrate was extracted with EtOAc (2×20 ml). The combined organic layers were dried over magnesium sulfate and concentrated in vacuo to give (S,E)-N-((3-chloro-2-fluoropyridin-4-yl)methylene)-2-methylpropane-2-sulfinamide (I-1b) as a pale yellow solid. LCMS (method 1) m/z 227.5 $(M-Cl)^+$ $(ES^+)$, at 1.36 min. $^1H$ NMR (500 MHz, DMSO-d6) δ 8.81 (s, 1H), 8.33 (dt, J=5.1, 0.8 Hz, 1H), 7.90 (d, J=5.1 Hz, 1H), 1.22 (s, 9H).

Step 2: To a solution of (S,E)-N-((3-chloro-2-fluoropyridin-4-yl)methylene)-2-methylpropane-2-sulfinamide (1.3824 g, 5.2617 mmol) (I-1b) in THF (22 ml) was added but-3-en-1-yl magnesium bromide (0.5 M, 31.57 ml, 15.79 mmol) dropwise at −78° C. The mixture was warmed to RT slowly and stirred for 72 h. Saturated ammonium chloride solution (10 ml) was added and the product was extracted with EtOAc (3×10 ml). The combined organic phase was dried with magnesium sulfate and concentrated in vacuo. The product was purified by silica gel chromatography (0-100% EtOAc/isohexane) to give (S)—N—((R)-1-(3-chloro-2-fluoropyridin-4-yl)pent-4-en-1-yl)-2-methylpropane-2-sulfinamide (1-1c) as a pale yellow solid. LCMS (method 1) m/z 316.7, 319.1 $(M-H)^-$ $(ES^-)$, at 1.39 min. 1H NMR (500 MHz, DMSO-d6) δ 8.21 (dd, J=5.2, 0.8 Hz, 1H), 7.53 (d, J=5.2 Hz, 1H), 5.90 (d, J=7.3 Hz, 1H), 5.81 (dddd, J=17.3, 10.2, 7.1, 6.1 Hz, 1H), 5.10 (dq, J=17.2, 1.7 Hz, 1H), 5.02 (ddt, J=10.2, 2.3, 1.2 Hz, 1H), 4.66 (ddd, J=8.6, 7.3, 5.3 Hz, 1H), 2.27-2.08 (m, 2H), 1.97-1.87 (m, 1H), 1.80-1.70 (m, 1H), 1.07 (s, 9H).

Step 3: To a solution of (S)—N—((R)-1-(3-chloro-2-fluoropyridin-4-yl)pent-4-en-1-yl)-2-methylpropane-2-sulfinamide (1-1c) (714 mg, 2.015 mmol) in $^t$BuOH (7.2 ml) was added a solution of HCl in 1,4-dioxane (4 M, 3.0 ml, 12.09 mmol) at RT and stirred for 2.5 h. The reaction mixture was quenched with saturated aqueous sodium bicarbonate solution (100 ml) and extracted with DCM (3×30 ml). The organic layers were combined, dried over magnesium sulfate and concentrated in vacuo to give (R)-1-(3-chloro-2-fluoropyridin-4-yl)pent-4-en-1-amine as a pale yellow liquid (1-1d) as an orange/brown oil. LCMS (method 1): m/z 215.4, 217.3 $(M+H)^+$ $(ES^+)$; at 1.17 min, 1H NMR (500 MHz, DMSO-d6) δ 8.16 (dd, J=5.1, 0.9 Hz, 1H), 7.62 (d, J=5.1 Hz, 1H), 5.80 (ddt, J=16.9, 10.2, 6.6 Hz, 1H), 5.02 (dq, J=17.4, 1.8 Hz, 1H), 4.96 (ddt, J=10.2, 2.3, 1.3 Hz, 1H), 4.22 (dd, J=8.1, 5.1 Hz, 1H), 2.23-2.01 (m, 2H), 1.76-1.50 (m, 2H), 2 NH protons not observed.

Step 4: To a solution of (R)-1-(3-chloro-2-fluoropyridin-4-yl)pent-4-en-1-amine (1-1d) (644.3 mg, 3.00 mmol), (4-methoxyphenyl)boronic acid (1.37 g, 9.0 mmol), and $Cu(OAc)_2$ (820 mg, 4.50 mmol) in DCM (100 ml) was added pyridine (1.2 ml, 15.0 mmol) dropwise. The mixture was stirred at RT open to air for 16 h. 2M NaOH aqueous solution (20 ml) was added followed by water (20 ml) and the mixture extracted with DCM (3×20 ml). The combined organic phase was dried over magnesium sulfate and concentrated in vacuo. The product was purified by silica gel chromatography (0%-100% DCM/isohexane) to give (R)—N-(1-(3-chloro-2-fluoropyridin-4-yl)pent-4-en-1-yl)-4-methoxyaniline (1-1e) as a yellow oil. LCMS (method 1): m/z 321.1, 323.4 $(M+H)^+$ $(ES^+)$; at 1.73 min, $^1H$ NMR (500 MHz, DMSO-d6) δ 8.10 (d, J=5.1 Hz, 1H), 7.41 (d, J=5.1 Hz, 1H), 6.65 (d, J=8.9 Hz, 2H), 6.38 (d, J=8.9 Hz, 2H), 6.09 (d, J=8.3 Hz, 1H), 5.84 (ddt, J=17.0, 10.2, 6.6 Hz, 1H), 5.10-4.88 (m, 2H), 4.68 (td, J=8.5, 4.7 Hz, 1H), 3.57 (s, 3H), 2.34-2.24 (m, 1H), 2.23-2.12 (m, 1H), 1.87-1.69 (m, 2H).

Step 5: A three-neck flask was charged with Pd-178 (7.44 mg, 15.6 μmol) and sodium tert-butoxide (22.5 mg, 234 μmol) and purged with $N_2$. A solution of (R)—N-(1-(3-chloro-2-fluoropyridin-4-yl)pent-4-en-1-yl)-4-methoxyaniline (1-1e) (50.0 mg, 156 μmol) in toluene (1 ml) was added dropwise. The resulting mixture was heated to 95° C. for 1.5 h. The reaction mixture was cooled to RT and filtered through celite, washing with EtOAc (3×20 ml). The filtrate was concentrated in vacuo. The product was purified by silica gel chromatography (0%-50% EtOAc/heptane) to give (5R,8S)-1-fluoro-10-(4-methoxyphenyl)-6,7,8,9-tetrahydro-5H-5,8-epiminocyclohepta[c]pyridine (1-1f) a white solid. LCMS (method 1) m/z 285.3 $(M+H)^+$ $(ES^+)$, at 1.35 min. $^1H$ NMR (500 MHz, DMSO-d6) δ 7.95 (d, J=4.9 Hz, 1H), 7.29 (dd, J=5.0, 1.7 Hz, 1H), 6.80 (d, J=9.1 Hz, 2H), 6.71 (d, J=9.1 Hz, 2H), 4.92 (d, J=5.6 Hz, 1H), 4.56 (t, J=5.9 Hz, 1H), 3.61 (s, 3H), 2.92 (dd, J=17.6, 4.9 Hz, 1H), 2.35 (d, J=17.5 Hz, 1H), 2.32-2.19 (m, 2H), 1.91-1.82 (m, 1H), 1.81-1.74 (m, 1H).

Step 6: A solution of (5R,8S)-1-fluoro-10-(4-methoxyphenyl)-6,7,8,9-tetrahydro-5H-5,8-epiminocyclohepta[c]pyridine (1-1f) (69 mg, 232 μmol) in MeCN (3.2 ml) was cooled to 0° C. before a solution of CAN (381 mg, 696 μmol) in water (3.2 ml) was added dropwise. After the addition was completed the reaction was stirred for 1 h at 0° C. 2 M aqueous sodium hydroxide (5 ml) and water (5 ml) were added and the mixture extracted with DCM (3×10 ml). The combined organic layers were dried over magnesium sulfate and concentrated in vacuo to give (5R,8S)-1-fluoro-6,7,8,9-tetrahydro-5H-5,8-epiminocyclohepta[c]pyridine (1-1) as a pale pink solid. LCMS (method 1): m/z 179.2 $(M+H)^+$ $(ES^+)$; at 0.69 min, $^1H$ NMR (500 MHz, DMSO-d6) δ 7.91 (dd, J=5.0, 0.9 Hz, 1H), 7.04 (dd, J=5.0, 1.9 Hz, 1H), 4.17 (d, J=5.3 Hz, 1H), 3.78 (t, J=6.0 Hz, 1H), 2.85 (dd, J=17.1, 5.2 Hz, 1H), 2.74 (s, 1H), 2.38 (d, J=17.0 Hz, 1H), 2.01-1.85 (m, 2H), 1.73 (t, J=9.1 Hz, 1H), 1.51 (dt, J=9.4, 5.4 Hz, 1H).

Intermediate 2 (I-2)

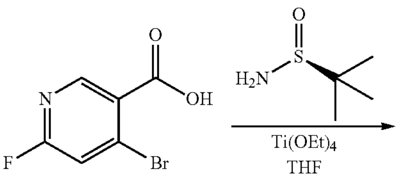

I-2a

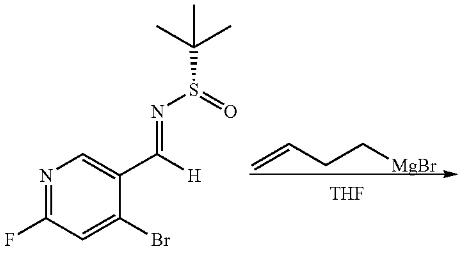

I-2b

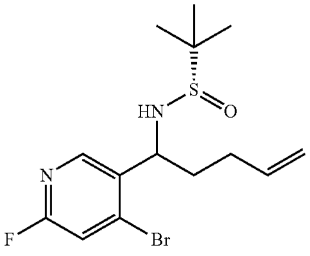

I-2c

I-2c

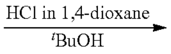

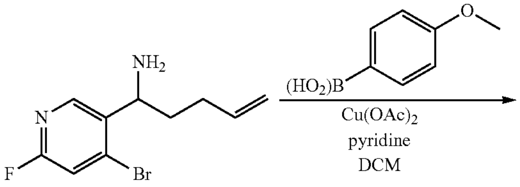

I-2d

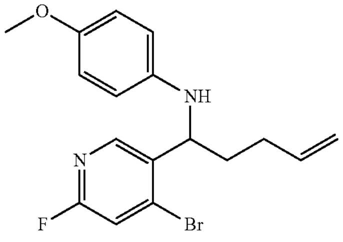

I-2e

I-2e

-continued

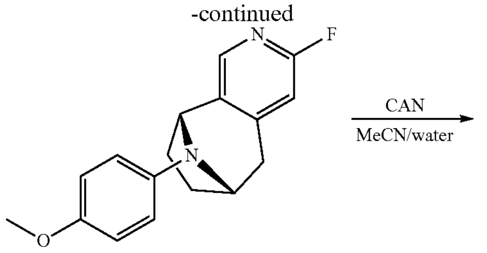

I-2f

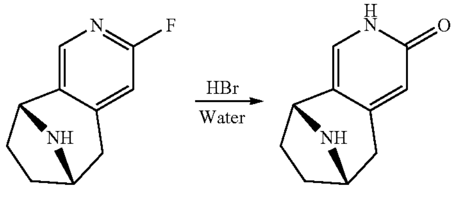

I-2g I-2

Step 1: (S,E)-N-((4-bromo-6-fluoropyridin-3-yl)methylene)-2-methylpropane-2-sulfinamide I-2b was synthesised from 4-bromo-6-fluoronicotinaldehyde I-2a using a procedure essentially the same as for I-1b. LCMS (method 2): m/z 307.0, 308.9 $(M+H)^+$ $(ES^+)$; at 2.05 min, $^1H$ NMR (500 MHz, DMSO-d6) δ 8.81 (s, 1H), 8.73 (s, 1H), 7.88 (d, J=2.4 Hz, 1H), 1.21 (s, 9H).

Step 2: To a solution of ((S,E)-N-((4-bromo-6-fluoropyridin-3-yl)methylene)-2-methylpropane-2-sulfinamide I-2b (7.00 g, 22.8 mmol) in THF (114 ml) was added but-3-en-1-yl magnesium bromide (2.54 M, 17.9 ml, 45.6 mmol) dropwise at −78° C. The mixture was warmed to RT slowly and stirred for 16 h. Saturated ammonium chloride solution (10 ml) was added and the product was extracted with EtOAc (2×10 ml). The combined organic phase was dried with magnesium sulfate and concentrated in vacuo. The product was purified by silica gel chromatography (0-10% IPA/isohexane) to give a 2:1 mixture of the diastereomers of (S)—N-(1-(4-bromo-6-fluoropyridin-3-yl)pent-4-en-1-yl)-2-methylpropane-2-sulfinamide I-2c as a pale yellow oil. LCMS (method 1) m/z 363.3, 365.4 $(M+H)^+$ (ES+), at 1.39 and 1.42 min.

Major diastereomer: $^1H$ NMR (500 MHz, DMSO-d6) δ 8.43 (s, 1H), 7.60 (d, J=2.6 Hz, 1H), 6.00 (d, J=9.5 Hz, 1H), 5.82 (ddt, J=16.7, 10.3, 6.6 Hz, 1H), 5.12-4.97 (m, 2H), 4.64-4.50 (m, 1H), 2.26-2.14 (m, 1H), 2.16-2.05 (m, 1H), 1.94-1.78 (m, 1H), 1.78-1.66 (m, 1H), 1.13 (s, 9H).

Minor diastereomer: $^1H$ NMR (500 MHz, DMSO-d6) δ 8.33 (s, 1H), 7.61 (d, J=2.5 Hz, 1H), 5.82 (ddt, J=16.7, 10.3, 6.6 Hz, 1H), 5.76 (d, J=7.0 Hz, 1H), 5.12-4.97 (m, 2H), 4.64-4.50 (m, 1H), 2.26-2.14 (m, 1H), 2.16-2.05 (m, 1H), 2.03-1.92 (m, 1H), 1.94-1.78 (m, 1H), 1.07 (s, 9H).

Step 3: 1-(4-Bromo-6-fluoropyridin-3-yl)pent-4-en-1-amine I-2d was synthesised from (S)—N-(1-(4-bromo-6-fluoropyridin-3-yl)pent-4-en-1-yl)-2-methylpropane-2-sulfinamide I-2c using a procedure essentially the same as for I-1d. LCMS (method 1) m/z 259.2, 261.2 $(M+H)^+$ $(ES^+)$, at 1.21 min. $^1H$ NMR (500 MHz, DMSO-d6) δ 8.41 (s, 1H), 7.55 (d, J=2.7 Hz, 1H), 5.82 (ddt, J=16.9, 10.2, 6.6 Hz, 1H), 5.03 (dq, J=17.2, 1.8 Hz, 1H), 4.95 (ddt, J=10.2, 2.3, 1.3 Hz, 1H), 4.12 (dd, J=8.2, 4.9 Hz, 1H), 2.25-1.98 (m, 4H), 1.75-1.64 (m, 1H), 1.64-1.54 (m, 1H).

Step 4: N-(1-(4-Bromo-6-fluoropyridin-3-yl)pent-4-en-1-yl)-4-methoxyaniline 1-2e was synthesised from 1-(4-bromo-6-fluoropyridin-3-yl)pent-4-en-1-amine 1-2d using a procedure essentially the same as for 1-1e. LCMS (method 1) m/z 365.0, 367.1 $(M+H)^+$ $(ES^+)$, at 1.76 min. $^1H$ NMR (500 MHz, DMSO-d6) δ 8.21 (s, 1H), 7.61 (d, J=2.5 Hz, 1H), 6.66 (d, J=8.9 Hz, 2H), 6.40 (d, J=9.0 Hz, 2H), 6.04 (d, J=8.3 Hz, 1H), 5.86 (ddt, J=17.0, 10.2, 6.6 Hz, 1H), 5.08-4.90 (m, 2H), 4.59 (td, J=8.5, 4.8 Hz, 1H), 3.58 (s, 3H), 2.35-2.26 (m, 1H), 2.23-2.13 (m, 1H), 1.92-1.71 (m, 2H).

Step 5: A three-neck flask was charged with Pd-178 (0.29 g, 0.61 mmol) and $NaO^tBu$ (0.88 g, 9.2 mmol) and purged with $N_2$. A solution of N-(1-(4-bromo-6-fluoropyridin-3-yl)pent-4-en-1-yl)-4-methoxyaniline I-2e (2.3 g, 6.1 mmol) in toluene (66 ml) was added dropwise. The resulting mixture was heated to 95° C. for 2 h. The reaction mixture was cooled to RT and filtered through celite, washing the solid with EtOAc (150 ml). The filtrate was concentrated in vacuo. The product was purified by silica gel chromatography (0%-50% EtOAc/isohexane) to give a mixture of enantiomers which were dissolved to 30 mg/ml in DCM:methanol (1:4) and was then separated by chiral SFC on a Waters prep 15 with UV detection by at 210 nm, 40° C., 100 bar on a Lux $C_3$ column (21.2 mm×250 mm, 5 μm particle size), flow rate 50 $ml/min^{-1}$ using 40% methanol to give (6S,9R)-3-fluoro-10-(4-methoxyphenyl)-6,7,8,9-tetrahydro-5H-6,9-epiminocyclohepta[c]pyridine I-2f as a pale yellow oil. LCMS (method 1) m/z 285.3 $(M+H)^+$ $(ES^+)$, at 1.35 min. $^1H$ NMR (500 MHz, DMSO-d6) δ 8.10 (s, 1H), 6.79 (t, J=9.7 Hz, 3H), 6.70 (d, J=9.1 Hz, 2H), 4.95 (d, J=5.5 Hz, 1H), 4.47 (t, J=6.0 Hz, 1H), 3.61 (s, 3H), 3.11 (dd, J=18.2, 4.9 Hz, 1H), 2.31-2.19 (m, 2H), 1.88-1.55 (m, 2H), 1H obscured by residual DMSO peak.

Step 6: (6S,9R)-3-fluoro-6,7,8,9-tetrahydro-5H-6,9-epiminocyclohepta[c]pyridine I-2g was synthesised from (6S, 9R)-3-fluoro-10-(4-methoxyphenyl)-6,7,8,9-tetrahydro-5H-6,9-epiminocyclohepta[c]pyridine I-2f using a procedure essentially the same as for 1-1. LCMS (method 1) m/z 179.2 $(M+H)^+$ $(ES^+)$, at 0.71 min.

Step 7: (6S,9R)-3-fluoro-6,7,8,9-tetrahydro-5H-6,9-epiminocyclohepta[c]pyridine I-2g (300 mg, 1.68 mmol) was dissolved in HBr (48% w/w in water, 1.90 ml, 16.8 mmol) and was heated at 100° C. for 18 h. The reaction mixture was cooled to RT, diluted with MeOH, loaded onto a SCX cartridge (20 g) and the product was eluted with $NH_3$ in MeOH solution (0.7M) to give (6S,9R)-2,5,6,7,8,9-hexahydro-3H-6,9-epiminocyclohepta[c]pyridin-3-one 1-2 as an off white solid. LCMS (method 1) m/z 176.9 $(M+H)^+$ $(ES^+)$, at 0.41 min Intermediate 3 (I-3)

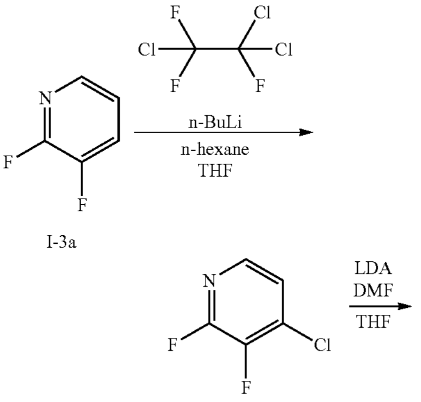

I-3a I-3b

-continued

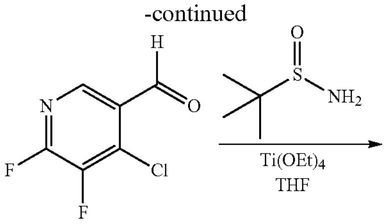

I-3c

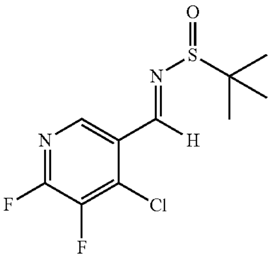

I-3d

I-3d

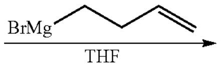

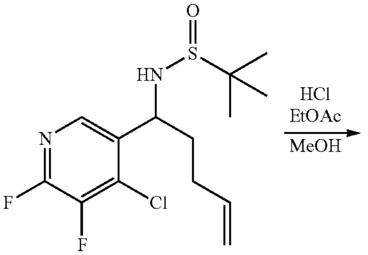

I-3e

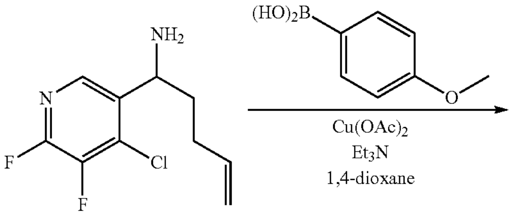

I-3f

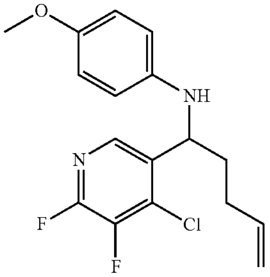

I-3g

I-3g

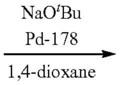

-continued

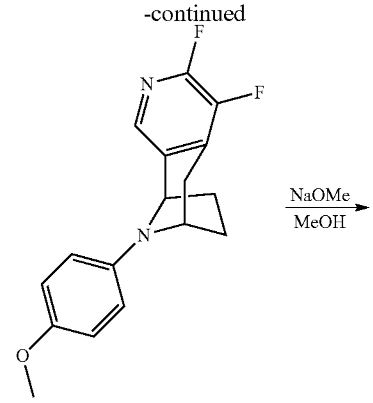

I-3h

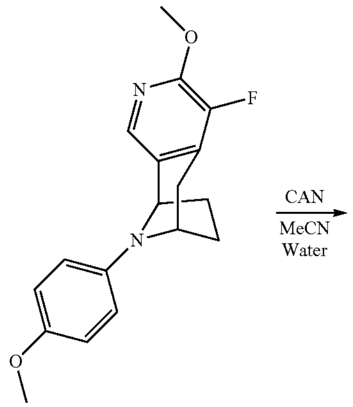

I-3i

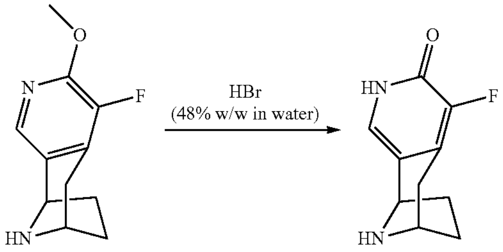

I-3j

I-3

Step 1: To a solution of 2,3-difluoropyridine I-3a (50.0 g, 434 mmol) in hexane (275 ml) and THF (450 ml) was added n-BuLi (2.5 M in hexane, 173 ml) at −70° C. The mixture was stirred at −70° C. for 2 h before 1,1,2-trichloro-1,2,2-trifluoroethane (52 ml, 434 mmol) was added at −70° C. and the resultant mixture was stirred at −70° C. for 1 h. Aqueous ammonium chloride solution (300 ml) was added at 0° C. and the product was extracted with EtOAc (3×100 ml). The combined organics were washed with brine (100 ml), dried with sodium sulfate and concentrated in vacuo to afford 4-chloro-2,3-difluoropyridine I-3b as a yellow oil. $^1$H NMR (400 MHz, $CDCl_3$) δ 7.92 (d, J=5.2 Hz, 1H), 7.29 (d, J=2.0 Hz, 1H).

Step 2: To a solution of 4-chloro-2,3-difluoropyridine I-3b (17 g, 113 mmol) in THF (170 ml) was added a solution of LDA in THF/n-heptane/ethylbenzene (2 M, 68 ml) at −90° C. The mixture was warmed −70° C. for 2 h. DMF (10.5 ml, 136 mmol) in THF (170 ml) was added slowly at −90° C. The resultant mixture was slowly warmed to RT and stirred at RT for 1 h. An aqueous 1M HCl solution (200 ml) was added at 0° C. The product was extracted with MTBE (3×100 ml). The combined organics were washed with brine (100 ml), dried over sodium sulfate and concentrated in vacuo to give 4-chloro-5,6-difluoronicotinaldehyde I-3c as a yellow oil. $^1$H NMR (400 MHz, $CDCl_3$) δ 10.3 (s, 1H), 8.52 (s, 1H).

Step 3: (E)-N-((4-Chloro-5,6-difluoropyridin-3-yl)methylene)-2-methylpropane-2-sulfinamide I-3d was synthesised from 4-chloro-5,6-difluoronicotinaldehyde I-25c using a procedure essentially the same as for I-1b. $^1$H NMR (400 MHz, $CDCl_3$) δ 8.89 (d, J=2.4 Hz, 1H), 8.64 (s, 1H), 1.31 (s, 9H).

Step 4: N-(1-(4-Chloro-5,6-difluoropyridin-3-yl)pent-4-en-1-yl)-2-methylpropane-2-sulfinamide 1-3e was synthesised from (E)-N-((4-chloro-5,6-difluoropyridin-3-yl)methylene)-2-methylpropane-2-sulfinamide I-3d using a procedure essentially the same as for 1-1c. $^1$H NMR (400 MHz, $CDCl_3$) δ 8.00 (s, 1H), 5.81-5.76 (m, 1H), 5.09-4.99 (m, 2H), 4.84-4.68 (m, 1H), 3.73-3.56 (m, 1H), 2.13-2.11 (m, 2H), 2.00-1.97 (m, 2H), 1.17 (s, 9H).

Step 5 To a solution of compound N-(1-(4-chloro-5,6-difluoropyridin-3-yl)pent-4-en-1-yl)-2-methylpropane-2-sulfinamide 1-3e (10.0 g, 29.6 mmol) in MeOH (60.0 ml) was added HCl/EtOAc (4 M, 22.2 ml) at 0° C. The mixture was warmed to RT for 1 h. The reaction mixture was concentrated in vacuo. The residue was triturated with MTBE (50.0 ml) at RT for 30 min. The mixture was filtered. The filter cake was washed with MTBE (2×50 ml) and dried in vacuo to give a yellow solid. The yellow solid was dissolved in water (50 ml) and The mixture was basified to pH >11 with NaOH solution at 0° C. and the product was extracted with DCM (3×50 ml). The combined organic layers were washed with brine (50.0 ml), dried over anhydrous sodium sulfate and concentrated in vacuo to 1-(4-chloro-5,6-difluoropyridin-3-yl)pent-4-en-1-amine I-25f) as a yellow oil. $^1$H NMR (400 MHz, $CDCl_3$) δ 8.11 (s, 1H), 5.84-5.76 (m, 1H), 5.06-4.98 (m, 2H), 4.33-4.30 (m, 1H), 2.18-2.12 (m, 2H), 1.85-1.73 (m, 2H).

Step 6: N-(1-(4-Chloro-5,6-difluoropyridin-3-yl)pent-4-en-1-yl)-4-methoxyaniline 1-3 g was synthesised from 1-(4-chloro-5,6-difluoropyridin-3-yl)pent-4-en-1-amine 1-3f using a procedure essentially the same as for I-1e. $^1$H NMR (400 MHz, $CDCl_3$) δ 8.00 (s, 1H), 6.71-6.69 (m, 2H), 6.42-6.39 (m, 2H), 5.84-5.79 (m, 1H), 5.08-5.03 (m, 2H), 4.67-4.65 (m, 1H), 3.70 (s, 3H), 2.29-2.20 (m, 2H), 1.95-1.86 (m, 2H).

Step 7: To a solution of N-(1-(4-chloro-5,6-difluoropyridin-3-yl)pent-4-en-1-yl)-4-methoxyaniline 1-3 g (0.30 g, 885 μmol) in 1,4-dioxane (10 ml) was added NaO$^t$Bu (127 mg, 1.32 mmol) and Pd-178 (42 mg, 88.5 mol) at RT. The resultant mixture was heated at 95° C. for 16 h. The reaction mixture was filtered. The filter cake was washed with EtOAc (3×10 ml), the combined organics were dried over sodium sulfate and concentrated in vacuo. The product was purified by chromatography on silica (1-100%, EtOAc/Petroleum ether) to afford (±)-3,4-difluoro-10-(4-methoxyphenyl)-6,7,8,9-tetrahydro-5H-6,9-epiminocyclohepta[c]pyridine I-3h as a yellow solid. $^1$H NMR (400 MHz, $CDCl_3$) δ 7.79 (s, 1H), 6.74-6.70 (m, 4H), 4.80-4.78 (m, 1H), 4.52-4.49 (m, 1H), 3.71 (s, 3H), 3.17-3.13 (m, 1H), 2.55-2.38 (m, 2H), 1.96-1.91 (m, 1H), 1.75-1.70 (m, 1H).

Step 8: To a solution of (±)-3,4-difluoro-10-(4-methoxyphenyl)-6,7,8,9-tetrahydro-5H-6,9-epiminocyclohepta[c]pyridine I-3h (145 mg, 480 μmol) in MeOH (5 ml) was added a solution of sodium methoxide in MeOH (133 μl, 5.4 M, 719 μmol). The reaction mixture was heated to 65° C. for 18 h. The reaction mixture was diluted with MeOH (5 ml) and an additional portion of sodium methoxide in MeOH (133 μl, 5.4 M, 719 μmol) was added and the reaction mixture was stirred at 65° C. for a further 3 h. The reaction mixture was diluted with DCM (30 ml) and water (10 ml) was added and the layers were separated. The aqueous was extracted with DCM (3×20 ml) and the combined organic layer were dried over sodium sulfate and concentrated in vacuo to give (±)-4-fluoro-3-methoxy-10-(4-methoxyphenyl)-6,7,8,9-tetrahydro-5H-6,9-epiminocyclohepta[c]pyridine I-3i as a brown oil. $^1$H NMR (500 MHz, DMSO-$d_6$) δ 7.88 (s, 1H), 6.84-6.78 (m, 2H), 6.73-6.68 (m, 2H), 4.92 (d, J=5.3 Hz, 1H), 4.51 (t, J=5.9 Hz, 1H), 3.85 (s, 3H), 3.61 (d, J=2.4 Hz, 3H), 2.97 (dd, J=18.0, 5.0 Hz, 1H), 2.46 (s, 1H), 2.25 (q, J=6.5, 4.5 Hz, 2H), 1.88-1.70 (m, 2H).

Step 9: (±)-4-Fluoro-3-methoxy-6,7,8,9-tetrahydro-5H-6,9-epiminocyclohepta[c]pyridine I-3j was synthesised from (±)-4-fluoro-3-methoxy-10-(4-methoxyphenyl)-6,7,8,9-tetrahydro-5H-6,9-epiminocyclohepta[c]pyridine I-3i using a procedure essentially the same as for 1-1. $^1$H NMR (500 MHz, DMSO-$d_6$) δ 7.66 (s, 1H), 4.20 (d, J=4.9 Hz, 1H), 3.87 (s, 3H), 3.73 (t, J=5.9 Hz, 1H), 2.88 (dd, J=17.6, 5.2 Hz, 1H), 2.70 (s, 1H), 2.53 (d, J=1.3 Hz, 1H), 1.95-1.86 (m, 2H), 1.74-1.64 (m, 1H), 1.54-1.44 (m, 1H).

Step 10: A solution of (±)-4-fluoro-3-methoxy-6,7,8,9-tetrahydro-5H-6,9-epiminocyclohepta[c]pyridine I-3j (190 mg, 999 μmol) in aqueous HBr (2.8 M, 48% Wt, 25.0 mmol) was refluxed for 16 h. The reaction mixture was concentrated in vacuo. The residue was dissolved in MeOH, loaded onto a SCX cartridge (10 g), the cartridge was washed with MeOH and the product was eluted with 0.7 M ammonia in MeOH solution. The filtrate was concentrated in vacuo to afford (±)-2,5,6,7,8,9-hexahydro-3H-6,9-epiminocyclohepta[c]pyridin-3-one 1-3 as a brown solid. LCMS (method 1) m/z 177.2 $(M+H)^+$ $(ES^+)$, at 0.40 min. $^1$H NMR (500 MHz, DMSO-$d_6$) δ 11.07 (s, 1H), 7.02 (s, 1H), 6.00 (s, 1H), 4.01 (d, J=5.5 Hz, 1H), 3.60 (t, J=6.1 Hz, 1H), 2.82 (dd, J=17.6, 5.1 Hz, 1H), 2.42-2.34 (m, 1H), 1.90-1.77 (m, 2H), 1.63-1.55 (m, 1H), 1.48-1.39 (m, 1H).

Experimental Scheme 2

Compound 21 (5R,8S)-1-fluoro-N-(4-methyl-1,2,5-oxadiazol-3-yl)-6,7,8,9-tetrahydro-5H-5,8-epiminocyclohepta[c]pyridine-10-carboxamide

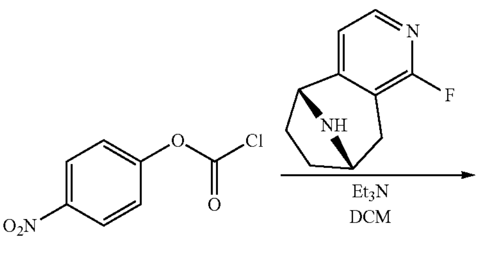

-continued

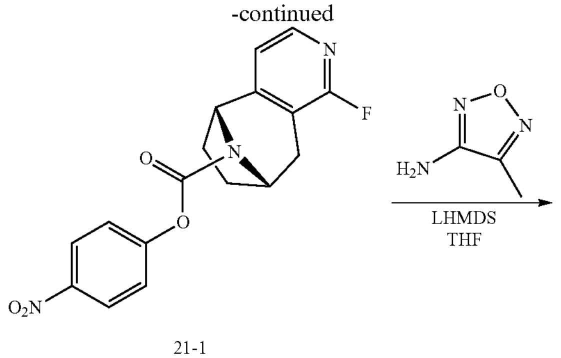

21-1

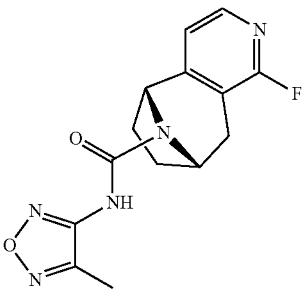

21

Step 1: To a solution of (5R,8S)-1-fluoro-6,7,8,9-tetrahydro-5H-5,8-epiminocyclohepta[c]pyridine 1-1 (800 mg, 4.49 mmol) in DCM (10 ml) and triethylamine (1.56 ml, 11.2 mmol) at 0° C. was added 4-nitrophenyl carbonochloridate (1.36 g, 6.73 mmol) as a single portion. The reaction mixture was warmed to RT over 30 min. Water (20 ml) was added and the layers were separated. The aqueous was further extracted with DCM (2×10 ml). The combined organics were washed with water (20 ml), dried over sodium sulfate and concentrated in vacuo. The product was purified by chromatography on silica gel (0-80% EtOAc/isohexane) to afford 4-nitrophenyl (5R,8S)-1-fluoro-6,7,8,9-tetrahydro-5H-5,8-epiminocyclohepta[c]pyridine-10-carboxylate 21-1 as a brown powder $^1$H NMR (500 MHz, DMSO-$d_6$) δ 8.25 (d, J=8.3 Hz, 2H), 8.05 (s, 1H), 7.48 (d, J=8.6 Hz, 1H), 7.37 (d, J=8.5 Hz, 1H), 7.30 (d, J=4.9 Hz, 1H), 5.26 (dd, J=111.5, 6.2 Hz, 1H), 4.75 (d, J=81.7 Hz, 1H), 3.30-3.11 (m, 1H), 2.70 (t, J=15.4 Hz, 1H), 2.42-2.18 (m, 2H), 1.91 (d, J=10.1 Hz, 1H), 1.80 (br s, 1H). Compound is rotameric in NMR Step 2: A solution of 4-nitrophenyl (5R,8S)-1-fluoro-6,7,8,9-tetrahydro-5H-5,8-epiminocyclohepta[c]pyridine-10-carboxylate 21-1 (34 mg, 0.1 mmol) in THF (0.5 ml) was added to 4-methyl-1,2,5-oxadiazol-3-amine (20 mg, 0.2 mmol). A solution of LHMDS in THF (0.2 ml, 1 M) was added and the reaction was stirred at RT for 16 h. The reaction mixture was concentrated and purified by mass directed HPLC (5-20% MeCN/10 mM aqueous ammonium hydroxide solution) to give (5R,8S)-1-fluoro-N-(4-methyl-1,2,5-oxadiazol-3-yl)-6,7,8,9-tetrahydro-5H-5,8-epiminocyclohepta[c]pyridine-10-carboxamide as an off white solid. LC-MS (method 1) m/z 304.2 $(M+H)^+$ $(ES)^+$ at 0.78 min, $^1$H NMR (400 MHz, DMSO-d6) δ 9.37 (s, 1H), 8.00 (d, J=5.0 Hz, 1H), 7.18 (dd, J=5.0, 1.7 Hz, 1H), 5.20 (d, J=5.8 Hz, 1H), 4.74 (t, J=6.1 Hz, 1H), 3.20 (dd, J=17.5, 5.1 Hz, 1H), 2.59 (s, 1H), 2.29-2.09 (m, 2H), 2.07 (s, 3H), 1.90-1.77 (m, 1H), 1.74 (dd, J=10.5, 5.5 Hz, 1H).

The following compounds were prepared using appropriate starting materials in an analogous procedure to that described in Experimental Scheme 2. Where the starting materials are not described in the literature, their synthesis is described below.

| Compound | Structure | LCMS method 1 Rt [M + H]$^+$ | NMR |
|---|---|---|---|
| 22 | 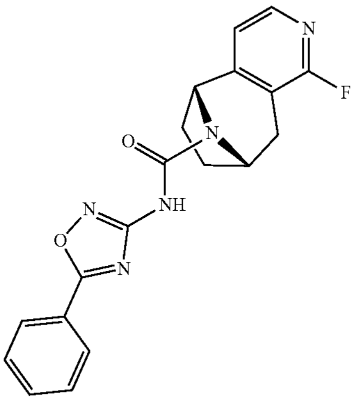 (5R,8S)-1-Fluoro-N-(5-phenyl-1,2,4-oxadiazol-3-yl)-6,7,8,9-tetrahydro-5H-5,8-epiminocyclohepta[c]pyridine-10-carboxamide | 366.5 at 1.03 min | $^1$H NMR (400 MHz, DMSO-d6) δ 10.00 (s, 1H), 8.17-7.90 (m, 3H), 7.81-7.66 (m, 1H), 7.66-7.53 (m, 2H), 7.21 (dd, J = 5.0, 1.6 Hz, 1H), 5.30 (d, J = 5.6 Hz, 1H), 4.84 (s, 1H), 3.17 (dd, J = 17.5, 5.0 Hz, 1H), 2.59 (d, J = 17.3 Hz, 1H), 2.19 (qd, J = 12.5, 11.5, 8.2 Hz, 2H), 1.96-1.79 (m, 1H), 1.74 (dt, J = 9.4, 4.9 Hz, 1H). |

-continued

| Compound | Structure | LCMS method 1 Rt [M + H]$^+$ | NMR |
| --- | --- | --- | --- |
| 23 | 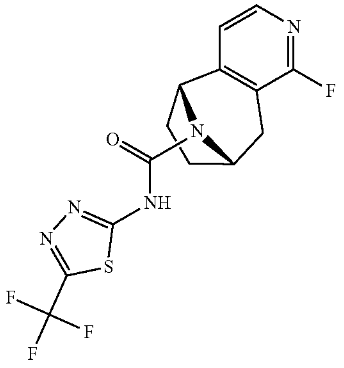 (5R,8S)-1-Fluoro-N-(5-(trifluoromethyl)-1,3,4-thiadiazol-2-yl)-6,7,8,9-tetrahydro-5H-5,8-epiminocyclohepta[c]pyridine-10-carboxamide | 374.2 at 0.68 min | $^1$H NMR (400 MHz, DMSO-d6) δ 12.37 (s, 1H), 8.02 (d, J = 5.0 Hz, 1H), 7.22 (dd, J = 5.1, 1.7 Hz, 1H), 5.40 (s, 1H), 4.94 (s, 1H), 3.14 (dd, J = 17.7, 5.0 Hz, 1H), 2.62 (d, J = 17.4 Hz, 1H), 2.37-2.18 (m, 2H), 2.02-1.79 (m, 1H), 1.79-1.70 (m, 1H). |
| 24 | 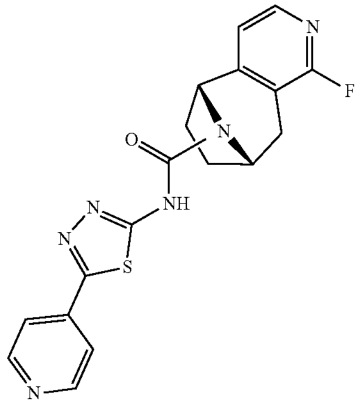 (5R,8S)-1-Fluoro-N-(5-(pyridin-4-yl)-1,3,4-thiadiazol-2-yl)-6,7,8,9-tetrahydro-5H-5,8-epiminocyclohepta[c]pyridine-10-carboxamide | 383.2 at 0.59 min | $^1$H NMR (400 MHz, DMSO-d6) δ 12.05 (s, 1H), 8.73-8.65 (m, 2H), 8.03 (d, J = 5.0 Hz, 1H), 7.87-7.76 (m, 2H), 7.23 (dd, J = 5.1, 1.6 Hz, 1H), 5.42 (s, 1H), 4.95 (s, 1H), 3.19-3.08 (m, 1H), 2.63 (d, J = 17.5 Hz, 1H), 2.35-2.14 (m, 2H), 1.88 (t, J = 9.8 Hz, 1H), 1.83-1.69 (m, 1H). |
| 25 | 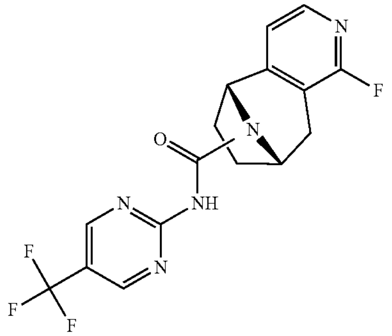 (5R,8S)-1-Fluoro-N-(5-(trifluoromethyl)pyrimidin-2-yl)-6,7,8,9-tetrahydro-5H-5,8-epiminocyclohepta[c]pyridine-10-carboxamide | 368.2 at 0.97 min | $^1$H NMR (400 MHz, DMSO-d6) δ 9.47 (s, 1H), 8.80 (s, 2H), 7.99 (d, J = 5.0 Hz, 1H), 7.34-7.08 (m, 1H), 5.20 (d, J = 5.6 Hz, 1H), 4.74 (s, 1H), 3.15 (dd, J = 17.3, 5.0 Hz, 1H), 2.58 (d, J = 17.2 Hz, 1H), 2.27-2.08 (m, 2H), 1.91-1.77 (m, 1H), 1.77-1.65 (m, 1H). |

-continued

| Compound | Structure | LCMS method 1 Rt [M + H]$^+$ | NMR |
|---|---|---|---|
| 26 | 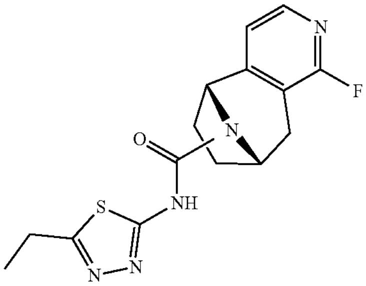 (5R,8S)-N-(5-Ethyl-1,3,4-thiadiazol-2-yl)-1-fluoro-6,7,8,9-tetrahydro-5H-5,8-epiminocyclohepta[c]pyridine-10-carboxamide | 334.2 at 0.60 min | $^1$H NMR (400 MHz, DMSO-d6) δ 11.73 (s, 1H), 8.01 (d, J = 5.0 Hz, 1H), 7.20 (dd, J = 5.0, 1.6 Hz, 1H), 5.35 (s, 1H), 4.87 (s, 1H), 3.11 (dd, J = 17.5, 5.0 Hz, 1H), 2.86 (q, J = 7.5 Hz, 2H), 2.59 (d, J = 17.3 Hz, 1H), 2.19 (ddd, J = 17.3, 13.3, 8.3 Hz, 2H), 1.89-1.79 (m, 1H), 1.74 (dt, J = 9.4, 5.0 Hz, 1H), 1.23 (t, J = 7.5 Hz, 3H). |
| 31 | 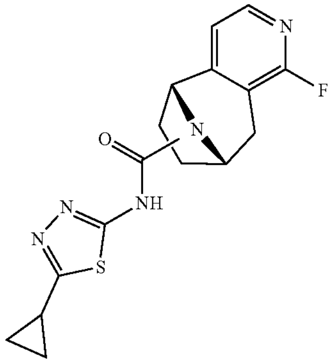 (5R,8S)-N-(5-Cyclopropyl-1,3,4-thiadiazol-2-yl)-1-fluoro-6,7,8,9-tetrahydro-5H-5,8-epiminocyclohepta[c]pyridine-10-carboxamide | 346.1 at 0.65 min | $^1$H NMR (400 MHz, DMSO) δ 11.55 (s, 1H), 8.01 (d, J = 5.0 Hz, 1H), 7.20 (dd, J = 5.0, 1.6 Hz, 1H), 5.35 (s, 1H), 4.87 (s, 1H), 3.10 (dd, J = 17.3, 5.0 Hz, 1H), 2.59 (d, J = 17.4 Hz, 1H), 2.32-2.10 (m, 3H), 1.90-1.81 (m, 1H), 1.80-1.69 (m, 1H), 1.12-1.00 (m, 2H), 0.94-0.83 (m, 2H) |
| 32 | 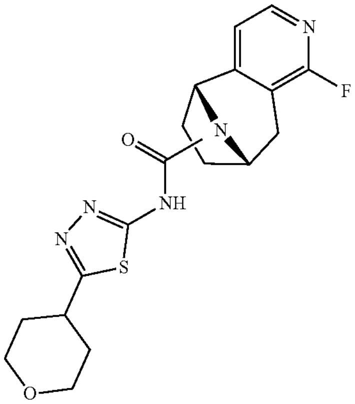 (5R,8S)-1-Fluoro-N-(5-(tetrahydro-2H-pyran-4-yl)-1,3,4-thiadiazol-2-yl)-6,7,8,9-tetrahydro-5H-5,8-epiminocyclohepta[c]pyridine-10-carboxamide | 390.3 at 0.61 min | $^1$H NMR (400 MHz, DMSO) δ 11.66 (s, 1H), 8.01 (d, J = 5.0 Hz, 1H), 7.20 (dd, J = 5.1, 1.6 Hz, 1H), 5.36 (s, 1H), 4.88 (s, 1H), 3.88 (ddd, J = 11.5, 4.3, 2.2 Hz, 2H), 3.43 (td, J = 11.6, 2.2 Hz, 2H), 3.27-3.06 (m, 2H), 2.59 (d, J = 17.3 Hz, 1H), 2.19 (ddd, J = 17.2, 13.3, 8.3 Hz, 2H), 1.94-1.81 (m, 3H), 1.80-1.61 (m, 3H). |

-continued

| Compound | Structure | LCMS method 1 Rt [M + H]+ | NMR |
|---|---|---|---|
| 33 | 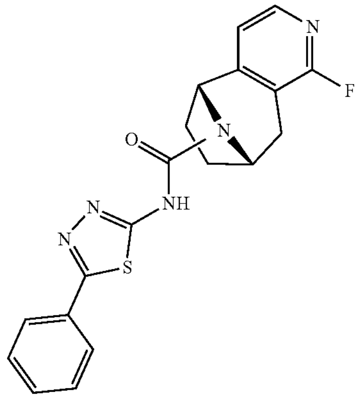<br>(5R,8S)-1-Fluoro-N-(5-phenyl-1,3,4-thiadiazol-2-yl)-6,7,8,9-tetrahydro-5H-5,8-epiminocyclohepta[c]pyridine-10-carboxamide | 382.2 at 0.74 min | $^1$H NMR (400 MHz, DMSO-d6) δ 11.79 (s, 1H), 8.03 (d, J = 5.0 Hz, 1H), 7.89-7.81 (m, 2H), 7.54-7.45 (m, 3H), 7.23 (dd, J = 5.0, 1.6 Hz, 1H), 5.41 (s, 1H), 4.94 (s, 1H), 3.15 (dd, J = 17.1, 5.0 Hz, 1H), 2.63 (d, J = 17.4 Hz, 1H), 2.30-2.13 (m, 2H), 1.88 (dd, J = 11.0, 8.7 Hz, 1H), 1.82-1.72 (m, 1H). |
| 34 | 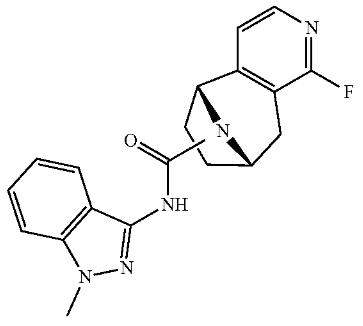<br>(5R,8S)-1-Fluoro-N-(1-methyl-1H-indazol-3-yl)-6,7,8,9-tetrahydro-5H-5,8-epiminocyclohepta[c]pyridine-10-carboxamide | 352.2 at 1.10 min | $^1$H NMR (400 MHz, DMSO-d6) δ 9.28 (s, 1H), 8.02 (d, J = 5.0 Hz, 1H), 7.53-7.48 (m, 1H), 7.48-7.42 (m, 1H), 7.33 (ddd, J = 8.3, 6.8, 1.1 Hz, 1H), 7.198.0, 6.8, 0.9 Hz, (dd, J = 5.0, 1.7 Hz, 1H), 6.99 (ddd, J = 1H), 5.27 (d, J = 5.8 Hz, 1H), 4.81 (t, J = 6.1 Hz, 1H), 3.91 (s, 3H), 3.23 (dd, J = 17.4, 5.1 Hz, 1H), 2.58 (d, J = 17.4 Hz, 1H), 2.31-2.16 (m, 2H), 1.92-1.82 (m, 1H), 1.82-1.72 (m, 1H). |

Experimental Scheme 3

Compound 27 (5R,8S)—N-(2-(difluoromethyl)-2H-pyrazolo[3,4-c]pyridin-5-yl)-1-fluoro-6,7,8,9-tetrahydro-5H-5,8-epiminocyclohepta[c]pyridine-10-carboxamide

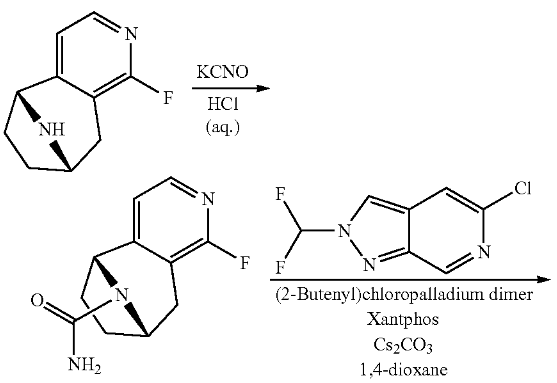

27-1

-continued

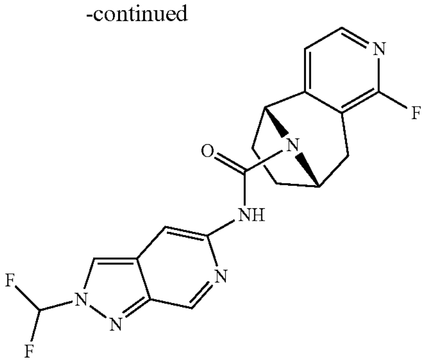

27

Step 1: To a solution of (5R,8S)-1-fluoro-6,7,8,9-tetrahydro-5H-5,8-epiminocyclohepta[c]pyridine (407 mg, 2.28 mmol) in HCl (3.9 ml, 1 M, 3.88 mmol) was added potassium cyanate (408 mg, 5.02 mmol) as a single portion and the reaction was stirred at RT for 72 h. A further portion of potassium cyanate (130 mg, 1.60 mmol) was added and stirring was continued for 3 h. The reaction mixture was filtered, and the precipitate was dried in vacuo to provide (5R,8S)-1-fluoro-6,7,8,9-tetrahydro-5H-5,8-epiminocyclohepta[c]pyridine-10-carboxamide as an off white powder. LC-MS (method 1) m/z 222.1 $(M+H)^+$ $(ES)^+$ at 0.64 min, $^1H$ NMR (500 MHz, DMSO-d6) δ 7.97 (d, J=5.0 Hz, 1H), 7.11 (dd, J=5.0, 1.7 Hz, 1H), 6.16 (s, 2H), 4.99 (d, J=6.2 Hz, 1H), 4.54-4.48 (m, 1H), 3.08 (dd, J=17.3, 5.0 Hz, 1H), 2.45 (d, J=17.3 Hz, 1H), 2.12 (dtd, J=23.8, 12.1, 7.0 Hz, 2H), 1.80-1.72 (m, 1H), 1.71-1.62 (m, 1H).

Step 2: (5R,8S)-1-fluoro-6,7,8,9-tetrahydro-5H-5,8-epiminocyclohepta[c]pyridine-10-carboxamide 27-1 (23.5 mg, 106 μmol), 5-chloro-2-(difluoromethyl)-2H-pyrazolo[3,4-c]pyridine (18.0 mg, 88.4 μmol), (2-Butenyl)chloropalladium dimer (0.8 mg, 2.21 μmol), xantphos (5 mg, 8.84 μmol) and caesium carbonate (72 mg, 221 μmol) were added to a vial. The vial was sealed, then evacuated/backfilled with $N_2$ (3 times). 1,4-Dioxane (1.5 ml) was added, and the reaction vessel was once more evacuated/backfilled with $N_2$ (3 times). The resultant mixture was heated to 90° C. for 16 h. The reaction mixture was cooled to RT and diluted with brine (2 ml), then extracted with EtOAc (3×10 ml). Combined organics were dried with magnesium sulfate and concentrated in vacuo. The product was purified by chromatography on silica gel (0-60% EtOAc/isohexane) to afford (5R,8S)—N-(2-(difluoromethyl)-2H-pyrazolo[3,4-c]pyridin-5-yl)-1-fluoro-6,7,8,9-tetrahydro-5H-5,8-epiminocyclohepta[c]pyridine-10-carboxamide) as a pale white powder. LC-MS (method 1) m/z 389.3 $(M+H)^+$ $(ES)^+$ at 1.26 min, $^1H$ NMR (500 MHz, DMSO-d6) δ 9.62 (s, 1H), 8.97 (d, J=1.2 Hz, 1H), 8.45 (d, J=0.8 Hz, 1H), 8.23 (d, J=1.3 Hz, 1H), 8.21 (t, $J_{H-F}$=56.0 Hz, 1H), 8.00 (d, J=5.1 Hz, 1H), 7.27-7.19 (m, 1H), 5.39 (d, J=5.8 Hz, 1H), 4.91 (s, 1H), 3.18 (dd, J=17.4, 4.9 Hz, 1H), 2.58 (d, J=17.4 Hz, 1H), 2.30-2.13 (m, 2H), 1.85 (t, J=9.3 Hz, 1H), 1.80-1.67 (m, 1H).

The following compounds were prepared using appropriate starting materials in an analogous procedure to that described in Experimental Scheme 3. Where the starting materials are not described in the literature, their synthesis is described below.

Intermediate 4 (I-4)

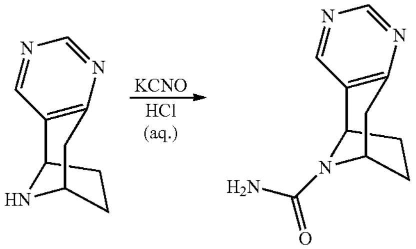

1-4a 1-4

(±)-6,7,8,9-tetrahydro-5H-5,8-epiminocyclohepta[d]pyrimidine-1-4 was synthesised from (±)-6,7,8,9-tetrahydro-5H-5,8-epiminocyclohepta[d]pyrimidine I-4a using a procedure essentially the same as for 27-1. $^1H$ NMR (500 MHz, Methanol-$d_4$) δ 8.91 (d, J=11.7 Hz, 1H), 8.51 (s, 1H), 5.11 (d, J=6.5 Hz, 1H), 4.63 (d, J=6.5 Hz, 1H), 3.50-3.36 (m, 1H), 2.74 (s, 1H), 2.45-2.19 (m, 2H), 1.95 (t, J=10.9 Hz, 1H), 1.85-1.70 (m, 1H). (2 exchangeable —NH protons not visible)

Intermediate 5 (I-5)

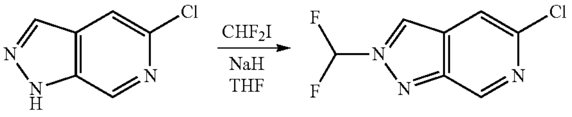

I-5a I-5

To a solution of sodium hydride (39 mg, 60% Wt, 0.98 mmol) in THF (0.5 ml) at 0° C. was added a solution of

| Compound | Structure | LCMS method 1 Rt [M + H]$^+$ | NMR |
|---|---|---|---|
| 28 | 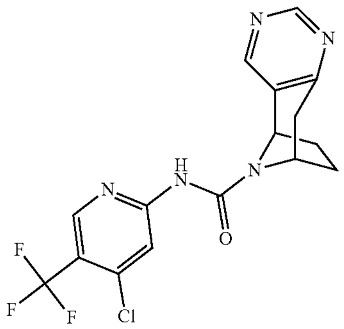 (±)-N-(4-Chloro-5-(trifluoromethyl)pyridin-2-yl)-6,7,8,9-tetrahydro-5H-5,8-epiminocyclohepta[d]pyrimidine-10-carboxamide | 384.4, 386.4 at 1.06 min | $^1H$ NMR (500 MHz, DMSO-d6) δ 11.83 (s, 1H), 9.77 (s, 1H), 8.44 (s, 1H), 8.14 (s, 1H), 7.10 (s, 1H), 5.24 (d, J = 6.0 Hz, 1H), 4.74 (s, 1H), 3.11-3.02 (m, 1H), 2.64 (d, J = 17.9 Hz, 1H), 2.13 (dd, J = 18.3, 8.0 Hz, 1H), 2.08 (dd, J = 11.7, 5.9 Hz, 1H), 1.78-1.64 (m, 2H). |

5-chloro-1H-pyrazolo[3,4-c]pyridine (50 mg, 0.33 mmol) in THF (0.5 ml). The reaction mixture was stirred for 5 min then warmed to RT. After 30 min, the reaction was cooled to 0° C. and difluoroiodomethane (in THF) (1.2 g, 10% Wt, 0.65 mmol) was added dropwise. The reaction warmed slowly to RT and stirred for 2 h. Water (2 ml) was added and the product was extracted with EtOAc (3×5 ml). The combined organics were dried with magnesium sulfate and concentrated in vacuo. The product was purified by chromatography on silica gel (0-10% EtOAc/isohexane) to afford 5-chloro-2-(difluoromethyl)-2H-pyrazolo[3,4-c]pyridine 1-5 as a yellow oil. $^1$H NMR (500 MHz, DMSO-d6) δ 9.16 (s, 1H), 8.56 (d, J=0.8 Hz, 1H), 8.32 (t, $J_{C-F}$=58.0 Hz, 1H), 8.09 (d, J=1.1 Hz, 1H)

Experimental Scheme 4

Compound 35 (5R,8S)—N-(Benzo[c][1,2,5]oxadiazol-5-yl)-1-fluoro-6,7,8,9-tetrahydro-5H-5,8-epiminocyclohepta[c]pyridine-10-carboxamide

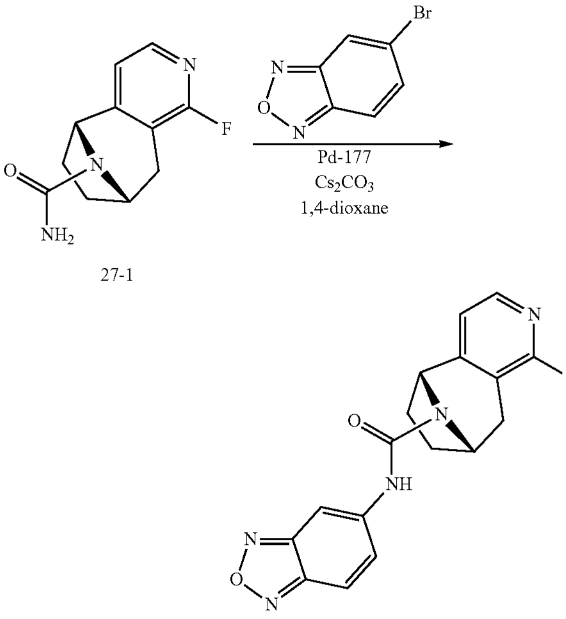

27-1

35

To a vial was added (5R,8S)-1-fluoro-6,7,8,9-tetrahydro-5H-5,8-epiminocyclohepta[c]pyridine-10-carboxamide (30 mg, 0.14 mmol), Pd-177 (5.2 mg, 6.8 μmol), 5-bromobenzo[c][1,2,5]oxadiazole (32 mg, 0.16 mmol) and cesium carbonate (0.11 g, 0.34 mmol). The vial was sealed, then evacuated/backfilled with $N_2$. 1,4-Dioxane (2.5 ml) was added, and the reaction vessel was once more evacuated/backfilled with $N_2$ and heated to 90° C. overnight. The mixture was cooled RT and diluted with brine (20 ml) and the product was extracted with EtOAc (2×30 ml). The combined organic layers were dried over $MgSO_4$, filtered and concentrated in vacuo. The product was purified by chromatography on silica gel [0-50% (10% MeOH in ethyl acetate) in isohexane] to afford (5R,8S)—N-(benzo[c][1,2,5]oxadiazol-5-yl)-1-fluoro-6,7,8,9-tetrahydro-5H-5,8-epiminocyclohepta[c]pyridine-10-carboxamide 35 as a pale brown solid. LC-MS (method 1) m/z 339.4 $(M+H)^+$ $(ES)^+$ at 1.24 min, $^1$H NMR (400 MHz, DMSO-d6) δ 9.28 (s, 1H), 8.08 (dd, J=1.8, 0.9 Hz, 1H), 8.02 (d, J=5.0 Hz, 1H), 7.96 (dd, J=9.6, 0.9 Hz, 1H), 7.64 (dd, J=9.7, 1.8 Hz, 1H), 7.24 (dd, J=5.0, 1.7 Hz, 1H), 5.31 (d, J=6.1 Hz, 1H), 4.89 (t, J=6.1 Hz, 1H), 3.25-3.08 (m, 1H), 2.63 (d, J=17.4 Hz, 1H), 2.37-2.09 (m, 2H), 1.96-1.83 (m, 1H), 1.83-1.70 (m, 1H).

Experimental Scheme 5

Compound 36 (5R,8S)-1-Fluoro-N-(5-(trifluoromethyl)isoxazol-3-yl)-6,7,8,9-tetrahydro-5H-5,8-epiminocyclohepta[c]pyridine-10-carboxamide

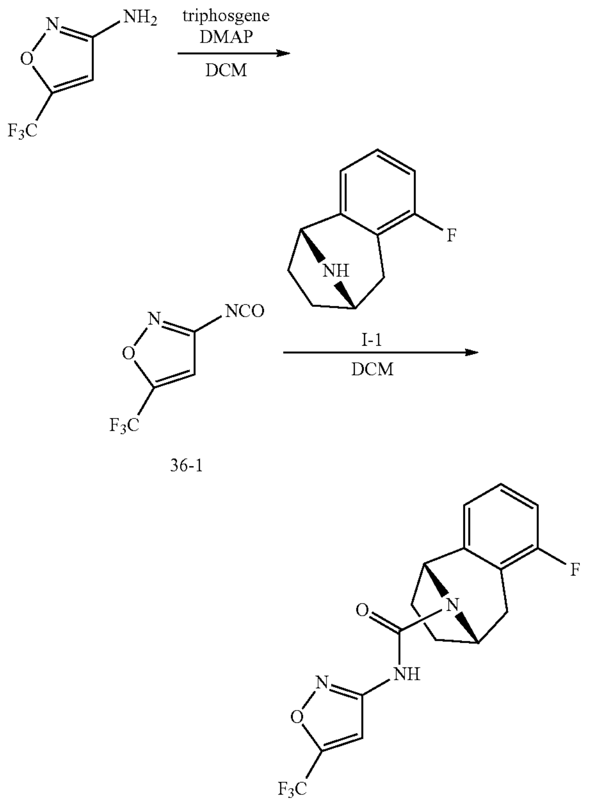

36-1

36

Step 1: To a solution of 5-(trifluoromethyl)isoxazol-3-amine (50 mg, 0.33 mmol) and triphosgene (50.4 mg, 0.17 mmol) in DCM (4 ml) at 0° C. was added a solution of DMAP (134.4 mg, 1.1 mmol) in DCM (1 ml). The mixture was stirred at RT for 30 min then used in the next step directly without any purification or analysis.

Step 2: To a solution of (5R,8S)-1-fluoro-6,7,8,9-tetrahydro-5H-5,8-epiminocyclohepta[c]pyridine 1-1 (58.8 mg, 0.33 mol) in DCM (1 ml) was added dropwise the isocyanate solution previously prepared (Step 1). The reaction was stirred at RT for 16 h. Water (10 ml) was added and the product was extracted with DCM (3×20 ml) and the combined organic layers dried over $Na_2SO4$ and concentrated in vacuo. The residue was purified by prep-TLC (1:2, EtOAc: petroleum ether) to give (5R,8S)-1fluoro-N-(5-(trifluoromethyl)isoxazol-3-yl)-6,7,8,9-tetrahydro-5H-5,8-epiminocyclohepta[c]pyridine-10-carboxamide as a white solid. LC-MS (method 3) m/z 357.1 $(M+H)^+$ $(ES)^+$ at 3.11 min, $^1$H NMR (400 MHz, DMSO-d6): δ 10.44 (s, 1H), 8.01 (d, J=4.8 Hz, 1H), 7.45 (s, 1H), 7.20 (d, J=6.4 Hz, 1H), 5.32 (d, J=5.6 Hz, 1H), 4.85 (s, 1H), 3.18 (dd, J=5.2, 4.8 Hz, 1H), 2.61 (d, J=17.2 Hz, 1H), 2.24-2.15 (m, 2H), 1.87-1.72 (m, 2H).

The following compounds were prepared using appropriate starting materials in an analogous procedure to that described in Experimental Scheme 3. Where the starting materials are not described in the literature, their synthesis is described below.

Key: (a) purified by prep-TLC (1:20, MeOH:DCM), (b) purified by prep-TLC (1:1, EtOAc: petroleum ether), (c) purified by prep-TLC (1:20, EtOAc:DCM), (d) purified by prep-TLC (1:30, EtOAc:DCM) (e) purified by chromatography on silica gel (0-100% (3:1 EtOAc/EtOH) in isohexane)) (f) purified by chromatography on silica gel (EtOAc/isohexane) (g) no ionisation in ($ES^+$) so ($ES^-$) data reported

| Compound | Structure | LCMS Rt $[M + H]^+$ | NMR |
|---|---|---|---|
| 37[(a)] | 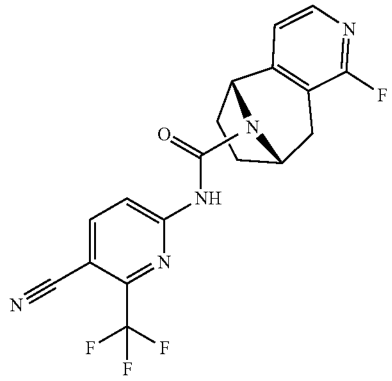 (5R,8S)-N-(5-Cyano-6-(trifluoromethyl)pyridin-2-yl)-1-fluoro-6,7,8,9-tetrahydro-5H-5,8-epiminocyclohepta[c]pyridine-10-carboxamide | 392.1 at 3.25 min Method 3 | $^1$H NMR (400 MHz, DMSO-d6): δ 10.51 (s, 1H), 8.36 (d, J = 8.8 Hz, 1H), 8.19 (d, J = 8.8 Hz, 1H), 8.01 (d, J = 5.2 Hz, 1H), 7.23-7.21 (m, 1H), 5.39 (s, 1H), 4.93 (s, 1H), 3.22-3.16 (m, 1H), 2.60 (d, J = 17.2 Hz, 1H), 2.27-2.13 (m, 2H), 1.87-1.83 (m, 1H), 1.77-1.73 (m, 1H). |
| 38[(b)] | 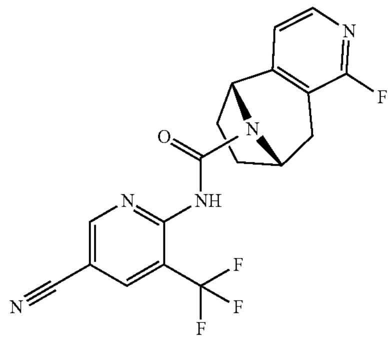 (5R,8S)-N-(5-Cyano-3-(trifluoromethyl)pyridin-2-yl)-1-fluoro-6,7,8,9-tetrahydro-5H-5,8-epiminocyclohepta[c]pyridine-10-carboxamide | 392.1 at 3.27 min Method 3 | $^1$H NMR (400 MHz, DMSO-d6): δ 10.64 (s, 1H), 8.99 (s, 1H), 8.38 (s, 1H), 8.01 (d, J = 5.2 Hz, 1H), 7.21 (d, J = 4.4 Hz, 1H), 5.39 (s, 1H), 4.94 (s, 1H), 3.21-3.15 (m, 1H), 2.61 (d, J = 17.2 Hz, 1H), 2.28-2.16 (m, 2H), 1.89-1.84 (m, 1H), 1.78-1.74 (m, 1H). |
| 39[(b)] | 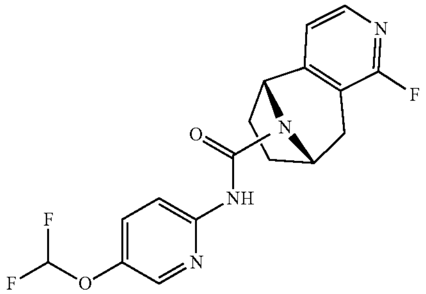 (5R,8S)-N-(5-(Difluoromethoxy)pyridin-2-yl)-1-fluoro-6,7,8,9-tetrahydro-5H-5,8-epiminocyclohepta[c]pyridine-10-carboxamide | 365.2 at 2.89 min Method 3 | $^1$H NMR (400 MHz, DMSO-d6): δ 9.57 (s, 1H), 8.14 (s, 1H), 8.01 (s, 1H), 7.85 (d, J = 9.2 Hz, 1H), 7.59-7.56 (m, 1H), 7.34-6.97 (m, 2H), 5.35 (s, 1H), 4.89-4.86 (m, 1H), 3.18-3.13 (m, 1H), 2.56 (d, J = 17.6 Hz, 1H), 2.26-2.14 (m, 2H), 1.89-1.84 (m, 1H), 1.81-1.68 (m, 1H). |

-continued

| Compound | Structure | LCMS Rt [M + H]+ | NMR |
|---|---|---|---|
| 40 | 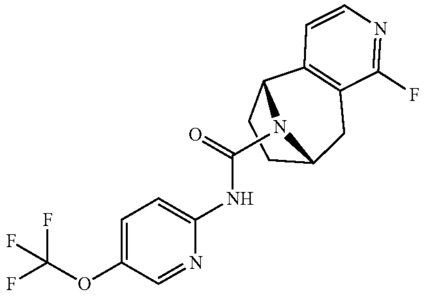 (5R,8S)-1-Fluoro-N-(5-(trifluoromethoxy)pyridin-2-yl)-6,7,8,9-tetrahydro-5H-5,8-epiminocyclohepta[c]pyridine-10-carboxamide | 383.1 at 3.25 min Method 3 | $^1$H NMR (400 MHz, DMSO-d6): δ 9.73 (s, 1H), 8.31 (d, J = 2.8 Hz, 1H), 8.00 (d, J = 4.8 Hz, 1H), 7.93-7.91 (m, 1H), 7.78-7.75 (m, 1H), 7.19 (t, J = 4.8 Hz, 1H), 5.35 (s, 1H), 4.88 (s, 1H), 3.16 (dd, J = 4.0 Hz, 17.6 Hz, 1H), 2.59-2.55 (m, 1H), 2.27-2.13 (m, 2H), 1.86-1.71 (m, 2H). |
| 41[(b)] | 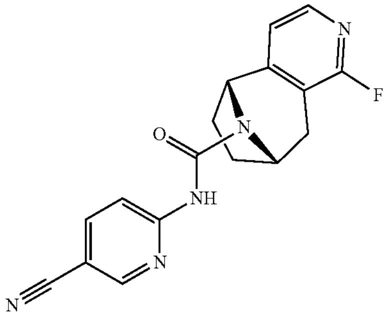 (5R,8S)-N-(5-Cyanopyridin-2-yl)-1-fluoro-6,7,8,9-tetrahydro-5H-5,8-epiminocyclohepta[c]pyridine-10-carboxamide | 324.1 at 2.67 min Method 3 | $^1$H NMR (400 MHz, DMSO-d6): δ 10.06 (s, 1H), 8.68 (d, J = 2.0 Hz, 1H), 8.09-7.95 (m, 3H), 7.20 (d, J = 4.8 Hz, 1H), 5.38 (s, 1H), 4.90 (s, 1H), 3.18 (dd, J = 5.2, 5.2 Hz, 1H), 2.60 (d, J = 17.6 Hz, 1H), 2.26-2.18 (m, 2H), 1.86-1.70 (m, 2H). |
| 42[(a)] | 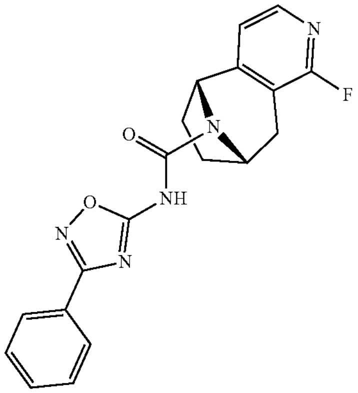 (5R,8S)-1-Fluoro-N-(3-phenyl-1,2,4-oxadiazol-5-yl)-6,7,8,9-tetrahydro-5H-5,8-epiminocyclohepta[c]pyridine-10-carboxamide | 366.1 at 2.89 min Method 3 | $^1$H NMR (400 MHz, DMSO-d6): δ 11.42 (s, 1H), 8.03 (d, J = 4.8 Hz, 1H), 7.94-7.91 (m, 2H), 7.57-7.52 (m, 3H), 7.23 (d, J = 5.2 Hz, 1H), 5.33-5.31 (m, 1H), 4.88-4.85 (m, 1H), 3.22-3.17 (m, 1H), 2.63 (d, J = 17.6 Hz, 1H), 2.27-2.19 (m, 2H), 1.89-1.85 (m. 1H), 1.79-1.73 (m, 1H). |
| 43 | 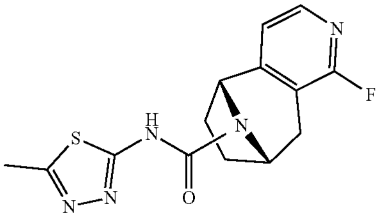 (5R,8S)-1-Fluoro-N-(5-methyl-1,3,4-thiadiazol-2-yl)-6,7,8,9-tetrahydro-5H-5,8-epiminocyclohepta[c]pyridine-10-carboxamide | 320.1 at 2.76 min Method 3 | $^1$H NMR (400 MHz, DMSO-d6): δ 11.57 (s, 1H), 8.01 (d, J = 5.2 Hz, 1H), 7.20 (d, J = 4.4 Hz, 1H), 5.36 (s, 1H), 4.89 (s, 1H), 3.11 (dd, J = 4.8, 17.2 Hz, 1H), 2.62-2.58 (m, 1H), 2.50 (s, 3H), 2.27-2.13 (m, 2H), 1.88-1.72 (m, 2H). |

-continued

| Compound | Structure | LCMS Rt [M + H]+ | NMR |
|---|---|---|---|
| 44[(b)] | 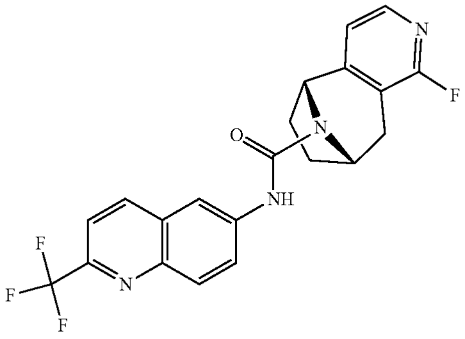 (5R,8S)-1-Fluoro-N-(2-(trifluoromethyl)quinolin-6-yl)-6,7,8,9-tetrahydro-5H-5,8-epiminocyclohepta[c]pyridine-10-carboxamide | 417.2 at 3.34 min Method 3 | $^1$H NMR (400 MHz, DMSO-d6): δ 9.27 (s, 1H), 8.51 (d. J = 8.8 Hz, 1H), 8.28 (s, 1H), 8.06-7.95 (m, 3H), 7.84 (d, J = 8.8 Hz, 1H), 7.23 (d, J = 4.0 Hz, 1H), 5.31 (d, J = 6.0 Hz, 1H), 4.89 (t, J = 5.2 Hz, 1H), 3.23-3.18 (m, 1H), 2.63 (d, J = 17.2 Hz, 1H), 2.33-2.20 (m, 2H), 1.91-1.76 (m, 2H) |
| 45[(a)] | 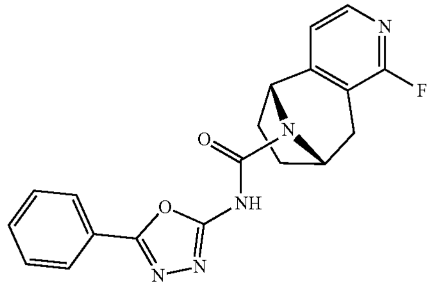 (5R,8S)-1-Fluoro-N-(5-phenyl-1,3,4-oxadiazol-2-yl)-6,7,8,9-tetrahydro-5H-5,8-epiminocyclohepta[c]pyridine-10-carboxamide | 366.1 at 2.77 min Method 3 | $^1$H NMR (400 MHz, DMSO-d6): δ 8.02 (d, J = 4.8 Hz, 1H), 7.88 (d, J = 7.6 Hz, 2H), 7.61-7.54 (m, 3H), 7.23 (d, J = 4.4 Hz, 1H), 5.27 (s, 1H), 4.82 (s, 1H), 3.18 (d, J = 17.2 Hz, 1H), 2.64 (d, J = 16.8 Hz, 1H), 2.29-2.17 (m, 2H), 1.88-1.74 (m, 3H) |
| 46[(c)] | 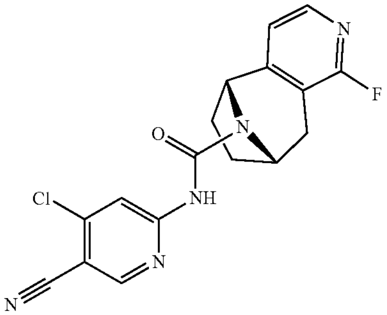 (5R,8S)-N-(4-Chloro-5-cyanopyridin-2-yl)-1-fluoro-6,7,8,9-tetrahydro-5H-5,8-epiminocyclohepta[c]pyridine-10-carboxamide | 358.1 at 3.1 min Method 3 | $^1$H NMR (400 MHz, DMSO-d6): δ 10.37 (s, 1H), 8.77 (s, 1H), 8.12 (s, 1H) 8.01 (d, J = 5.2 Hz, 1H), 7.21 (d, J = 5.2 Hz, 1H), 5.37 (s, 1H), 4.91 (s, 1H), 3.19 (dd, J1 = 5.2 Hz, J2 = 4.8 Hz, 1H), 2.61 (d, J = 17.2 Hz, 1H), 2.20-2.17 (m, 2H), 1.87-1.72 (m, 2H). |

-continued

| Compound | Structure | LCMS Rt [M + H]+ | NMR |
|---|---|---|---|
| 47(d) | 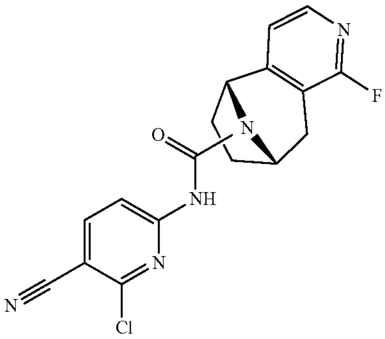 (5R,8S)-N-(6-Chloro-5-cyanopyridin-2-yl)-1-fluoro-6,7,8,9-tetrahydro-5H-5,8-epiminocyclohepta[c]pyridine-10-carboxamide | 358.1 at 3.82 min Method 4 | $^1$H NMR (400 MHz, DMSO-d6): δ 10.39 (s, 1H), 8.21 (d, J = 8.8 Hz, 1H), 8.01-7.93 (m, 3H), 7.21 (d, J = 6.0 Hz, 1H), 5.38 (s, 1H), 4.90 (s, 1H), 3.19 (dd, J = 5.2, 5.2 Hz, 1H), 2.60 (d, J = 17.6 Hz, 1H), 2.23-2.15 (m, 2H), 1.87-1.72 (m, 2H). |
| 49(e) | 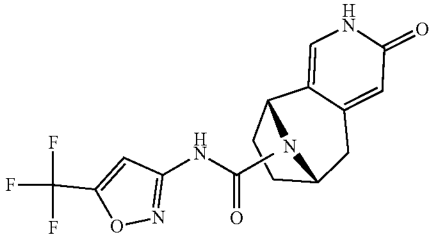 (6S,9R)-3-oxo-N-(5-(trifluoromethyl)isoxazol-3-yl)-3,5,6,7,8,9-hexahydro-2H-6,9-epiminocyclohepta[c]pyridine-10-carboxamide | 355.1, 356.5 at 1.0 min Method 1 | $^1$H NMR (400 MHz, DMSO) δ 11.27 (s, 1H), 10.28 (s, 1H), 7.47 (d, J = 1.0 Hz, 1H), 7.19 (s, 1H), 6.10 (s, 1H), 5.14 (d, J = 5.8 Hz, 1H), 4.71-4.56 (m, 1H), 3.08 (dd, J = 17.9, 5.1 Hz, 1H), 2.56 (d, J = 17.9 Hz, 1H), 2.22-2.00 (m, 2H), 1.78-1.58 (m, 2H). |
| 50(f) | 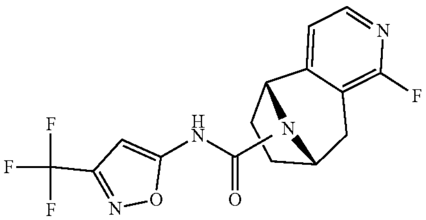 (5R,8S)-1-Fluoro-N-(3-(trifluoromethyl)isoxazol-5-yl)-6,7,8,9-tetrahydro-5H-5,8-epiminocyclohepta[c]pyridine-10-carboxamide | 355.2, 356.4(9) at 0.76 min | $^1$H NMR (400 MHz, DMSO) δ 11.16 (s, 1H), 8.02 (d, J = 4.6 Hz, 1H), 7.22 (dd, J = 5.0, 1.6 Hz, 1H), 6.42 (s, 1H), 5.31 (d, J = 5.9 Hz, 1H), 4.93-4.76 (m, 1H), 3.14 (dd, J = 17.8, 5.0 Hz, 1H), 2.62 (d, J = 17.4 Hz, 1H), 2.31-2.12 (m, 2H), 1.92-1.82 (m, 1H), 1.82-1.72 (m, 1H). |
| 51(f) | 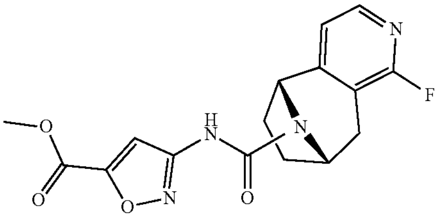 Methyl-3-((5R,8S)-1-fluoro-6,7,8,9-tetrahydro-5H-5,8-epiminocyclohepta[c]pyridine-10-carboxamido)isoxazole-5-carboxylate | 347 at 1.05 min Method 1 | $^1$H NMR (400 MHz, DMSO) δ 10.29 (s, 1H), 8.01 (d, J = 5.0 Hz, 1H), 7.31 (s, 1H), 7.20 (dd, J = 5.1, 1.6 Hz, 1H), 5.32 (d, J = 5.7 Hz, 1H), 4.86 (t, J = 6.4 Hz, 1H), 3.87 (s, 3H), 3.13 (dd, J = 17.4, 5.0 Hz, 1H), 2.59 (d, J = 17.4 Hz, 1H), 2.19 (ddd, J = 17.4, 13.7, 8.5 Hz, 2H), 1.92-1.80 (m, 1H), 1.77-1.74 (m, 1H). |

-continued

| Compound | Structure | LCMS Rt [M + H]$^+$ | NMR |
|---|---|---|---|
| 52[f] | 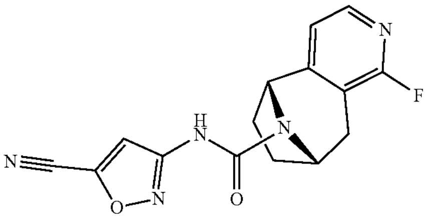 (5R,8S)-N-(5-Cyanoisoxazol-3-yl)-1-fluoro-6,7,8,9-tetrahydro-5H-5,8-epiminocyclohepta[c]pyridine-10-carboxamide | 311.8[g] at 1.01 min Method 1 | $^1$H NMR (400 MHz, DMSO) δ 10.48 (s, 1H), 8.01 (d, J = 5.0 Hz, 1H), 7.76 (s, 1H), 7.23-7.17 (m, 1H), 5.31 (d, J = 5.8 Hz, 1H), 4.85 (s, 1H), 3.12 (dd, J = 17.4, 5.0 Hz, 1H), 2.60 (d, J = 17.3 Hz, 1H), 2.27-2.14 (m, 2H), 1.93-1.81 (m, 1H), 1.76 (dd, J = 11.8, 5.6 Hz, 1H). |

Experimental Scheme 6

Compound 48: (5R,8S)-1-fluoro-N-(1-methyl-5-(trifluoromethyl)-1H-pyrazol-3-yl)-6,7,8,9-tetrahydro-5H-5,8-epiminocyclohepta[c]pyridine-10-carboxamide

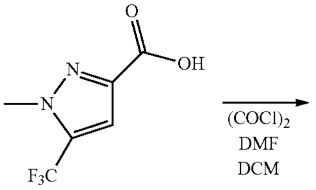

48-1

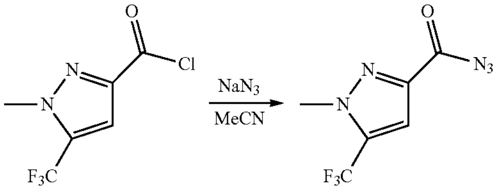

48-2 48-3

48-3 

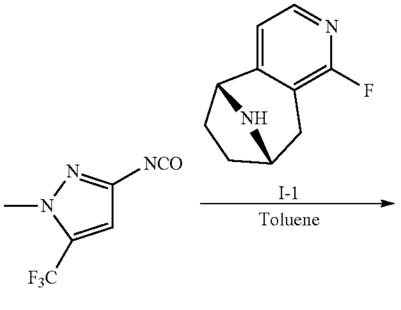

48-4

-continued

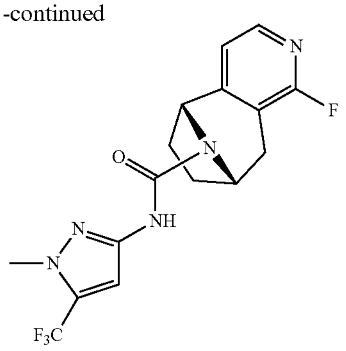

48

Step 1: To a solution of 1-methyl-5-(trifluoromethyl)-1H-pyrazole-3-carboxylic acid (200 mg, 1.03 mmol) in DCM (5 ml) was added oxalyl chloride (0.13 ml, 1.55 mmol) and one drop of DMF. The mixture was stirred at RT for 2 h then concentrated in vacuo to give 1-methyl-5-(trifluoromethyl)-1H-pyrazole-3-carbonyl chloride. The residue was used in the next step directly without any further purification or analysis Step 2: To a solution of 1-methyl-5-(trifluoromethyl)-1H-pyrazole-3-carbonyl chloride (219 mg, 1.03 mmol) in MeCN (5 ml) was added sodium azide (268 mg, 4.12 mmol). The mixture was stirred at RT for 16 h then was diluted with water (10 ml) and the product was extracted with DCM (20 ml). The combined organic layers were dried and the organics were concentrated in vacuo to afford 1-methyl-5-(trifluoromethyl)-1H-pyrazole-3-carbonyl azide, which was used without purification or analysis Step 3: To a solution of 1-methyl-5-(trifluoromethyl)-1H-pyrazole-3-carbonyl azide (226 mg, 1.03 mmol) in toluene (5 ml) was refluxed for 2 h. The reaction was cooled and the solution was used in the next step directly without any purification or analysis.

Step 4: To a solution of (5R,8S)-1-fluoro-6,7,8,9-tetrahydro-5H-5,8-epiminocyclohepta[c]pyridine 1-1 (184 mg, 1.03 mmol) in toluene (5 ml) was added dropwise the isocyanate solution previously prepared (Step 3). The reaction was stirred at RT for 16 h. Water (10 ml) was added and the product was extracted with DCM (2x20 ml). The combined organic layers were dried over $Na_2SO_4$ and concentrated in vacuo. The residue was purified by prep-TLC (1:2, EtOAc: petroleum ether) to give (5R,8S)-1-fluoro-N-(1-methyl-5-(trifluoromethyl)-1H-pyrazol-3-yl)-6,7,8,9-tetrahydro-5H-5,8-epiminocyclohepta[c]pyridine-10-carboxamide as a white solid. LC-MS (method 3) m/z 370.1 $(M+H)^+$ $(ES)^+$ at 2.91 min, $^1H$ NMR (400 MHz, DMSO-d6): δ 9.65 (s, 1H), 7.99 (d, J=5.2 Hz, 1H), 7.18-7.16 (m, 1H), 6.78 (s, 1H), 5.26 (d, J=5.6 Hz, 1H), 4.79 (s, 1H), 3.82 (s, 3H), 3.11 (dd, J=4.8, 17.2 Hz, 1H), 2.56 (s, 1H), 2.25-2.11 (m, 2H), 1.85-1.70 (m, 2H).

Human GPR65 Cyclic Adenosine Monophosphate (cAMP) Homogeneous Time Resolved Fluorescence (HTRF) Antagonist Assay Procedure $IC_{50}$ data was obtained by the following procedure:

1321N1 human astrocytoma cells stably expressing human recombinant GPR65 (1321N1-hrGPR65 cells, EuroscreenFast) were cultured according to the vendor's instructions.

Compounds were tested for their ability to antagonise GPR65, through measuring the concentration of cytoplasmic cAMP following treatment of the cells at a pH of 7.2 to activate GPR65 signalling and addition of the compound to be tested. The extent to which the expected rise in cAMP concentration upon GPR65 activation was suppressed by the added compound is indicative of its potency. The assay was carried out according to EuroscreenFast assay methodology as follows.

On the day of the assay, test compounds were added to 384-well, low volume, white microtiter plates by acoustic dispensing. KRH buffer (5 mM KCl, 1.25 mM $MgSO_4$, 124 mM NaCl, 25 mM HEPES, 13.3 mM Glucose, 1.25 mM $KH_2PO_4$ and 1.45 mM $CaCl_2$) was adjusted to pH 6.5, pH 7.6 and pH 8.4 by adding NaOH. 1321N1-hGPR65 cells were rapidly thawed and diluted in KRH, pH 7.6 prior to centrifugation at 300×g for 5 min and resuspension in assay buffer (KRH, pH 7.6, supplemented with 1 mM 3-isobutyl-1-methylxanthine (IBMX) and 200 μM ethylenediaminetetraacetic acid (EDTA)). Cells were added to assay plates at a density of 2,000 cells per well in a volume of 5 μl. Assay plates were briefly centrifuged at 100×g and then incubated at room temperature for 30 min. Cells were stimulated by the addition of 5 μL KRH, pH 6.5, to achieve an assay pH of 7.2, while control wells received 5 μl KRH, pH 8.4 to achieve an assay pH of 7.9. Assay plates were briefly centrifuged at 100×g and then incubated at room temperature for 30 min.

Accumulation of cAMP was detected by cAMP HTRF kit (Cisbio). d2-labeled cAMP and cryptate-labeled anti-cAMP antibody in Lysis and Detection Buffer (Cisbio) were added to assay plates, and the plates were incubated at room temperature for 1 h. HTRF measurements were performed using a Pherastar FSX instrument. Acceptor and donor emission signals were measured at 665 nm and 620 nm, respectively, and HTRF ratios were calculated as $signal_{665\,nm}/signal_{620\,nm} \times 10^4$. Data were normalised to high and low control values and fitted with 4-parameter logistic regression to determine hGPR65 IC50 values for the test compounds, which are shown in Table 1.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Activity of selected compounds according to the invention

| | |
|---|---|
| 1 | High |
| 2 | High |
| 3 | Medium |
| 4 | High |
| 5 | Low |
| 6 | Low |
| 8 | Medium |
| 9 | High |
| 10 | High |
| 11 | High |
| 12 | Medium |
| 13 | High |
| 14 | Medium |
| 15 | Medium |
| 16 | Medium |
| 17 | High |
| 18 | Medium |
| 19 | High |
| 20 | Medium |
| 21 | Medium |
| 22 | High |
| 23 | High |
| 24 | Medium |
| 25 | Medium |
| 26 | Medium |
| 27 | Low |
| 28 | Medium |
| 29 | High |
| 30 | High |
| 31 | Medium |
| 32 | Low |
| 33 | High |
| 34 | Low |
| 35 | Medium |
| 36 | High |
| 37 | Medium |
| 38 | High |
| 39 | Medium |
| 40 | High |
| 41 | Medium |
| 42 | Medium |
| 43 | Low |
| 44 | High |
| 45 | Medium |
| 46 | High |
| 47 | Medium |
| 48 | Low |
| 49 | High |
| 50 | High |
| 51 | Medium |
| 52 | High |

High = IC50 < 500 nM;
Medium = IC50 > 500 nM and < 5 μM;
Low > 5 μM

REFERENCES

Bohn, T. et al. (2018). Tumor immunoevasion via acidosis-dependent induction of regulatory tumor-associated macrophages. *Nature Immunology,* 1319-1326.

Damaghi, M. et al. (2013). pH Sensing and Regulation in Cancer. *Frontiers in Physiology.*

Gaublomme, J. et al. (2015). Single-Cell Genomics Unveils Critical Regulators of Th17 Cell Pathogenicity. *Cell,* 1400-1412.

Hernandez, J. (2018). GPR65, a critical regulator of Th17 cell pathogenicity, is regulated by the CRTC2/CREB pathway. *The Journal of Immunology,* 200 (Supplement).

Korn, T. et al. (2009). IL-17 and Th17 Cells. Annual Reviews in Immunology, 485-517.

Wang, J. et al. (2004). TDAG8 is a proton-sensing and psychosine-sensitive G-protein-coupled receptor. *Journal of Biological Chemistry,* 45626-45633.

Yoshida, N. et al. (2016). ICER is requisite for Th17 differentiation. *Nature Communications* 12993.
Hardin, M. et al. (2014). The clinical and genetic features of COPD-asthma overlap syndrome. Eur Respir J. 2014 August; 44(2):341-50.
Kottyan, L. et al. (2009). Eosinophil viability is increased by acidic pH in a cAMP- and GPR65-dependent manner. *Blood.* 2009 Sep. 24; 114(13):2774-82.
Tsurumaki, H. et al (2015). Int J Mol Sci. Protective Role of Proton-Sensing TDAG8 in Lipopolysaccharide-Induced Acute Lung Injury. December 4; 16(12):28931-42.
Schultz and Wolfe (2011), Organic Letters, Intramolecular Alkene Carboamination Reactions for the Synthesis of Enantiomerically Enriched Tropane Derivatives, 13 (11), 2962-2965

The invention claimed is:

1. A compound of formula (I), or a pharmaceutically acceptable salt or solvate thereof, (I)

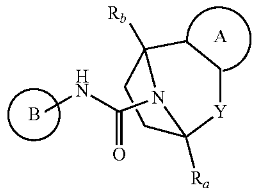

wherein:

ring A is benzene, pyridine, pyridone, pyridine N-oxide, pyrimidone, pyridazine, pyrazine, or isoxazole ring that is optionally substituted with one or more substituents selected from halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11'}$, OH, alkyl, haloalkyl, and aralkyl;

ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl, $CO_2$-alkyl and O-aryl;

Y is selected from $CH_2$, C═N—OH, and $CR_{10}R_{10'}$, wherein $R_{10}$ and $R_{10'}$ are each independently selected from H, F, alkyl, and haloalkyl;

$R_a$ and $R_b$ are each independently selected from H and alkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

2. A compound according to claim 1, wherein ring A is a benzene, pyridine, pyridone, pyridine N-oxide, pyrimidone, pyridazine, pyrazine, or isoxazole ring that is optionally substituted with one or more substituents selected from F, Cl, Br, I, CN, $C_1$-$C_6$ alkoxy, $NR_{11}R_{11'}$, OH, $C_1$-$C_6$ alkyl, phenyl, and $C_1$-$C_6$ haloalkyl.

3. A compound according to claim 1 wherein B is an optionally substituted monocyclic heteroaromatic group containing at least one nitrogen atom.

4. A compound according to claim 1 which is of formula (I.1), or a pharmaceutically acceptable salt or solvate thereof, (I.1)

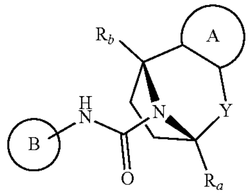

wherein A, Y, B, $R_a$ and $R_b$ are as defined in claim 1.

5. A compound according to claim 1 which is of formula (Ic), or a pharmaceutically acceptable salt or solvate thereof, (Ic)

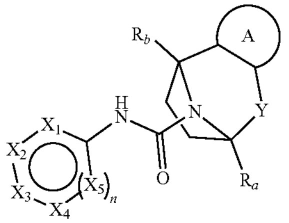

wherein where n is 0 or 1 and $X_1$-$X_5$ form a 5- or 6-membered heteroaromatic group containing at least one nitrogen atom, said heteroaromatic group being optionally substituted by one or more substituents selected from halo, CN, alkyl, alkoxy, haloalkyl, aryl, heteroaryl and O-aryl.

6. A compound according to claim 5 wherein n is 1, and $X_1$-$X_5$ form a 6-membered heteroaromatic group selected from pyridin-2-yl, pyridin-3-yl, pyridin-4-yl, pyrazin-2-yl, pyrimidin-2-yl, pyrimidin-4-yl and pyrimidin-5-yl, each of which is optionally substituted by one or more substituents selected from halo, CN, alkoxyl, alkyl, haloalkyl, aryl, heteroaryl and O-aryl.

7. A compound according to claim 5 which is of formula (Ia), or a pharmaceutically acceptable salt or solvate thereof, (Ia)

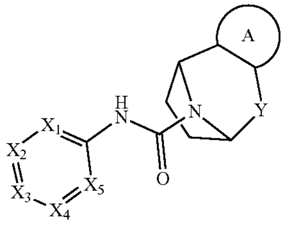

wherein:

$X_1$ is N or $CR_1$;

$X_2$ is N or $CR_2$;

$X_3$ is N or $CR_3$;

$X_4$ is N or $CR_4$;

$X_5$ is N or $CR_5$;

wherein at least one of $X_1$ to $X_5$ is N; and $R_1$-$R_5$ are each independently selected from H, halo, CN, alkoxyl, alkyl, haloalkyl, haloalkoxy, aryl, heteroaryl and O-aryl.

8. A compound according to claim 7, which is of formula (Ib), or a pharmaceutically acceptable salt or solvate thereof, (Ib)

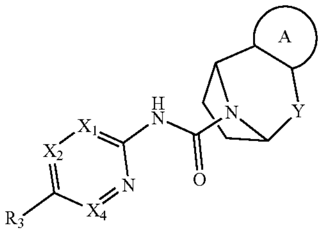

wherein:

$X_1$ is N or $CR_1$;

$X_2$ is N or $CR_2$;

$X_4$ is N or $CR_4$; and $R_1$, $R_2$, $R_3$ and $R_4$ are each independently selected from H, halo, haloalkyl, alkyl, alkoxy, CN, aryl, heteroaryl and O-aryl.

9. A compound according to claim 8 wherein:

$R_3$ is selected from halo and haloalkyl.

10. A compound according to claim 8 wherein $X_2$ is N, $X_1$ is $CR_1$ and $X_4$ is $CR_4$.

11. A compound according to claim 8 wherein $X_1$ is N, $X_2$ is $CR_2$ and $X_4$ is $CR_4$.

12. A compound according to claim 7, wherein $X_3$ is N, $X_1$ is $CR_1$, $X_2$ is $CR_2$, $X_4$ is $CR_4$ and $X_5$ is $CR_5$.

13. A compound according to claim 7, wherein $X_1$ is $CR_1$, $X_2$ is N, $X_3$ is $CR_3$, $X_4$ is $CR_4$ and $X_5$ is $CR_5$.

14. A compound according to claim 5, wherein:

n is 0, and $X_1$-$X_4$ form a 5-membered heteroaromatic group containing at least one nitrogen atom, said heteroaromatic group being optionally substituted by one or more substituents selected from halo, CN, alkyl, alkoxy, haloalkyl, aryl, heteroaryl, $CO_2$-alkyl, cycloalkyl, heterocycloalkyl and O-aryl.

15. A compound according to claim 5, which is of formula (Id), or a pharmaceutically acceptable salt or solvate thereof, (Id)

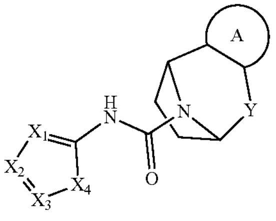

wherein:

$X_1$-$X_4$ form a heteroaromatic group containing at least one nitrogen atom, wherein:

$X_1$ is N or $CR_1$;

$X_2$ is N or $CR_2$;

$X_3$ is N or $CR_3$;

$X_4$ is selected from $NR_{15}$, O and S, where $R_{15}$ is H, alkyl or haloalkyl; and $R_1$-$R_3$ are each independently selected from H, halo, CN, alkoxyl, alkyl, haloalkyl, aryl, heteroaryl, heterocycloalkyl, cycloalkyl and O-aryl.

16. A compound according to claim 5, which is of formula (Ie), or a pharmaceutically acceptable salt or solvate thereof, (Ie)

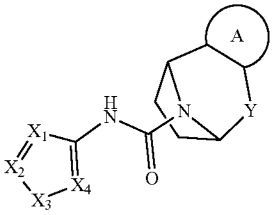

wherein:

$X_1$-$X_4$ form a heteroaromatic group containing at least one nitrogen atom, wherein:

$X_1$ is N or $CR_1$;

$X_2$ is N or $CR_2$;

$X_3$ is selected from $NR_{15}$, O and S, where $R_{15}$ is H, alkyl or haloalkyl;

$X_4$ is N or $CR_4$; and $R_1$, $R_2$ and $R_4$ are each independently selected from H, halo, CN, alkoxyl, alkyl, haloalkyl, aryl, heteroaryl, $CO_2$-alkyl and O-aryl.

17. A compound according to claim 1 wherein B is an optionally substituted bicyclic heteroaromatic group containing at least one nitrogen atom.

18. A compound according to claim 17 which is of formula (If), or a pharmaceutically acceptable salt or solvate thereof, (If)

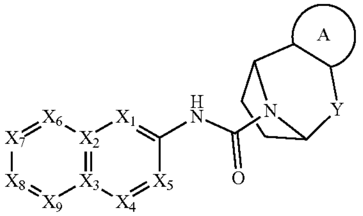

wherein $X_2$ and $X_3$ are both C, one, two or three of $X_1$, $X_4$, $X_5$-$X_9$ are N and the rest are selected from C—H, C-alkyl and C-haloalkyl.

19. A compound according to claim 17 wherein:

B is a bicyclic heteroaromatic group selected from the following:

(ij)

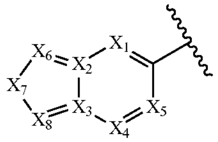

(Ik)

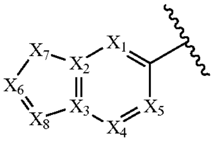

-continued
(Im)
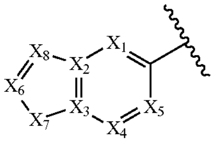
wherein:
$X_2$ and $X_3$ are both C;
$X_7$ is selected from O, S and $NR_{15}$, where $R_{15}$ is H, alkyl or haloalkyl; and
one, two or three of $X_1$, $X_4$, $X_5$, $X_6$ and $X_8$ are N and the rest are selected from C—H, C-alkyl and C-haloalkyl.
20. A compound according to claim 1, wherein ring A is selected from:
(i)
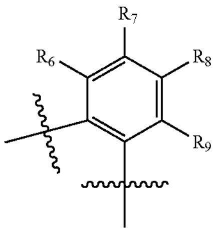
(ii)
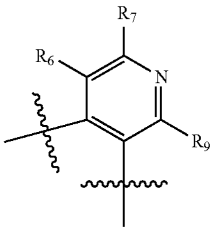
(iv)
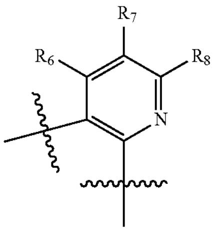
(v)
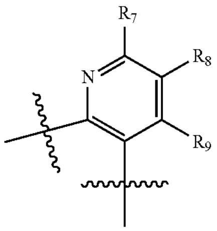
(vii)
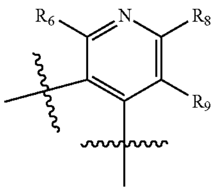
-continued
(viii)
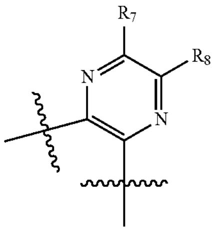
(ix)
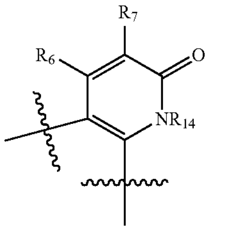
(x)
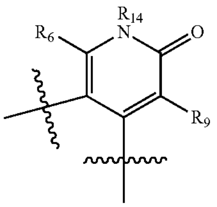
(xi)
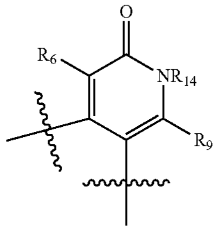
(xii)
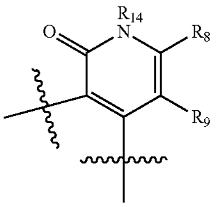
(xiii)
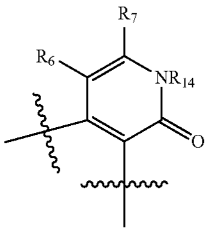
(xiv)
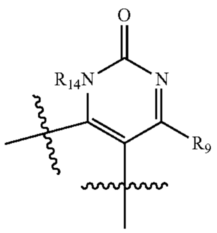

-continued
(xv)
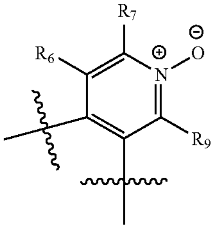
(xvi)
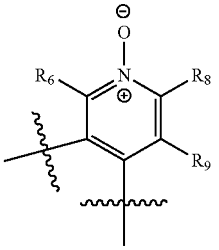
(xvii)
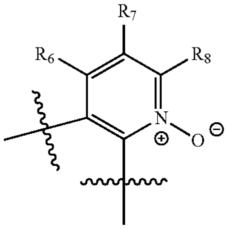
(xviii)
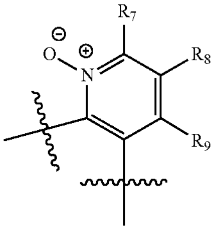
(xix)
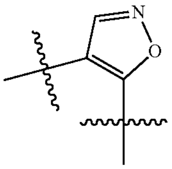
wherein $R_6$, $R_7$, $R_8$, and Ry are each independently selected from H, F, Cl, Br, I, CN, alkoxy, $NR_{11}R_{11'}$, OH, alkyl, phenyl and haloalkyl, and $R_{14}$ is H or alkyl, more preferably H.
21. A compound according to claim 20, wherein ring A is selected from:
(i)
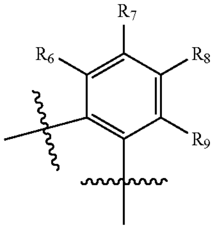
-continued
(ii)
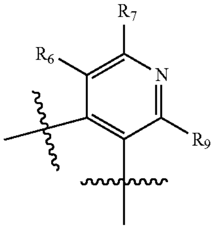
(iv)
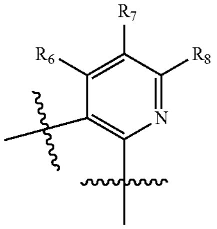
(v)
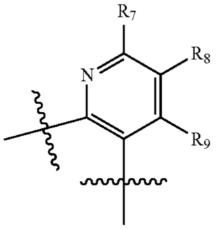
(vii)
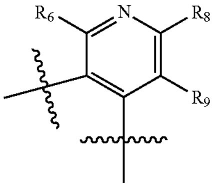
(viii)
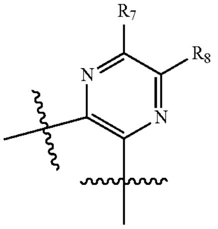
(ix)
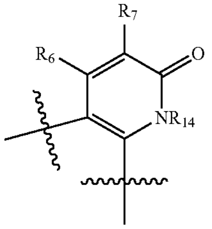
(x)
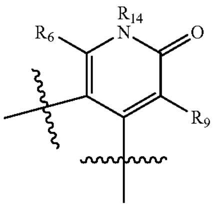

-continued
(xi)
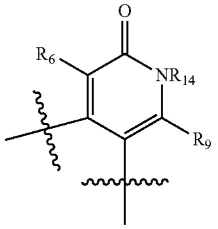
(xii)
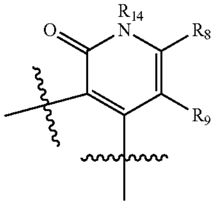
(xiii)
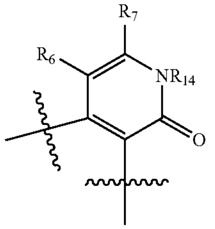
(xiv)
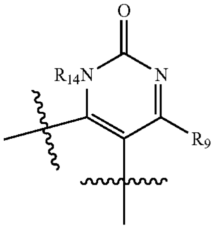
(xv)
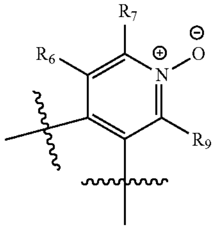
(xvi)
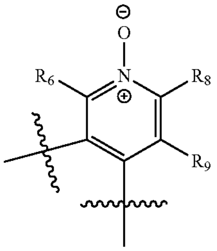
-continued
(xvii)
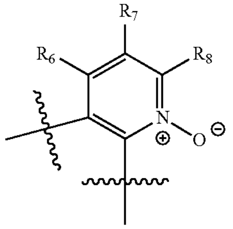
(xviii)
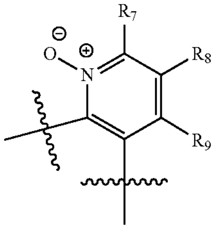
(xix)
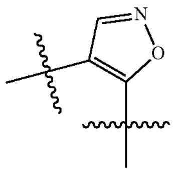
.
22. A compound according to claim 1, wherein $R_{10}$ and $R_{10'}$ are each independently selected from H and $C_1$-$C_6$ alkyl.
23. A compound according to claim 1, wherein Y is selected from $CH_2$ and C═N—OH.
24. A compound of formula (Ih), or a pharmaceutically acceptable salt or solvate thereof,
(Ih)
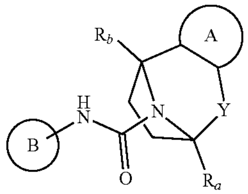
wherein:
ring A is selected from:
(i)
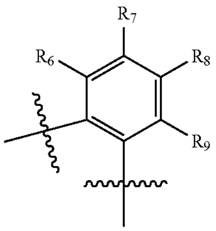

-continued
(ii)
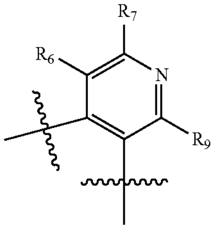
(iv)
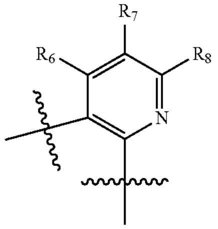
(v)
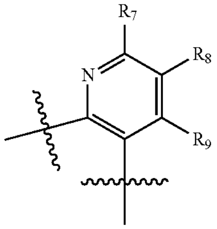
(vi)
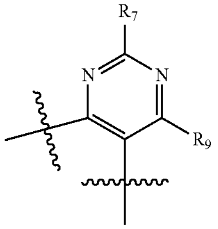
(vii)
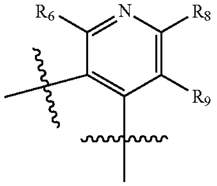
(viii)
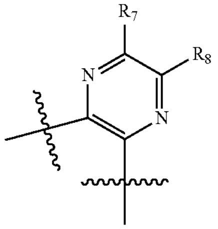
(ix)
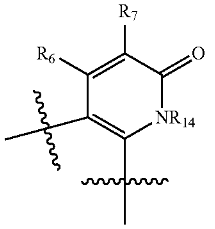
-continued
(x)
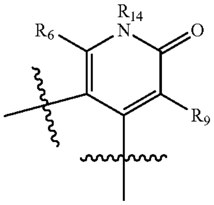
(xi)
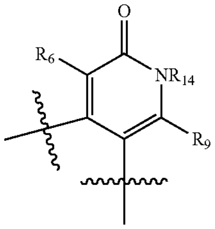
(xii)
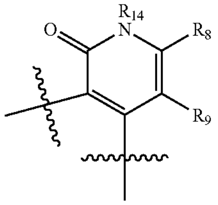
(xiii)
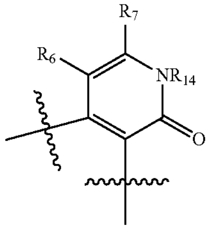
(xiv)
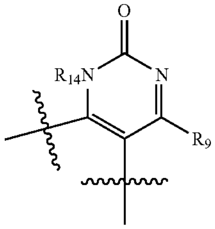
(xv)
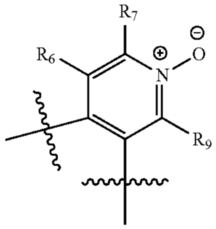
(xvi)
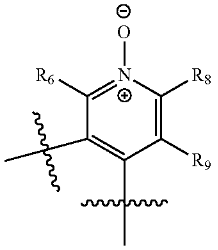

-continued (xvii)

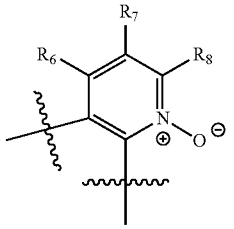

(xviii)

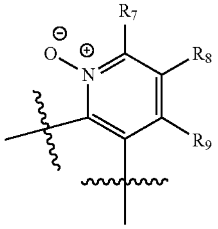

(xix)

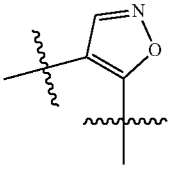

wherein $R_6$, $R_7$, $R_8$, and Ry are each independently selected from H, halo, CN, alkoxy, $NR_{11}R_{11'}$, OH, alkyl, haloalkyl, aralkyl, aryl, and heteroaryl, and wherein said aryl and heteroaryl substituents are in turn optionally substituted with one or more substituents each independently selected from halo, CN, alkoxy, $NR_{11}R_{11}$, OH, alkyl, haloalkyl, and aralkyl; and $R_{14}$ is H or alkyl;

ring B is a monocyclic or bicyclic heteroaromatic group containing at least one nitrogen atom, which is optionally substituted by one or more substituents selected from halo, CN, alkyl, alkoxy, haloalkyl, haloalkoxy, cycloalkyl, heterocycloalkyl, aryl, heteroaryl, $CO_2$-alkyl and O-aryl;

Y is selected from $CH_2$, C═N—OH, and $CR_{10}R_{10'}$, wherein $R_{10}$ and $R_{10'}$ are each independently selected from H, F, alkyl, and haloalkyl;

$R_a$ and $R_b$ are each independently selected from H and alkyl;

$R_{11}$ and $R_{11'}$ are each independently selected from H, alkyl, haloalkyl, $COR_{12}$, $CO_2R_{13}$ and $SO_2R_{16}$, wherein $R_{12}$, $R_{13}$ and $R_{16}$ are each independently alkyl.

25. A compound which is selected from the following:

1

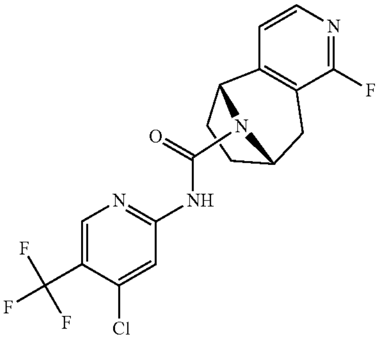

2

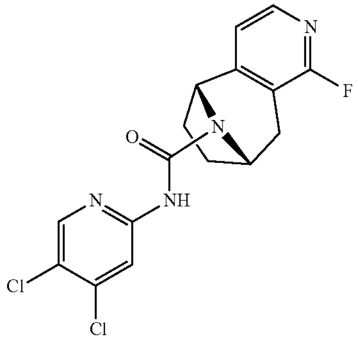

3

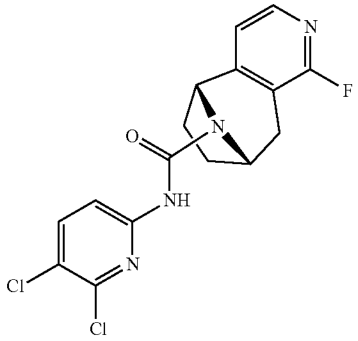

4

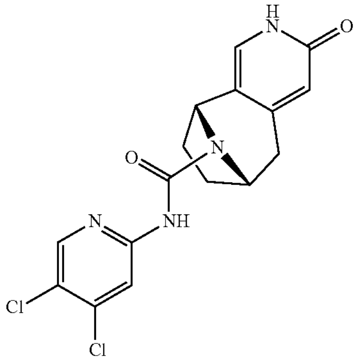

-continued
5
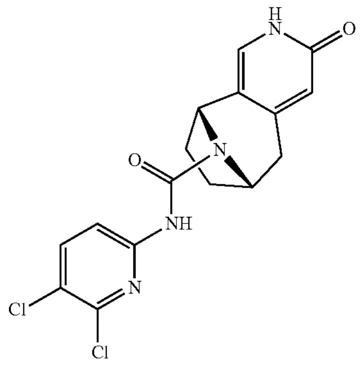
6
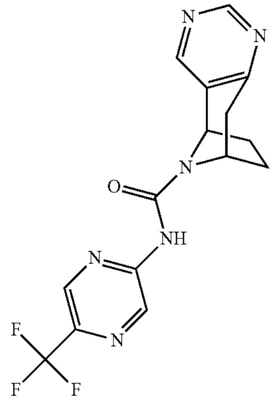
8
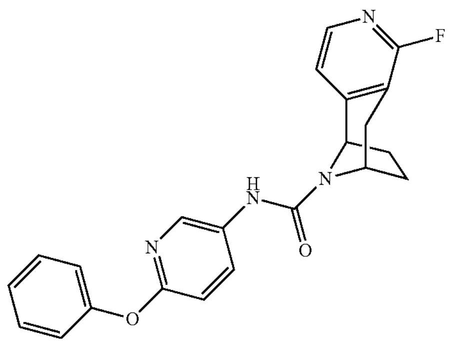
9
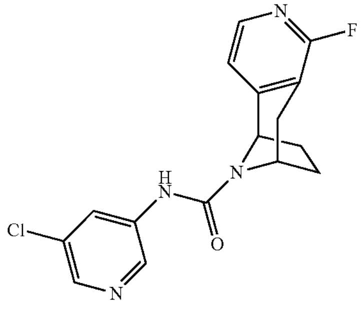
-continued
10
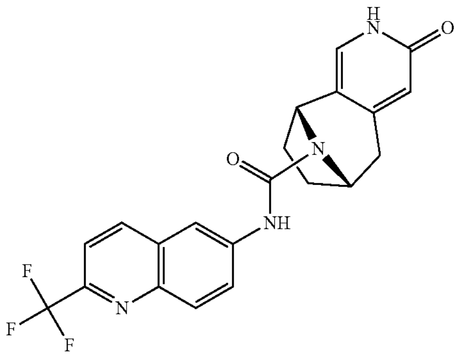
11
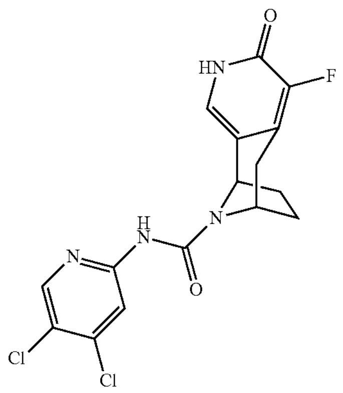
12
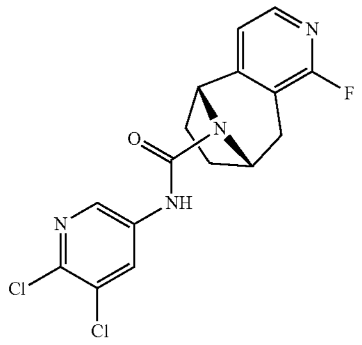
13
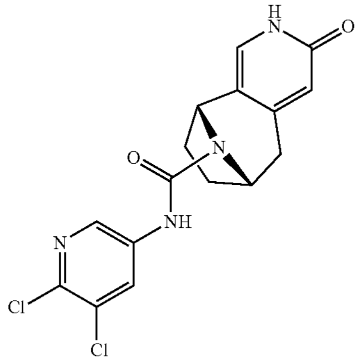

-continued
14
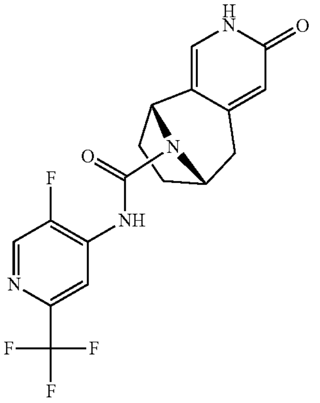
15
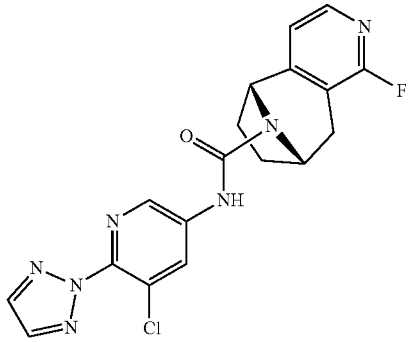
16
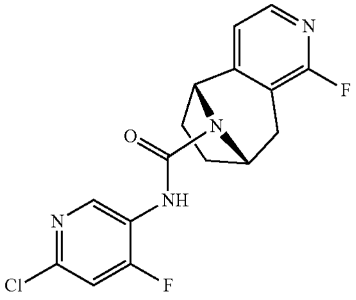
17
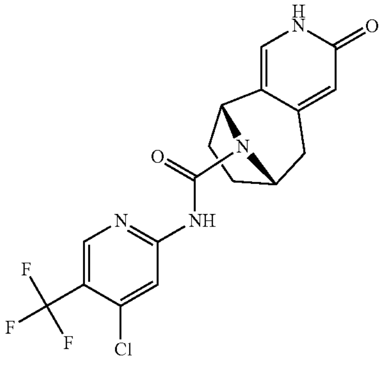
-continued
18
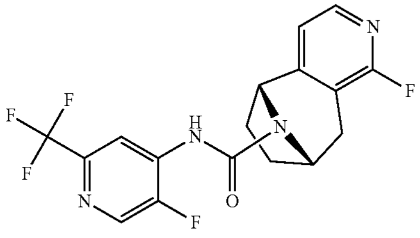
19
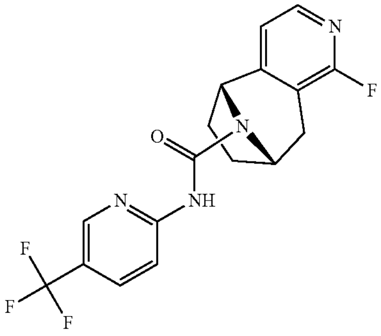
20
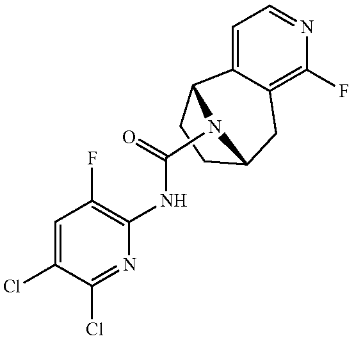
21
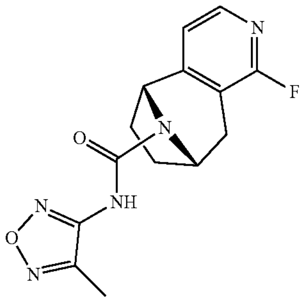
22
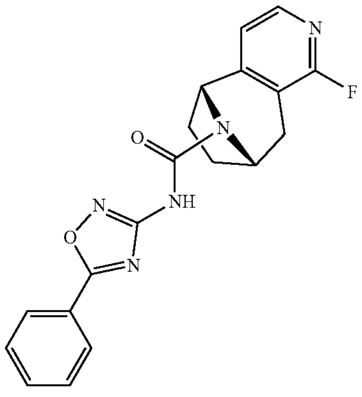

23
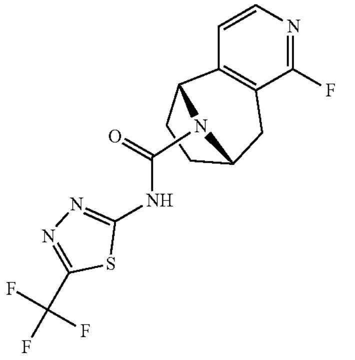
24
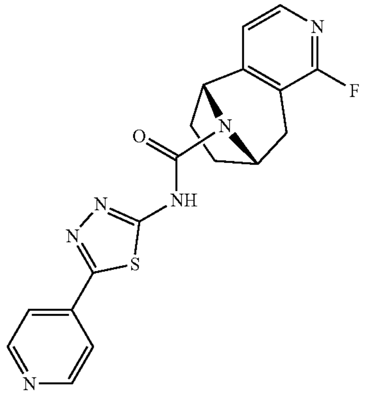
25
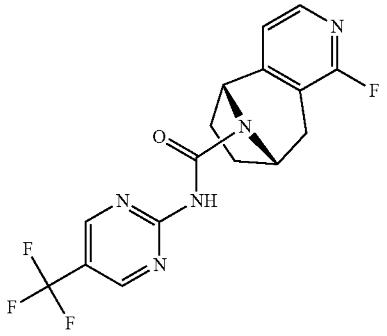
26
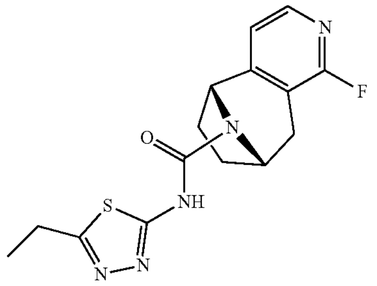
27
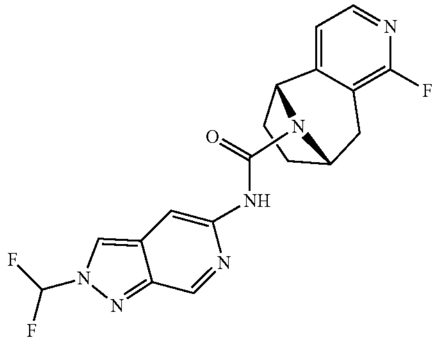
28
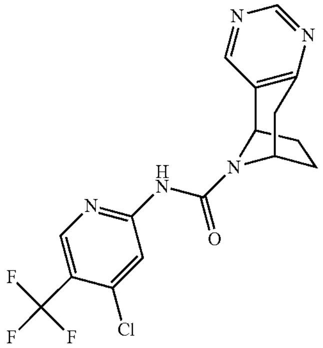
29
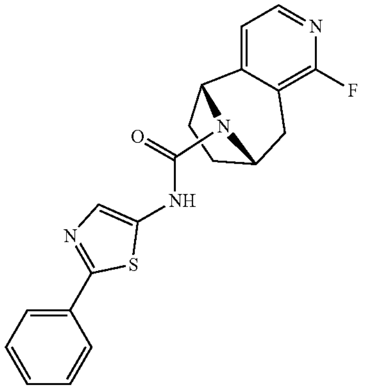
30
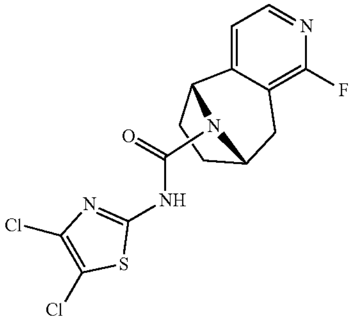

-continued
31
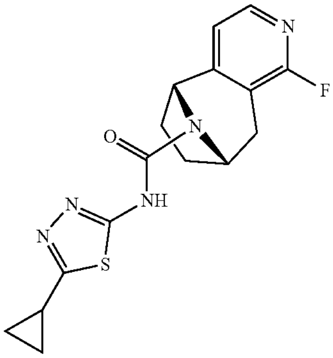
32
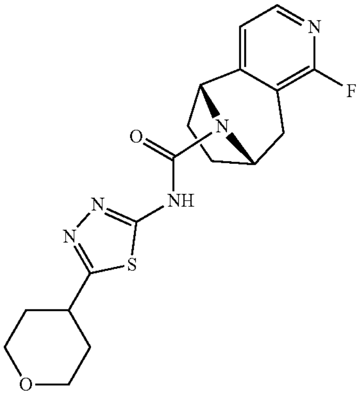
33
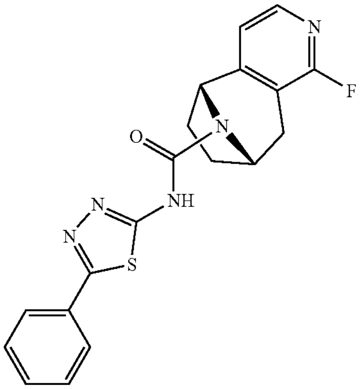
34
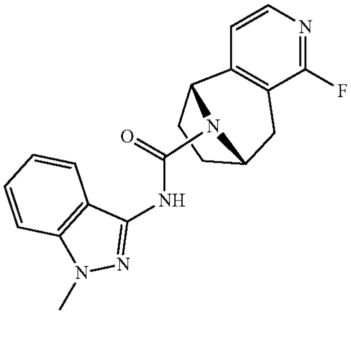
-continued
35
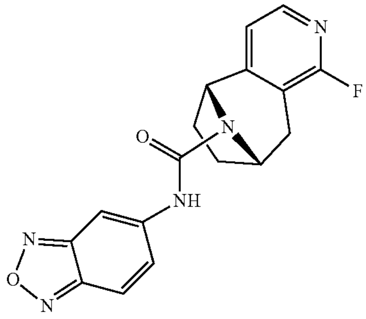
36
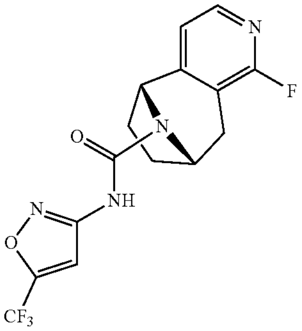
37
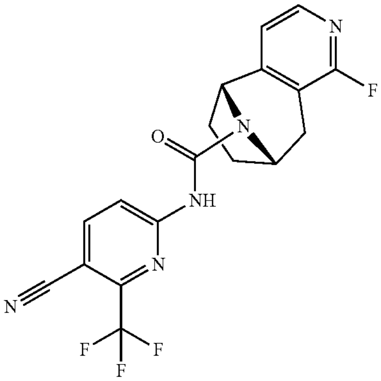
38
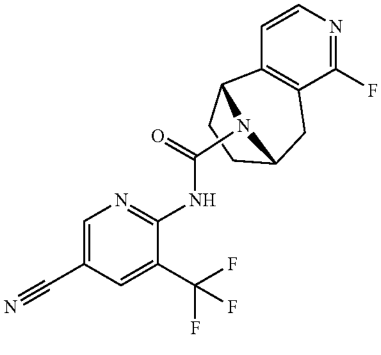

-continued
39
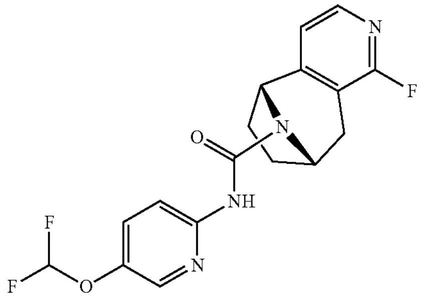
40
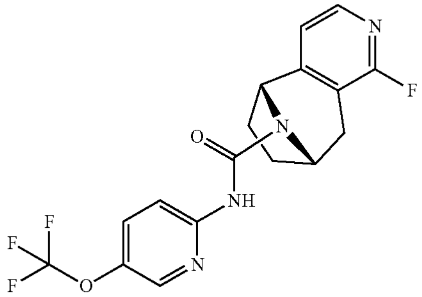
41
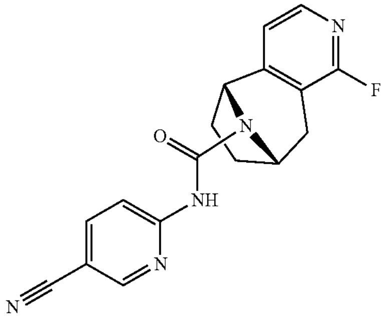
42
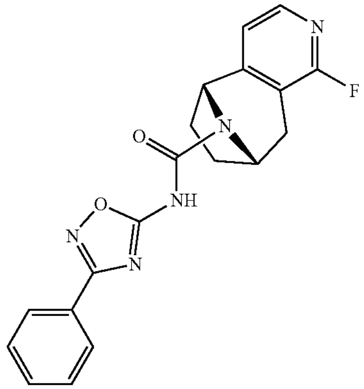
43
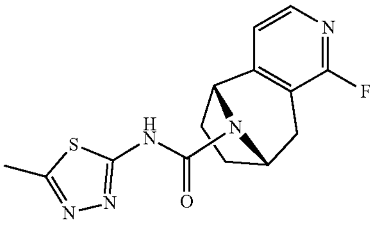
-continued
44
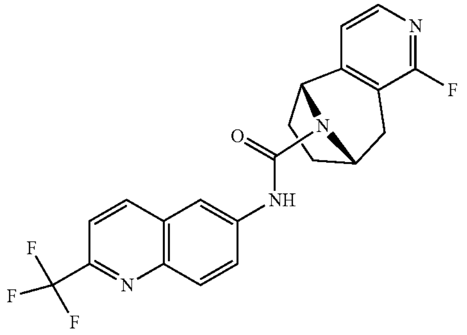
45
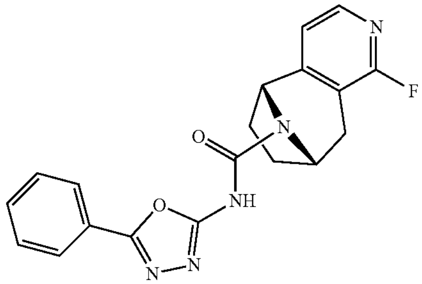
46
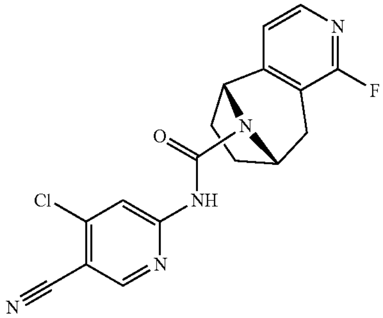
47
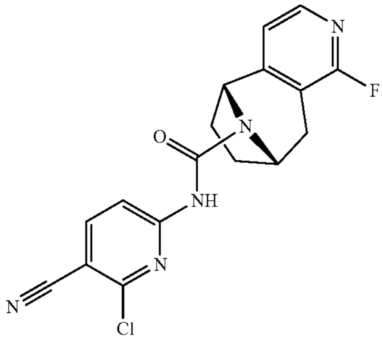
48
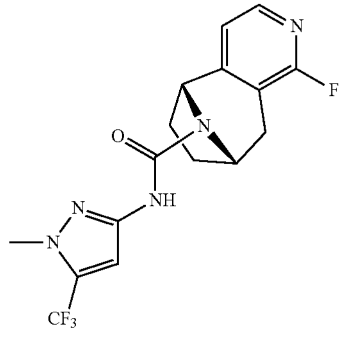

-continued

49

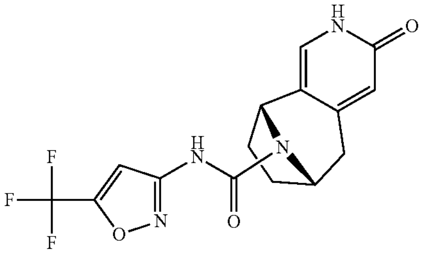

50

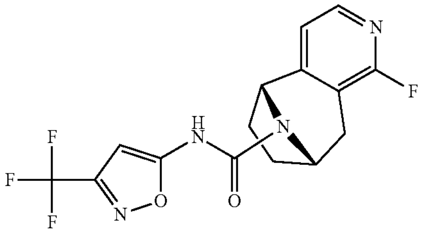

51

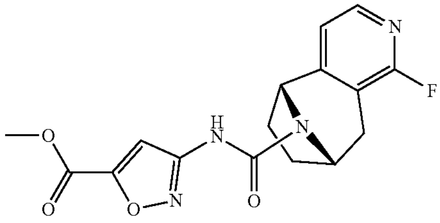

-continued

52

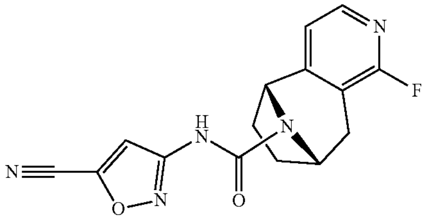

and enantiomers thereof, and mixtures of enantiomers thereof, including racemic mixtures, and pharmaceutically acceptable salts and solvates thereof.

26. A pharmaceutical composition comprising a compound according to claim 1, and a pharmaceutically acceptable diluent, excipient, or carrier.

27. A method of treating a disorder selected from a proliferative disorder, an immune disorder, asthma, chronic obstructive pulmonary disease (COPD) and acute respiratory distress syndrome (ARDS) said method comprising administering to a subject a therapeutically effective amount of a compound according to claim 1.

28. A method according to claim 27, wherein the treatment comprises modulating GPR65.

29. A method according to claim 27, wherein:

the disorder is a proliferative disorder, and the proliferative disorder is cancer.

30. A method according to claim 27 wherein the disorder is an immune disorder.

31. A method according to claim 27, which comprises treating a disorder selected from asthma, chronic obstructive pulmonary disease (COPD) and acute respiratory distress syndrome (ARDS).

* * * * *